United States Patent
Routh et al.

(10) Patent No.: US 12,404,296 B2
(45) Date of Patent: *Sep. 2, 2025

(54) POLY(A)-CLICKSEQ CLICK-CHEMISTRY FOR NEXT GENERATION 3-END SEQUENCING WITHOUT RNA ENRICHMENT OR FRAGMENTATION

(71) Applicant: Board of Regents, The University of Texas System, Austin, TX (US)

(72) Inventors: Andrew Routh, Galveston, TX (US); Eric J. Wagner, Galveston, TX (US); Ping Ji, Houston, TX (US); Elizabeth Jaworski, La Marque, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/412,024

(22) Filed: Aug. 25, 2021

(65) Prior Publication Data
US 2022/0002337 A1  Jan. 6, 2022

Related U.S. Application Data

(62) Division of application No. 16/282,159, filed on Feb. 21, 2019, now Pat. No. 11,149,053.

(60) Provisional application No. 62/634,095, filed on Feb. 22, 2018.

(51) Int. Cl.
| | |
|---|---|
| *C12Q 1/68* | (2018.01) |
| *C07H 21/02* | (2006.01) |
| *C07H 21/04* | (2006.01) |
| *C12Q 1/6806* | (2018.01) |
| *C12Q 1/6855* | (2018.01) |
| *C12Q 1/686* | (2018.01) |
| *C12Q 1/6869* | (2018.01) |

(52) U.S. Cl.
CPC .......... *C07H 21/04* (2013.01); *C07H 21/02* (2013.01); *C12Q 1/6806* (2013.01); *C12Q 1/6855* (2013.01); *C12Q 1/686* (2013.01); *C12Q 1/6869* (2013.01); *C12Y 207/07006* (2013.01); *C12Y 207/07007* (2013.01); *C12Y 207/07049* (2013.01)

(58) Field of Classification Search
CPC ...... C07H 21/04; C07H 21/02; C12Q 1/6806; C12Q 1/6855; C12Q 1/686; C12Q 1/6869; C12Q 2525/191; C12Y 207/07006; C12Y 207/07007; C12Y 207/07049
See application file for complete search history.

(56) References Cited

U.S. PATENT DOCUMENTS

| | | | | |
|---|---|---|---|---|
| 10,633,696 B2* | 4/2020 | Kim | ................... | C12Q 1/6876 |
| 2010/0159526 A1* | 6/2010 | Jendrisak | ............. | C12Q 1/6806 |
| | | | | 435/91.1 |

OTHER PUBLICATIONS

Routh et al. ClickSeq: Fragmentation-free next-generation sequencing via click-ligation of adaptors to stochastically terminated 3'-azido cDNAs. J. Molecular Biology (2015) 427(16):2610-2616. (Year: 2015).*
Routh et al. Poly(A0-clickseq: click-chemistry for next-generation 3'-end sequencing without RNA enrichment or fragmentation. Nucleic Acids Research, vol. 45(12) e112, p. 1-16, (2017).*
Stratagene Catalog. Gene Characterization kits, p. 39, (1988).*

* cited by examiner

*Primary Examiner* — Suryaprabha Chunduru
(74) *Attorney, Agent, or Firm* — Edwin S. Flores; Daniel J. Chalker; Chalker Flores, LLP

(57) ABSTRACT

The present invention includes a method and kit for cDNA synthesis of a 3'UTR/poly(A) tail junction of cellular RNA comprising: obtaining RNA comprising a 3'UTR/poly(A) junction and a poly(a) tail; combining the RNA with three terminating nucleotides of modified-deoxyGTP, modified-deoxyCTP and modified-deoxyATP, dNTPs, and adaptor sequence-oligo-dT; performing reverse transcription of the RNA with a reverse transcriptase primed with the adaptor sequence-oligo-dT to form terminated cDNA fragments that are stochastically terminated upstream of the 3'UTR/poly(A) junction, but not within the poly(A) tail; isolating the terminated cDNA fragments; chemically ligating a functionalized 5' adaptor to the terminated cDNA; and amplifying the chemically-ligated cDNA into an amplification product, wherein the cDNA is enriched for sequences at the 3'UTR/poly(A) tail junction without fragmentation or enzymatic ligation.

13 Claims, 25 Drawing Sheets
Specification includes a Sequence Listing.

D Topology of final library

B

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
gaattaatac gactcactat aggg                                    24

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
agcgctggac agaaaagtgt                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
cgcctggttg gtgtacttct                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
agggcctcaa gagattgcta                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
atcgtgtcct caacaatcca                                          20

<210> SEQ ID NO 6
<211> LENGTH: 59
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (35)..(38)
<223> OTHER INFORMATION: n is a, c, g, or t

<400> SEQUENCE: 6
gtgactggag ttcagacgtg tgctcttccg atctnnnntt tttttttttt tttttttt    59

```
<210> SEQ ID NO 7
<211> LENGTH: 60
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(4)
<223> OTHER INFORMATION: n is a, c, g, or t

<400> SEQUENCE: 7
nnnnagatcg aagagcgtc gtgtagggaa agagtgtaga tctcggtggt cgccgtatca      60

<210> SEQ ID NO 8
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (25)..(30)
<223> OTHER INFORMATION: n is a, c, g, or t

<400> SEQUENCE: 8
caagcagaag acggcatacg agatnnnnnn gtgactggag ttcagacgtg t              51

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
aatgatacgg cgaccaccga g                                               21

<210> SEQ ID NO 10
<211> LENGTH: 15
<212> TYPE: DNA
<213> ORGANISM: Artificial Sequence
<220> FEATURE:
<223> OTHER INFORMATION: Synthetic primer

<400> SEQUENCE: 10
aaaaaaaaaa aaaaa                                                      15

<210> SEQ ID NO 11
<211> LENGTH: 59
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (35)..(38)
<223> OTHER INFORMATION: n is a, c, g, or t

<400> SEQUENCE: 11
gtgactggag ttcagacgtg tgctcttccg atctnnnntt tttttttttt tttttttt       59

<210> SEQ ID NO 12
<211> LENGTH: 58
<212> TYPE: DNA
<213> ORGANISM: Artificial Sequence
<220> FEATURE:
<223> OTHER INFORMATION: Synthetic primer
```

```
<400> SEQUENCE: 12
agatcggaag agcgtcgtgt agggaaagag tgtagatctc ggtggtcgcc gtatcatt        58

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
aatgatacgg cgaccaccga g                                                21

<210> SEQ ID NO 14
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (25)..(30)
<223> OTHER INFORMATION: n is a, c, g, or t

<400> SEQUENCE: 14
caagcagaag acggcatacg agatnnnnnn gtgactggag ttcagacgtg t               51

<210> SEQ ID NO 15
<211> LENGTH: 13
<212> TYPE: DNA
<213> ORGANISM: Artificial Sequence
<220> FEATURE:
<223> OTHER INFORMATION: Synthetic primer

<400> SEQUENCE: 15
agatcggaag agc                                                         13
```

POLY(A)-CLICKSEQ CLICK-CHEMISTRY FOR NEXT GENERATION 3-END SEQUENCING WITHOUT RNA ENRICHMENT OR FRAGMENTATION

CROSS-REFERENCE TO RELATED APPLICATIONS

This application claims priority to U.S. Ser. No. 16/282,159, filed Feb. 21, 2019, which claims priority to U.S. Provisional Application Ser. No. 62/634,095, filed Feb. 22, 2018, the entire contents of which are incorporated herein by reference.

STATEMENT OF FEDERALLY FUNDED RESEARCH

None.

TECHNICAL FIELD OF THE INVENTION

The present invention relates in general to the field of next generation sequencing, and more particularly, to the novel Poly(A)-ClickSeq: click-chemistry for next-generation 3'-end sequencing without RNA enrichment or fragmentation.

BACKGROUND OF THE INVENTION

Without limiting the scope of the invention, its background is described in connection with ClickSeq chemistry.

With the exception of replication-dependent histone mRNAs, poly(A) tails are ubiquitous to all eukaryotic mRNAs and function to stimulate translation and impart protection from cellular exonucleases (reviewed in (1)). Not surprisingly, the 3' termini of many RNA viruses, including picornaviruses (2) and HIV (3), have also been found to possess poly(A) tails. Cellular mRNA receive poly(A) tails through the process of cleavage and polyadenylation where the pre-mRNA is co-transcriptionally cleaved and subsequently used as a substrate for poly(A) polymerase. The location of cleavage and polyadenylation near the 3' end of a pre-mRNA is governed by three primary sequence elements: the hexameric polyadenylation signal (PAS, typically AWUAAA)(4), the cleavage site (typically a CA dinucleotide), and the downstream sequence element (DSE, typically U/UG rich). The collective adherence to consensus that these three elements possess is thought to dictate the overall efficiency of cleavage and polyadenylation at a particular site (5). The enzymatic process of cleavage and polyadenylation is carried out by a group of proteins called the cleavage and polyadenylation (CPA) complex that contains at least fifteen subunits, the core members of which are conserved from yeast to humans (reviewed in (6)). Complete loss of activity of any of these core CPA subunits leads to broad failure to produce mRNA ultimately resulting in loss of cell viability.

While initially thought to be a constitutive or housekeeping event, recent work from many laboratories have shown that cleavage and polyadenylation is highly dynamic (reviewed in (7)). Underscoring its importance, it has been observed that greater than 50% of mammalian mRNA have multiple potential cleavage and polyadenylation sites giving rise distinct mRNA isoforms of different length (8). This process, termed alternative polyadenylation (APA) dramatically increases the known diversity of the eukaryotic transcriptome (reviewed in (9,10)). The preponderance of data demonstrates that APA is developmentally regulated (11,12), can occur as tissues become more differentiated (13,14), when they are subject to cellular stress (15), or during diseased states such as cellular transformation (16). In particular it has been shown that when cells are induced to proliferate and/or undergo cellular transformation, there is a global trend toward the selective use of proximal poly(A) signals (pPAS) resulting in the production of mRNA with truncated 3'UTR that are not effectively targeted by miRNA (17,18). The mechanisms that manage APA regulation are less clear and several factors have been identified that can influence poly(A) site selection including chromatin or DNA modification (19,20), changes in RNA polymerase II elongation efficiency (21), and modulation of RNA binding/processing factors that are known to play a role in cleavage and polyadenylation (22-29). Of the CPA machinery, either increases in CstF64 expression (30) or decreases in CFIm complex member levels (23,24,31) leads to broad shortening of 3'UTRs suggesting that these two factors may play antagonistic roles in governing poly(A) site selection.

In light of the recent appreciation for APA, profiling the position of the poly(A) tail using high-throughput sequencing technologies is critical to understand the complex interplay of poly(A) tail location with mRNA stability, degradation and translation. In the simplest manner, the positions of poly(A) tails can be directly extracted from both short-read RNA-seq and long-read nanopore or Pacbio (e.g. IsoSeq) sequencing by extracting non-reference 'A's from mapped sequence reads (32). Alternatively, approaches have been developed that infer poly(A) tail position and abundances through computational analysis of standard RNA-seq using designer algorithms catered to measure the relative density of sequence reads within the 3'UTR relative to that observed in the coding regions (33). The advantage of these approaches is that they only require standard RNA-seq analysis and can be employed retrospectively onto existing datasets. However, they have the disadvantage in that precise poly(A) site junctions are not enriched relative to the rest of the transcriptomic data and so datasets are invariably large and require high depth sequencing runs (>100M reads) as only a subset of the RNA-seq will contribute to the analysis.

As a result, a number of strategies have been developed with the specific goal of enriching for the junction of the encoded 3'UTR ends and the beginning of the non-templated poly(A) tail (11,13,34-41). Common themes found in several of these techniques are the enrichment for poly(A)+ RNA from total RNA, fragmentation of mRNA using a variety of approaches (e.g. enzymatic, heat, sonication), and attachment of an adaptor to the 3' end either through the use of a splinted oligo or directly to the terminus of the poly(A) tail. These initial steps can also involve the use of a biotin-containing oligonucleotide to allow for purification of the desired library intermediates using streptavidin magnetic beads. These approaches typically utilize between 1-20M reads and have the advantage of allowing precise mapping of the position of the poly(A) tail addition. However, these approaches often entail complex experimental pipelines and purification strategies that can impart sample bias and reduce throughput capacity. Importantly, these challenges can reduce the number of core facilities offering these types of sequencing technologies thereby limiting their application only to laboratories with more than routine experience in sequencing library preparation. Thus, a need remains for improved methods for sequencing and determining the presence of cleavage and polyadenylation sites giving rise distinct mRNA isoforms of different lengths.

SUMMARY OF THE INVENTION

In one embodiment, the present invention includes a method for cDNA synthesis of an RNA 3' end and poly(A) tail junction of RNA comprising: obtaining RNA comprising an RNA 3' end, a poly(A) junction, and a poly(A) tail; combining the RNA with three terminating nucleotides of modified-deoxyGTP, modified-deoxyCTP and modified-deoxyATP, dNTPs, and adaptor sequence-oligo-dT; performing reverse transcription of the RNA with a reverse transcriptase primed with the adaptor sequence-oligo-dT to form terminated cDNA fragments that are stochastically terminated upstream of the RNA 3' end and poly(A) junction, but not within the poly(A) tail; isolating the terminated cDNA fragments; chemically ligating a functionalized 5' adaptor to the terminated cDNA; and amplifying the chemically-ligated cDNA into an amplification product, wherein the cDNA is enriched for sequences at the RNA 3' end and poly(A) tail junction without fragmentation or enzymatic ligation. In one aspect, the modified-deoxyGTP, modified-deoxyCTP and modified-deoxyATP are 2'- or 3'-azido-nucleotides selected from azido-GTP (AzGTP), 2'- or 3'-azido-CTP (AzCTP), and 2'- or 3'-azido-ATP (AzATP), or propargyl-GTP, CTP, or ATP. In another aspect, a ratio of the three 2'- or 3'-azido-nucleotides (AzGTP, AzCTP and AzATP) to dNTPs is 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM:1 mM. In another aspect, a ratio of AzGTP:AzCTP:AzATP is x:y:z, wherein x is 0.1-10.0, y is 0.1-10.0, and z is 0.1-10.0. In another aspect, the method further comprises purifying the cDNA away from the 3'-azido-nucleotides after the reverse transcription and before the amplification step. In another aspect, the purification step is by column separation, magnetic bead separation, or streptavidin magnetic bead wash. In another aspect, the method further comprises separating the amplification products according to their length, by gel electrophoresis, polyacrylamide gel electrophoresis, capillary electrophoresis, pulsed-field electrophoresis, agarose gel electrophoresis, PAGE, Solid Phase Reversible Immobilization (SPRI) size fractionation, or pulsed-field capillary electrophoresis. In another aspect, the step of chemically ligating is defined further as click-ligating an alkyne-functionalized 5' adaptor to the azido-terminated cDNA, or an azide-functionalized 5' adapted to the propargyl-terminated cDNA, is defined further as taking place in a buffered solution comprising: a solvent; with or without metal catalysts selected from copper and ruthenium; a chelating ligand; and an accelerant. In another aspect, the method further comprises purifying the chemically ligated-cDNA-adaptor away from unligated adaptors before the amplification step. In another aspect, the purification step is by column separation, magnetic bead separation, or streptavidin magnetic bead wash. In another aspect, the reverse transcription is performed by a reverse transcriptase (RT) derived from Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (−) Reverse Transcriptase, SuperScript II Reverse Transcriptase, SuperScript III Reverse Transcriptase, SuperScript IV Reverse Transcriptase, thermostable group II intron reverse transcriptases (TGIRT), Terminator DNA Polymerase, or ThermoScript Reverse Transcriptase, wherein an RNase H activity of these RTs is present, reduced or not present. In another aspect, the method further comprises determining an identity or sequence of the amplification products by an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, a sample contains total RNA or mRNA, preferably purified RNA or mRNA, from a biological fluid, biopsy, cells, or tissue that comprise the RNA with the RNA 3' end and poly(A) tail junction. In another aspect, high stringency salt conditions are used for the step of reverse transcription, the amplification step, or both. In another aspect, a selectivity of the reverse transcription, the amplification, or both, is increased by using trehalose, betaine, tetramethylammonium chloride, tetramethylammonium oxalate, formamide and oligo-blockers, or dimethylsulfoxide during the polymerase chain reaction, to reduce an occurrence of mispriming. In another aspect, a DNA polymerase used for the amplification reaction is Taq DNA polymerase, Tfl DNA polymerase, a Taq DNA polymerase, a Klenow fragment, Sequenase or Klentaq an enzyme with proof reading activity, preferably selected from the PFU, Ultma, Vent, Deep Vent, PWO, or Tli polymerase. In another aspect, the method further comprises purifying a PCR product from the step of amplifying the clicked-cDNA step with a column or beads. In another aspect, the method further comprises determining a sequence of the amplified product. In another aspect, the alkyne-functionalized, or azide-functionalized, 5' adaptor comprises all nucleotides, $N_{0-12}$ as a click adapter, semi-random primers, or a specific template primer sequence, or the adapter comprises a unique sequence. In another aspect, the terminating deoxynucleotides contain a chemically reactive functional group at either the 3' or 2' site of the ribose ring including but not limited to azido-nucleotides (AzGTP, AzCTP and AzATP), amino-nucleotides (AmGTP, AmCTP, AmATP), propargyl-nucleotides (propargyl-GTP, propargyl-CTP, and propargyl-ATP) or halogenated nucleotides (Hal-GTP, Hal-CTP and Hal-ATP).

In another embodiment, the present invention includes a kit for cDNA synthesis of an RNA 3' end, a poly(A) junction, and a poly(A) tail of RNA comprising: one or more vials comprising three terminating nucleotides of modified-deoxyGTP, modified-deoxyCTP and modified-deoxyATP, dNTPs, and adaptor sequence-oligo-dT; one or more vials comprising a reverse transcriptase; a cDNA fragment isolating kit; one or more vials comprising components for chemically ligating a functionalized 5' adaptor to the cDNA; a DNA amplification kit comprising for amplifying the chemically-ligated cDNA into an amplification product; and instructions for amplification of the RNA 3' end and poly(A) tail junction without fragmentation or enzymatic ligation. In one aspect, the terminating modified-deoxyGTP, modified-deoxyCTP and modified-deoxyATP are 2'- or 3'-azido-nucleotides (AzGTP, AzCTP and AzATP) or 3'-(O-Propargyl)-NTPs that pair with an alkyne or azide modified oligo during the 'click' reaction such as a hexanyl-oligo or azide-oligo. In another aspect, a ratio of the three 2'- or 3'-azido-nucleotides (AzGTP, AzCTP and AzATP), or propargyl-GTP, CTP, or ATP to dNTPs is 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM:1 mM. In another aspect, a ratio of AzGTP:AzCTP:AzATP is x:y:z, wherein x is 0.1-2.0, y is 0.1-2.0, and z is 0.1-2.0. In another aspect, the RNA 3' end and poly(A) tail junction is selected from at least one of a viral genomic RNA, total cellular RNA, poly(A)-selected RNA, unpurified DNA, or ribo-depleted RNA. In another aspect, the kit further comprises a cDNA purification kit for purifying the cDNA away from the 2' or 3'-azido-nucleotides after the reverse transcription and before the amplification step selected from a column separation kit, magnetic bead separation kit, or streptavidin magnetic bead kit. In another aspect, the kit further comprises a clicked-cDNA-adaptor purification kit for separating the clicked-cDNA-adaptor away from unligated alkyne-functionalized 5' adaptors or azide functionalized adapters when paired with propargyl-NTPs before the amplification step selected from a column separation kit, magnetic bead separation kit, or streptavidin magnetic bead kit. In another aspect, the click-ligating components comprise: an alkyne-functionalized 5' adaptor to the azido-terminated cDNA; a buffered solution comprising: a solvent mix comprising DMSO, water, and ethanol; metal catalysts selected from copper and ruthenium; a chelating ligand; and an accelerant. In another aspect, the reverse transcriptase (RT) is an RT derived from Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (–) Reverse Transcriptase, SuperScript II Reverse Transcriptase, SuperScript III Reverse Transcriptase, SuperScript IV Reverse Transcriptase, thermostable group II intron reverse transcriptases (TGIRT), Therminator DNA Polymerase, or ThermoScript Reverse Transcriptase, wherein an RNase H activity of these RTs is present, reduced or not present. In another aspect, a selectivity of the reverse transcription and/or amplification, preferably a polymerase chain reaction, is increased by using trehalose, betaine, tetramethylammonium chloride, tetramethylammonium oxalate, formamide and oligo-blockers, or dimethylsulfoxide during the polymerase chain reaction, to reduce the occurrence of mispriming. In another aspect, the kit further comprises a sequencing kit determining an identity or sequence of the amplification products by an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, a DNA polymerase used for the amplification reaction is Taq DNA polymerase, Tfl DNA polymerase, aTaq DNA polymerase, a Klenow fragment, Sequenase or Klentaq an enzyme with proof reading activity, preferably selected from the PFU, Ultma, Vent, Deep Vent, PWO, or Tli polymerases. In another aspect, the kit further comprises a kit for purifying a PCR product from the step of amplifying the clicked-cDNA step with a column or beads. In another aspect, the alkyne-functionalized 5' adaptor comprises all nucleotides $N_{0-12}$ as a click adapter, semi-random primers, or a specific template primer sequence, or the adapter comprises a unique sequence.

In yet another embodiment, the present invention includes a method for cDNA synthesis of an RNA 3' end and poly(A) tail junction of RNA comprising: performing reverse transcription of an RNA comprising an RNA 3' end, a poly(A) junction, and a poly(A) tail in the presence of three 2' or 3'-azido-nucleotides (AzGTP, AzCTP and AzATP), or propargyl-GTP, CTP, or ATP, dNTPs, and adaptor sequence-oligo-dT with a reverse transcriptase primed with the adaptor sequence-oligo-dT to form cDNA fragments that are stochastically terminated upstream of the 3'UTR/poly(A) junction, but not within the poly(A) tail to form azido-terminated cDNA; isolating the azido-terminated cDNA; click-ligating an alkyne-functionalized 5' adaptor to the azido-terminated cDNA to form a click-ligated cDNA; and amplifying the click-ligated cDNA into an amplification product, wherein the click-ligated cDNA is enriched for sequences at the RNA 3' end and poly(A) tail junction without fragmentation or enzymatic ligation.

In another embodiment, the present invention includes a method for cDNA synthesis of an RNA 3' end and poly(A) tail junction of cellular RNA comprising: obtaining RNA comprising an RNA 3' end, a poly(A) junction, and a poly(A) tail; combining the RNA with three 2'- or 3'-amino-nucleotides (AmGTP, AmCTP, AmATP), dNTPs, and adaptor sequence-oligo-dT; performing reverse transcription of the RNA with a reverse transcriptase primed with the adaptor sequence-oligo-dT to form amino-terminated cDNA fragments that are stochastically terminated upstream of the RNA 3' end and poly(A) tail junction, but not within the poly(A) tail; isolating an amino-terminated cDNA fragments; chemically ligating an phosphorylimidazolide-functionalized 5' adaptor to the amino-terminated cDNA; and amplifying the phosphoramidite-linked cDNA into an amplification product, wherein the cDNA is enriched for sequences at the RNA 3' end and poly(A) tail junction without fragmentation or enzymatic ligation. In one aspect, the reactive phosphorylimidazolide-functionalized 5' adaptors are generated by incubating 5' phosphate-labeled nucleic acid oligos with a carbodiimide crosslinker, preferably (EDC) (1-ethyl-3-(3-dimethylaminopropyl)carbodiimide hydrochloride) and preferably imidazole.

In another embodiment, the present invention includes a method for cDNA synthesis of an RNA 3' end a poly(A) tail junction of cellular RNA comprising: obtaining RNA comprising a RNA 3' end, a poly(A) junction, and a poly(A) tail; combining the RNA with three 2'- or 3'-azido-nucleotides (AzGTP, AzCTP and AzATP), dNTPs, and adaptor sequence-oligo-dT; performing reverse transcription of the RNA with a reverse transcriptase primed with the adaptor sequence-oligo-dT to form azido-terminated cDNA fragments that are stochastically terminated upstream of the 3'UTR/poly(A) junction, but not within the poly(A) tail; isolating an azido-terminated cDNA fragments; click-ligating an alkyne-functionalized 5' adaptor to the azido-terminated cDNA; and amplifying the click-ligated cDNA into an amplification product, wherein the cDNA is enriched for sequences at the 3'UTR/poly(A) tail junction without fragmentation or enzymatic ligation. In one aspect, the modified-deoxyGTP, modified-deoxyCTP and modified-deoxyATP are 2'- or 3'-azido-nucleotides selected from azido-GTP (AzGTP), 2'- or 3'-azido-CTP (AzCTP), and 2'- or 3'-azido-ATP (AzATP), or propargyl-GTP, CTP, or ATP. In another aspect, a ratio of the three 2'- or 3'-azido-nucleotides (AzGTP, AzCTP and AzATP) to dNTPs is 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM:1 mM.

BRIEF DESCRIPTION OF THE DRAWINGS

For a more complete understanding of the features and advantages of the present invention, reference is now made to the detailed description of the invention along with the accompanying figures and in which:

FIG. 1A) RT-PCR is launched from a non-anchored Poly(T) primer containing a portion of the Illumina p7 adaptor. RT-PCR is performed in the presence of AzATP, AzGTP and AzCTP, but not AzTTP, thus only allowing chain termination to occur upstream of the poly(A) tail in the 3'UTR. FIG. 1B) 3'-Azido-blocked cDNA fragments are 'click-ligated' to 5'hexynyl-functionalised DNA oligos containing the p5 Illumina adaptor. This yields triazole-linked ssDNA which can be PCR-amplified using primers to the p5 and p7 Illumina adaptors. FIG. 1C) The cDNA library is analysed by gel electrophoresis and should consist of a smear of DNA products centered around 200-300 bp. Appropriate cDNA fragment sizes are cut out of the gel and purified to yield a final library. FIG. 1D) The final library consists of DNA fragments containing the Illumina p5 adaptor, a portion of the 3'UTR, a stretch of As derived from both the RNA template and the poly(T) primer, and finally the p7 Illumina Indexing primer.

FIG. 1E shows a heat-map illustrating the impact of quality filters on the number of poly(A) sites discovered. To accept a putative poly(A) site, the mapped reads can be required to contain a minimum number of non-primer derived 'A's (x-axis) and each poly(A) site can be required to be represented by a minimum number of reads (y-axis). The number of poly(A) sites found (denoted by the colour-bar) using a range of combination of these two filters are shown here. In our analyses we required as least 5 reads each with 5 or more non-primer derived A's (indicated by red circle) to confirm a poly(A) site.

FIGS. 1F and 1G show nucleotides in the reference genomes upstream of poly(A) sites were found be enriched for A's. This indicates that these may be derived from internally primed sequences, rather than from genuine poly (A) tails. The number of nucleotides found upstream of each poly(A) sites were counted for FIG. 1F all poly(A) sites, and FIG. 1G after removing poly(A) sites containing 15 or more A's within 20 nucleotides of the upstream reference sequence. The x-axis indicates the nucleotide count, and the y-axis gives the relative frequency with which each nucleotide count was found.

FIG. 2A) The mapping of reads over the human gene Akt1 is illustrated. PAC-seq reads are only found at the very 3' end of the mRNA transcript. In contrast, standard RNAseq coverage is distributed over all the exons. FIG. 2B) PAC-seq and RNAseq coverage is illustrated over the abundant transcript, RPL12 (*Homo sapiens* ribosomal protein L12, mRNA). PAC-Seq reveals the exact site of the poly(A) tail with nucleotide resolution revealing that the precise cleavage sites is variable. The boxed region in FIG. 2B) is enlarged in FIG. 2C) to illustrate diversity of poly(A) sites. FIG. 2D) PAC-seq and RNAseq coverage is illustrated over the alternatively poly-adenylated transcript, VMA21 (*Homo sapiens* VMA21 vacuolar H+-ATPase homolog (*S. cerevisiae*) (VMA21), mRNA). PAC-Seq reveals two poly(A) sites (the distal and proximal site). Upon CF25Im knock-down, the proximal site is significantly enriched. This observation is also supported by the RNAseq data that shows reduced read coverage over the 3'UTR of VMA21 after CF25Im KD. The boxed region in FIG. 2D) is enlarged in FIG. 2E) to illustrate distal poly(A) site.

FIG. 2F shows di-nucleotides found in the reference genome at the poly(A) site cleavage site. The di-nucleotide surrounding detected poly(A)site found in the HiSeq HeLa sample were extracted from the reference human genome to find that the preferred cleavage site is most often UA, CA or GA, consistent with previous studies (1).

FIG. 2G shows CF25Im was knocked down in HeLa cells by siRNAs. A) Western blotting shows <95% depletion compared to control cell. CF25d was knocked down in S2 cells by dsRNA. B) Real-time quantitative PCR of total cellular RNA shows <90% depletion relative to control dsRNA.

FIGS. 5G to 5J show the frequency of AWUAAA and UGUA motifs found within 100 nt upstream of both proximal (pPAS) and distal (dPAS) poly(A) sites for shortened or lengthened mRNAs. Analyses showed similar trends when considering mRNAs with FIG. 5G) multiple PASs and >20% APA; FIG. 5H) only two PASs and >20% APA; FIG. 5I) only two PASs and >50% APA; and FIG. 5J) only two PASs and >80% APA.

FIG. 6A) Bar charts show the overlap of detected poly(A) sites with UCSC known gene annotations. Poly(A) sites were either found in known exons (Green), less than 500 nts upstream of known 3'UTR termini (Yellow), or in unannotated regions (Red). FIG. 6B) A scatter-plot comparing the frequency of poly(A) sites in both wild-type and CF25d KD S2 cell is shown revealing very high correlation between the two datasets (R=0.99). FIG. 6C) The effect of CF25d knockdown upon poly(A) site diversity is limited in *Drosophila*. Frequency of poly(A) sites in the same categories as described for FIG. 4B are shown. FIG. 6D) The frequency of AWUAAA and UGUA motifs found within 100 nt upstream of both proximal (pPAS) and distal (dPAS) poly (A) sites are shown for both shortened and lengthened mRNA.

(FIG. 10A) Total number of mapped reads from each sample type to different annotated regions of mRNAs is illustrated (dark cyan: terminal exons; light cyan: all exons; white: introns; yellow: 200 nts downstream of annotated 3' end; green: unannotated regions). Approximately 75-80% of all the reads map to exonic sequences (cyan), with a greater proportion of these mapping to the terminal exons (dark cyan) in the PAC-seq datasets. (FIG. 10B) Comparison of read coverage between the two sample preparation methods from the same source RNA. The upper light grey RNA-seq by ClickSeq method shows read coverage throughout the gene body due to the random nature of the RT-reaction steps. The lower dark grey PAC-seq coverage is specific for the 3'UTR. (FIG. 10C) Representative genes that showed down-regulation from LacZ control upon INTS11 knockdown, grey and red bars respectively. (FIG. 10D) Representative genes that showed upregulation from LacZ control upon INTS11 knockdown, grey and red bars respectively.

(FIG. 11A) Non-normalized Log 10 read counts between the three biological replicates of the INTS11 KD for the PAC-seq and RNA-seq methods, upper and lower rows respectively. The tight data patterns of both preparation methods indicate a high level of reproducibility. (FIG. 11B) Non-normalized $Log_{10}$ read counts of the three biological replicates of INTS11 KD comparing the read counts for all transcripts between the PAC-seq and RNA-seq methods.

(FIG. 12A) Principal Component Analysis of gene read count distributions. The majority of the variance is between PAC-seq and RNA-seq preparation methods at 79%. The remaining variance along the PC2 component, at 17%, was due to the effects of INTS11 knockdown compared to LacZ. (FIG. 12B and FIG. 12C) $Log_2$ fold change versus the P-adjusted value for the DE detected in PAC-seq and RNA-seq respectively. Genes that had a fold change greater than two and a P-adjusted value less than 0.05 have been colored red for those upregulated and blue for those downregulated upon INTS11 knockdown. (FIG. 12D) Comparison of $log_2$ fold change between methods. The $log_2$ fold change of genes that had an adjusted p-value <0.05 was highly correlated between methods with an $R_2$ value of 0.8961 and a slightly lower fold change detected by RNA-seq at 0.8933 of the value for PAC-seq.

DETAILED DESCRIPTION OF THE INVENTION

Figure 1A:
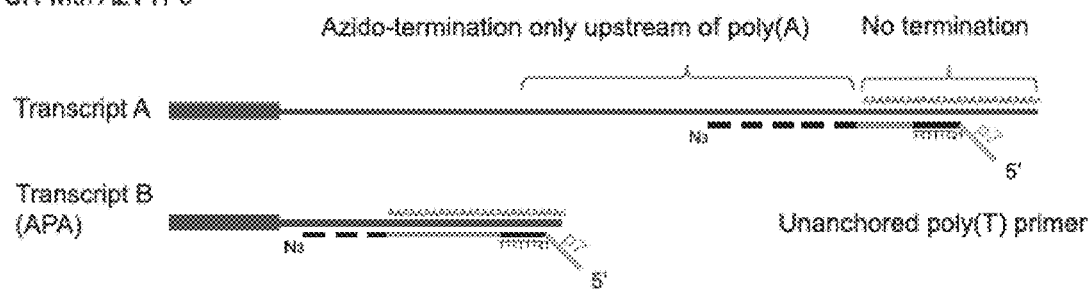
FIGS. 1A to 1G shows a schematic overview of Poly(A)-ClickSeq (PAC-seq) pipeline.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The recent emergence of alternative polyadenylation (APA) as an engine driving transcriptomic diversity has stimulated the development of sequencing methodologies designed to assess genome-wide polyadenylation events. The goal of these approaches is to enrich, partition, capture, and ultimately sequence poly(A) site junctions. However, these methods often require poly(A) enrichment, 3' linker ligation steps, and RNA fragmentation, which can necessitate higher levels of starting RNA, increase experimental error, and potentially introduce bias. The inventors recently reported a click-chemistry based method for generating RNAseq libraries called "ClickSeq".

Example 1. Novel Method to Direct the cDNA Synthesis Specifically Toward the 3'UTR/Poly(A) Tail Junction of Cellular RNA The inventors have developed a novel method to direct the cDNA synthesis specifically toward the 3'UTR/poly(A) tail junction of cellular RNA. With this novel approach, the inventors demonstrate sensitive and specific enrichment for poly(A) site junctions without the need for complex sample preparation, fragmentation or purification. Poly(A)-Click-Seq (PAC-seq) is therefore a simple procedure that generates high-quality RNA-seq poly(A) libraries. As a proof-of-principle, the inventors utilized PAC-seq to explore the poly(A) landscape of both human and *Drosophila* cells in culture and observed outstanding overlap with existing poly(A) databases and also identified previously unannotated poly(A) sites. Moreover, the inventors utilize PAC-seq to quantify and analyze APA events regulated by CFIm25 illustrating how this technology can be harnessed to identify alternatively polyadenylated RNA.

The novel method of the present invention has a number of advantages over other methodologies due to its simplicity, cost-effectiveness, and speed while providing high-quality, unbiased sequencing libraries. The approach is an alteration of an RNA-seq technique the inventors recently reported called 'ClickSeq'(42). For Poly(A)-ClickSeq (PAC-seq), small amounts of three 3'-azido-nucleotides (AzGTP, AzCTP and AzATP) are added to oligo-dT primed cDNA synthesis reactions yielding cDNA fragments that are stochastically terminated upstream of the 3'UTR/poly(A) junction, but not within the poly(A) tail. Subsequently, the azido-terminated cDNA can be purified, 'click-ligated' to an alkyne-functionalized 5' Illumina adaptor and an NGS library enriched with 3'UTR/poly(A) junctions is then created by standard PCR. The skilled artisan will recognize that other adaptors may be substituted for the 5' Illumina adaptor. As a demonstration of its applicability, the inventors use PAC-Seq to analyze total cellular RNA from HeLa cell extracts and demonstrate that this approach is robust and can thoroughly capture authentic pre-validated polyadenylated sites without the need for any sample purification, enrichment or fragmentation. Moreover, this can be achieved with a minimal number of extraneous sequence reads allowing for experiments with multiple replicates to be loaded even onto a single flowcell of an Illumina MiSeq. The inventors also analyzed multiple replicates of HeLa cells that have been depleted of CFIm25 to demonstrate the ability of PAC-seq to identify and quantify APA regulation. Finally, the inventors characterize the poly(A) site profile of *Drosophila* S2 cells in culture and found that depletion of fly orthologue of CFIm25 (CG3689) induces only a small number of APA changes, indicating that the role of CFIm25 in regulated *Drosophila* APA may not be as extensive in fly. Overall, the simplicity, cost-effectiveness and fast turnaround of PAC-Seq will allow investigation into a wide-range of complex samples that were previously either too uneconomical or intractable to analyze. PAC-Seq will also have novel applications in the rapid and sensitive detection of viral pathogens from crude patient specimens that also possess poly(A) tails, such as enteroviruses, alphaviruses and HIV.

Isolation of RNA from HeLa cells and siRNA knockdown of CFIm25. Parental HeLa cells were purchased from ATCC (Cat #CCL-2) and maintained in Eagle's Minimum Essential Medium (Lonza, Cat #12-604F) with 10% fetal bovine serum. The cells are transfected with three different siRNAs for CFIm25 (Sigma Aldrich, St. Louis, MO, ID: SASI_Hs01_00146875-77) and negative control siRNA (Sigma Aldrich, St. Louis, MO, ID:SIC002) using previously established approaches (43). Knockdown of CFIm25 was determined by Western blotting with anti-CFIm25 antibody (Proteintechlab, Rosemont, IL, Cat #10322-1-AP), GAPDH (Sigma, St. Louis, MO, G9545) served as a loading control. Total RNA was extracted using TRIzol Reagent (Life Technologies) using the manufacturers protocol.

Isolation of RNA from S2 cells and dsRNA knockdown of CFIm25. *Drosophila* S2 cells were cultured in Schneider's *Drosophila* media (GIBCO) supplemented with 10% FBS, 50 units/ml penicillin, and 50 µg/ml streptomycin at 28° C. To knockdown CFIm25 in S2 cells, an individual DNA fragment in exon 1 of CFIm25 308 bp in length was PCR amplified. Each primer used in the PCR contained a 5' T7 RNA polymerase binding site (GAATTAATACGACTCAC-TATAGGG (SEQ ID NO:1) followed by sequences specific for CFIm25 gene (Forward primer: +AGCGC TGGACAGAAAAGTGT (SEQ ID NO:2) and reverse primer: +CGCCTGGTTGGTGTACTTCT (SEQ ID NO:3)). The PCR products were purified and used as templates to produce dsRNA using T7 RNA polymerase (Ambion). The dsRNA products were ethanol-precipitated and resuspended in water. The dsRNAs were annealed by incubation at 65° C. for 30 min followed by slow cooling to room temperature. S2 cells were incubated with dsRNA for CFIm25 or negative control dsRNA for LacZ or for three days with three hits. Total RNA was extracted using TRIzol Reagent (Life Technologies) using the manufacturers protocol. For quantitative Real Time-PCR (qRT-PCR) the mRNA was reverse transcribed using MMLV-RT (Invitrogen) using the manufacturer's protocol to generate cDNA. The qRT-PCR reactions were performed using Stratagene MxPro3000P (Agilent Technologies) and SYBRGREEN (Fermentas). The forward primer AGGGCCTCAAGAGATTGCTA (SEQ ID NO:4) is in exon2 boundary of CFIm25 and the reverse primer ATCGTGTCCTCAACAATCCA (SEQ ID NO:5) is located in exon 3 of CFIm25. The *Drosophila* housekeeping gene ribosomal protein S17 (Rps17) served as an internal control.

Library Preparation. No additional purification or selection of total RNA is required as the RT primer selects for polyadenylated RNAs. 125 ng to 4 µg of total RNA was used to generate the Poly(A)-ClickSeq libraries as described in the main text of Routh et al. 2017 NAR. Reverse transcription was performed using standard protocols with the addition of spiked-in azido-nucleotides (AzVTPs). The reverse is also true, it is possible to spike with propargyl-NTPs (alkyne) during cDNA synthesis and pair it with an azido terminated adapter. Specifically, a 1:5 5 mM AzVTP:dNTP working solution was made by adding 10 µL of 10 mM dNTPs to 2 µL each of 10 mM AzATP, AzCTP, and AzGTP (no AzTTP) and water to a final volume of 20 µL. To begin, 4 µg RNA, 1 µL of mM AzVTP:dNTPs working solution, and 1 µL 50 µM 3'Illumina_4N_21T primer (GTGACTG-GAGTTCAGACGTGTGCTCTTCC-GATCTNNNNTTTTTTTTTTTTTTTTTTTT (SEQ ID NO:6)) were mixed in 13 µL total volume and was heated to 95° C. for 2 min to denature the RNA then snap cooled on ice, >1 min. (NB: This is a non-anchored poly-T primer.) Superscript III Reverse Transcriptase (Invitrogen), 5× Superscript First Strand Buffer, DTT, and RNase OUT (Invitrogen) was added for 20 µL total final volume and the reaction was incubated at 50° for 20 min, then 75° for 15 min. Room temperature incubation was avoided during mixing of components to avoid non-specific amplification. After cDNA synthesis, the template RNA was removed with the addition of 10U RNase H (NEB) incubated at 37° for 20 mins. Next, the azido-terminated cDNA was purified using the Zymo DNA Clean and Concentrator Kit (Cat #11-303C) and eluted with 10 µL of 50 mM HEPES pH 7.2.

Click-Reaction. The 'Click-Adapter' (5' Hexynyl-NNN-NAGATCGGAAGAGCGTCGTGTAGGGAAAGA-GTGTAGATCTCGGTGGTCGCCGTATCATT (SEQ ID NO:7)) was added onto the azido-terminated cDNA by copper-catalyzed alkyne-azide cycloaddition (CuAAC) (42). The NNNN can be replaced with $N_{0-12}$ as a click adapter, or the adapter comprises a unique sequence, which can be used for duplicate reads. The click-reaction was made by diluting all 10 µL of the azido-terminated cDNA in 20 µL 100% DMSO, 3 µL 5 µM Click-Adapter and catalyzing the reaction twice with 0.4 µL 50 mM Vitamin C and 2 µL 10 mM Cu-TBTA (Lumiprobe) for 30 min at room temperature. The clicked-linked cDNA was then purified on a Zymo DNA column.

PCR Amplification. The final PCR amplification appends the remaining Illumina adapters and the desired demultiplexing index. Reactions were set up with the following reaction components: 5 µL Click-ligated cDNA, 2.5 µL 5 µM Indexing primer (CAAGCAGAAGACGGCAT-ACGAGATnnnnnnGTGACTGGAGTTCAGACGTGT (SEQ ID NO:8), where nnnnnn is the sequence of the desired index), 2.5 µL 5 µM Short Universal Primer (AAT-GATACGGCGACCACCGAG (SEQ ID NO:9)), and 25 µL 2× One Taq Standard Buffer Master Mix for a final 50 µL reaction. The skilled artisan will recognize thet the NNNNN nucleotide sequence is an index sequence and can be replaced by other barcodes, indexes, or even random Ns. Optimized thermocycler conditions are as follows: 94° 4 min; 53° 30 sec; 68° 10 min; [94° 30 sec, 53° 30 sec, 68° 2 min]×20-22; 68° 5 min. Amplified PCR product was then run on a 2% precast agarose e-gel (Invitrogen, E-Gel Electrophoresis System) for 10 minutes and ~200-300 bp fragments (for 1×150 SE Illumina) or ~200-400 bp fragments (for 1×250 SE Illumina) were excised and cleaned using the Zymo Research Gel DNA Recovery Kit. Final yield of size selected cDNA library was quantified using a QuBit fluorimeter.

Sequencing. Libraries were pooled and sequenced using the manufacturer's standard operating procedures on either a HiSeq 1500 using a HiSeq Rapid SBS kit v2 obtaining 1×250 bp SE reads, or a MiSeq using a MiSeq Reagent Kit v2 (300 cycles) obtaining 1×250 bp SE reads. Raw data was de-multiplexed using TruSeq indexes using the CASAVA pipeline or MiSeq Reporter Software. All read data can be accessed through the GEO database (GSE94950).

Read Processing and Quality Filtering. All custom python scripts (as well as example batch recipes and instructions) used in the following read-processing steps are available in Datafile 1 of Routh et al. 2017 NAR, relevent Datafile incorporated herein by reference. Raw reads were trimmed to remove TruSeq adaptors and the first 6 nucleotides derived from the 'Click-Adaptor' using cutadapt (44); variables: -a nnnnagatcggaagagc-m 60 (nucleic acids 1-17 of SEQ ID NO:17). The inventors discarded reads shorter than 60 nucleotides as these would be too short to yield both a poly (A) tail as well as sufficient nucleotides to provide an unambiguous mapping. Next, cutadapt was used a second time to search for reads containing poly (A) tails at least 15 nts in length, allowing for one mismatch; variables: -b AAAAAAAAAAAAAAAA-n 2-O-m 40 (SEQ ID NO:10). Using a custom script (Datafile 1 of Routh et al. 2017 NAR, relevent Datafile incorporated herein by reference), the poly (A) tail length is extracted by comparing the de-adenylated reads to the pre-trimmed reads and this information is appended to the read name of the data file. The trimmed, de-adenylated reads were additionally quality filtered using the fastxtoolkit (hannonlab.cshl.edu/fastx_toolkit/) to ensure that >98% of the nucleotides in each read had a PHRED score greater than 20. This process yields single-end reads without poly (A) s at least 40 nts in length.

Datafile 1 of Routh et al. 2017 NAR, relevent Datafile incorporated herein by reference:

Compilation of Scripts for processing raw Poly (A)-ClickSeq data. All scripts have been successfully executed on Cygwin workstation and on Linux server using python version 2.7. Required software packages and the last confirmed working version are: HiSat2 v2.0.4 (2), samtools v1.2 (3), cutadapt v1.9.1 (4), fastx_toolkit v0.0.14 hannonlab.cshl.edu/fastx_toolkit/Different packages/versions may require adjustments.

Scripts include:
1) Extract_nts.py:
    Uses samtools(3) to extract nucleotide either before or after poly(A) sites provided in a BEDGraph in the format generated using the pAz-Seq scripts.
2) Extract_p_A Lens_Ad.py:
    Required during read processing to measure and extract poly(A) length in individual reads and append this information on to the read name
3) MakeBEDGRAPHpALenAr.py
    Required to make the BEDGraph from a mapped SAM file.
4) Mask_ints.py
    Required to remove mapped reads that are likely present due to non-specific/internal priming. Requires samtools(3)
5) Merge_Reps.py
    Allows merging of multiple BEDGraph files
6) Remove_5prime_IDtag.py
    Required during read processing to remove nucleotides derived from the 5' Click adaptor. Usually only six nucleotides. This can function as limited ID tag.

The following are examples of batch recipes that can be run locally on a stand-alone workstation. Adjustments must be made for (e.g.) SLURM queue submission on a server. Folder containing individual scripts must be in PATH, otherwise recipes must be adjusted to point to each script.

1) pAz_Prep.txt: processing raw reads
2) pAz_Map.txt: maps processed reads
3) pAz_BED.txt: generates BEDGraph files Read Mapping and poly(A) site annotation. The processed reads were mapped using the Hisat2(45) splice-aware aligner to the reference human genome (hg19) or *Drosophila melanogaster* (dm6) using the default mapping parameters, with the exception of disallowing soft-pads at the 3' end of the mapped read in order to prevent mis-annotation of the poly(A)site; variables: -sp 3,7. The position of the poly(A)

tails are given by the final nucleotide of the mapped reads. This locus, the number of mapped reads and the number of A's present in each mapped read are written to BEDGraph files of Routh et al. 2017 NAR, relevent scripts incorporated herein by reference). The BEDGraph contains an extra non-canonical entry comprising an data array whose coordinate (1-300) corresponds to poly(A) length and the value at that coordinate returns the number of reads that had that poly(A) length. This information allows us to apply a filter requiring each unique poly(A) tail to contain non-primer/non-templated A's as well as multiple mapping reads.

A range of values for this filter were tested requiring between 1 and 50 reads per event and requiring an average of between 1 and 10 non-templated A's (22 to 31 total As). The number of reads retained after this filter is illustrated in the heat map in FIG. 1E. The number of retained events drops quickly as a function of the number reads required plateauing at approximately N=5, and modestly as a function of poly(A) length. Therefore, the inventors filtered these sites requiring each site to have at least 5 mapped reads and the poly(A) tails to have at least 5 non-templated As per reads. These values can be further customised using the inventors' scripts. Finally, the base composition of 20 nts nucleotides from the reference genome downstream of the poly(A) sites were inspected using samtools (46) and custom scripts (Supplementary Data 1 of Routh et al. 2017 NAR, relevent data incorporated herein by reference). The frequency of nucleotides found in this regions are shown in FIGS. 1F and 1G. This revealed an abundance of sites that were predominantly As downstream of the poly(A) sites in the reference genome, and are therefore likely to be internally primed sites, rather than bona fide poly(A) tails. Additionally, T's were also found to be over-represent in these regions, consistent with the observation that U-rich tracts promote pre-mRNA cleavage (5). Therefore, only poly(A) sites containing 15 or fewer A's in these sequences were used for further analysis. BEDgraph files containing the poly(A) sites identified in this manuscript are available in Datafiles 2-4 of Routh et al. 2017 NAR, relevent Datafile incorporated herein by reference.

Datafile 2: BEDgraph files of HiSeq analysis of Wt HeLa and CFIm25 KD poly(A) sites, Human hg19. Individual BEDgraphs for each replicate (3×) for both wild-type and CF25Im KD cells are provided, as well as the merged datasets requiring a unique poly(A) site to be present in two or more replicates (as used in Routh et al. 2017 NAR, relevent Datafile incorporated herein by reference). Additionally, BEDgraphs of the coverage of reads over the reference genome found in Poly(A)-ClickSeq datasets are provided.

Datafile 3: BEDgraph files of MiSeq analysis of Wt HeLa and CFIm25 KD poly(A) sites, Human hg19. Individual BEDgraphs for each replicate (3×) for both wild-type and CF25Im KD cells are provided, as well as the merged datasets requiring a unique poly(A) site to be present in two or more replicates (as used in Routh et al. 2017 NAR, relevent Datafile incorporated herein by reference).

Datafile 4: BEDgraph files of MiSeq analysis of Wt S2 and CFIm25 KD poly(A) sites, *Drosophila* dm6. Individual BEDgraphs for each replicate (3×) for both wild-type and CF25Im KD cells are provided, as well as the merged datasets requiring a unique poly(A) site to be present in two or more replicates (as used in Routh et al. 2017 NAR). Additionally, BEDgraphs of the coverage of reads over the reference genome found in Poly(A)-ClickSeq datasets are provided.

For alternative poly-adenylation analysis, multiple poly(A) sites occurring within 10 nts of one another were clustered into a single site, with the frequency of the clustered site equaling the sum of the individual sites. Sites found within the terminal exon of genes annotated in the UCSC genome browser were extracted and compared between wild-type and CF25Im knock-down cell-lines. If multiple poly(A) sites were found within the terminal exon and if the relative usage of these was altered by greater than 10% between the wild-type and knock-down cell types then these poly(A) sites were deemed to be alternatively polyadenylated.

Motif Enrichment Analysis. The sequences from the reference genome either upstream or downstream of the poly(A) sites were extracted using samtools (46) and custom scripts (Supplementary Data 1 of Routh et al. 2017 NAR). Unique sequences were searched for RNA motif enrichment using the dreme (47) component of the MEME suite; variables: -rna -norc -mink 4-maxk 8. Following this analysis, the distribution probability of enriched motifs were determined using CentriMo (48); variables: --norc.

Poly(A)-ClickSeq Library Generation. The inventors developed a technique called 'ClickSeq' that uses azido-nucleotide terminators in randomly-primed RT reactions to produce cDNA fragments from non-fragmented template RNA (42). Azido-nucleotides are stochastically incorporated during cDNA synthesis inducing chain-termination yielding a distribution of cDNA fragment lengths, which is determined by the ratio of AzNTPs to dNTPs. As a result of chain termination, the cDNA fragments are blocked by an azido-group at their 3' end. Using copper-catalyzed azide-alkyne cycloaddition (CuAAC) (49), the inventors demonstrated that the inventors could 'click-ligate' 5'-hexynyl functionalized DNA oligos corresponding to the Illumina universal sequencing primer onto these 3'-azido-terminated fragments, generating unnatural triazole-linked ssDNA molecules. Importantly, these ssDNA templates are bio-compatible (50). Therefore, with a standard PCR reaction the inventors can amplify these fragments to generate high-quality Illumina sequencing libraries with even sequence coverage (51). Moreover, this approach provides many advantages over many over RNA-seq methodologies due to its simplicity, the removal of the fragmentation and ligation steps, and the reduction of artifactual RNA recombination (42).

Here, the inventors target sequencing to only the 3' ends of polyadenylated RNAs: "Poly(A)-ClickSeq"; or PAC-seq. For PAC-seq, rather than using a random primer, the inventors initiate reverse transcription using oligo(dT) primers without anchored Ts, or a non-T anchor. This primer also contains an overhang corresponding to a portion of the Illumina p7 adaptor (illustrated in FIG. 1A). By priming directly from poly(A) tails, the inventors can specifically reverse transcribe polyadenylated RNAs directly from crude RNA extracts without any prior sample purification,poly(A) enrichment or fragmentation. Moreover, by avoiding the use of a non-anchored oligo(dT) primer, in principle the primer can anneal anywhere with the poly(A) tail. Importantly, complementary cDNA transcripts will contain 'T's derived from the template as well as 21 'T's derived from the RT-primer. During computational read processing, this information is extracted and used to provide a quantitative assessment of mapping reliability and allow us to filter out mis-primed events that only have T's derived from the primer and none from a poly(A) tail (FIG. 1H). Importantly, the present invention provides an important quality control normally absent in other approaches that is used for validation of the final output data.

In 'ClickSeq', cDNA synthesis can terminate opposite any nucleotide. In PAC-seq, however, the critical innovation required to specifically sequence the junctions of RNA 3'UTRs and their poly(A) tails is to omit AzTTP from the reaction mixture (i.e. the inventors provide a mixture of AzVTPs and dNTPs). Without AzTTP present in the RT-PCR reaction mixture, reverse-transcription cannot terminate opposite an 'A' in the RNA template. Rather, reverse-transcription must continue until non-A residues are found (FIG. 1A). Therefore, cDNA synthesis is stochastically terminated at a distance upstream of the 3'UTR/poly(A) junction tailored by adjusting the ratio of AzVTPs to dNTPs. This design allows for cDNA chain termination to occur only in the residues just upstream of poly(A) tail, essentially 'homing-in' on the junction of the 3'UTR and the poly(A) tail. The inventors have found that a ratio of 1:5 AzVTPs: dNTPs reliably yields cDNA fragments ranging from 50-400 nts in length (42).

Figure 1B:
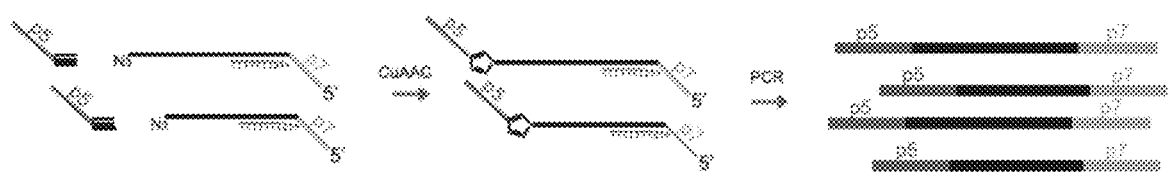
Figure 1C:
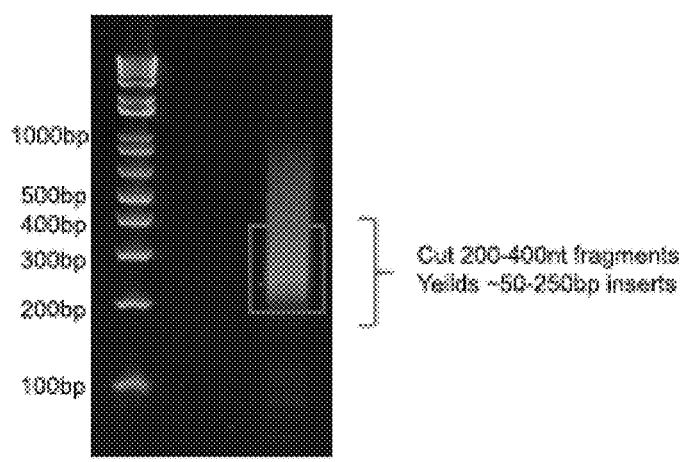
Figure 1D:
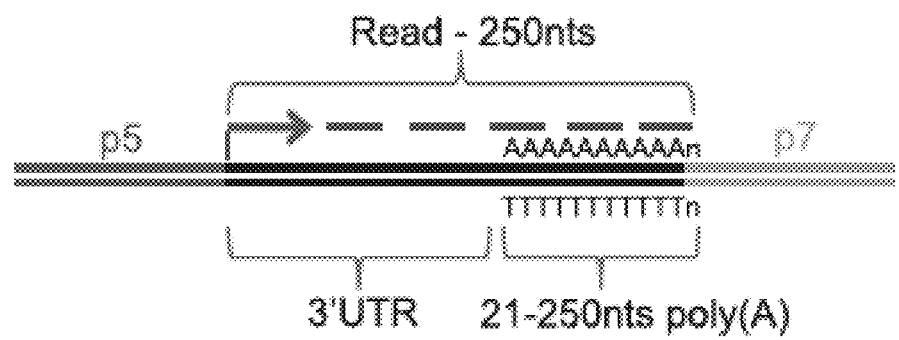

To finalize PAC-Seq libraries, the inventors purify the azido-terminated cDNA, 'click-ligate' the 5' Illumina adaptor, and then PCR amplify an NGS library containing the desired demultiplexing indices (FIG. 1B). The total size of all the adaptors including the oligo(dT) primer is 150 bp. Therefore, cutting cDNA fragments 200-400 nt in length will yield inserts 50-250 nts in length (FIG. 1C). Each of the cDNA fragments will therefore contain: the full Illumina p5 adaptor; cDNA corresponding to the 3'UTR of the RNA transcript, the length of which is determined by the stochastic termination of RT-PCR; the poly(A) tail; and finally the Illumina p7 indexing adaptor (FIG. 1D). For optimal yield of reads containing poly(A) tails, libraries must be carefully size selected depending upon the sequencing platform and length of reads sequenced. Sequencing is initiated from the p5 adaptor. Therefore, if fragments are too large and the cDNA insert is longer than the length of the sequencing read, the 3'UTR/poly(A) tail junction will not be reached.

Figure 2A:
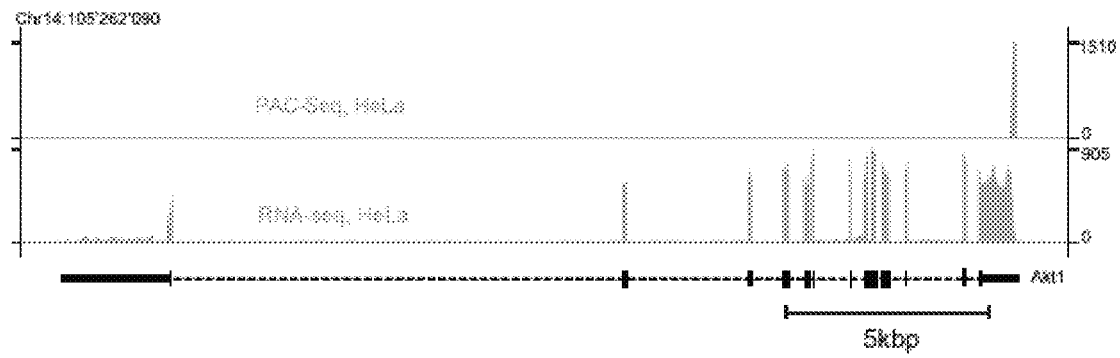
FIGS. 2A to 2H show examples of PAC-seq mapping data over mRNAs and comparison to RNAseq data. The positions of poly(A) sites were determined from PAC-seq analysis of wild-type and CF25Im knockdown HeLa cells. UCSC tracks are shown for the poly(A) Sites (data not shown), the coverage of the mapped PAC-seq reads. and from RNAseq analysis of HeLa cells from a previous analysis (69). Scale bars are indicated below each group of tracks (NB different scale).

Poly(A)-ClickSeq reveals the location and relative abundance of poly(A) sites. To test the approach for the mapping of poly(A) tails, the inventors performed 3 replicate PAC-Seq library preparations from total cellular RNA extracted from HeLa cells. HeLa cells have been well-characterized previously and provide a robust dataset against which to compare the mapping results. Final libraries were size-selected for fragment lengths up to 250 nts. This allows the detection of a wide range of poly(A) tail lengths. The three libraries were sequenced on a HiSeq 1500, yielding 26-36 Million raw reads per sample. These raw reads were processed as described in Methods of Routh et al. 2017 NAR. Greater than 46% of the raw demultiplexed read data were successfully processed using the pipeline, passing quality filters and containing poly(A) tails greater than 25 nts in length (Table 1). Therefore, the technique efficiently utilizes the data generated to find poly(A) tails. Using the splice-aware aligner, HiSat2 (45), 95-97% of the processed reads from each sample were successfully mapped to the human genome (hg19) (Table 1). An example of the mapped PAC-Seq reads to the human gene Akt1 is shown alongside previously obtained RNA-seq coverage data of HeLa cells (31) (FIG. 2A). This illustrates how the PAC-Seq data is concentrated at the 3' end of the RNA transcript. In contrast, the RNA-seq data is spread across the length of the mature mRNA.

TABLE 1

Mapping statistics for Poly(A)-ClickSeq of total cellular RNA from either wild-type or CFIm25 KD HeLa cells.

|  | Control |  | CFIm25 KD |  |
| --- | --- | --- | --- | --- |
| Total Raw Reads | 97532979 |  | 94717471 |  |
| Rep 1 | *35950672* |  | *36447774* |  |
| Rep 2 | *29912811* |  | *26317115* |  |
| Rep 3 | *31669496* |  | *31952582* |  |
| Number Processed Reads | 45565507 | 46.72% | 44291920 | 46.76% |
| Rep 1 | *16871383* | 46.93% | *17082420* | 46.87% |
| Rep 2 | *14097898* | 47.13% | *11819393* | 44.91% |
| Rep 3 | *14596226* | 46.09% | *15390107* | 48.17% |
| Reads Mapped to Human Genome | 44049869 | 96.67% | 42398266 | 95.72% |
| Rep 1 | *16326587* | 96.77% | *16372478* | 95.84% |
| Rep 2 | *13597357* | 96.45% | *11293094* | 95.55% |
| Rep 3 | *14125925* | 96.78% | *14732694* | 95.73% |
| Unmapped Reads | 1515638 | 3.33% | 1893654 | 4.28% |
| Rep 1 | *544796* | 3.23% | *709942* | 4.16% |
| Rep 2 | *500541* | 3.55% | *526299* | 4.45% |
| Rep 3 | *470301* | 3.22% | *657413* | 4.27% |
| Detected Poly(A) Sites | 37434 |  | 47811 |  |
| Rep 1 | *29544* |  | *50650* |  |
| Rep 2 | *24256* |  | *21346* |  |
| Rep 3 |  |  |  |  |
| Unique Poly(A) Sites found in one or more replicates | 56937 |  | 76176 |  |
| Unique Poly(A) Sites found in two or more replicates | 24937 |  | 33008 |  |
| Unique Poly(A) Sites found in all three replicates | 12501 |  | 13580 |  |

Figure 1E:
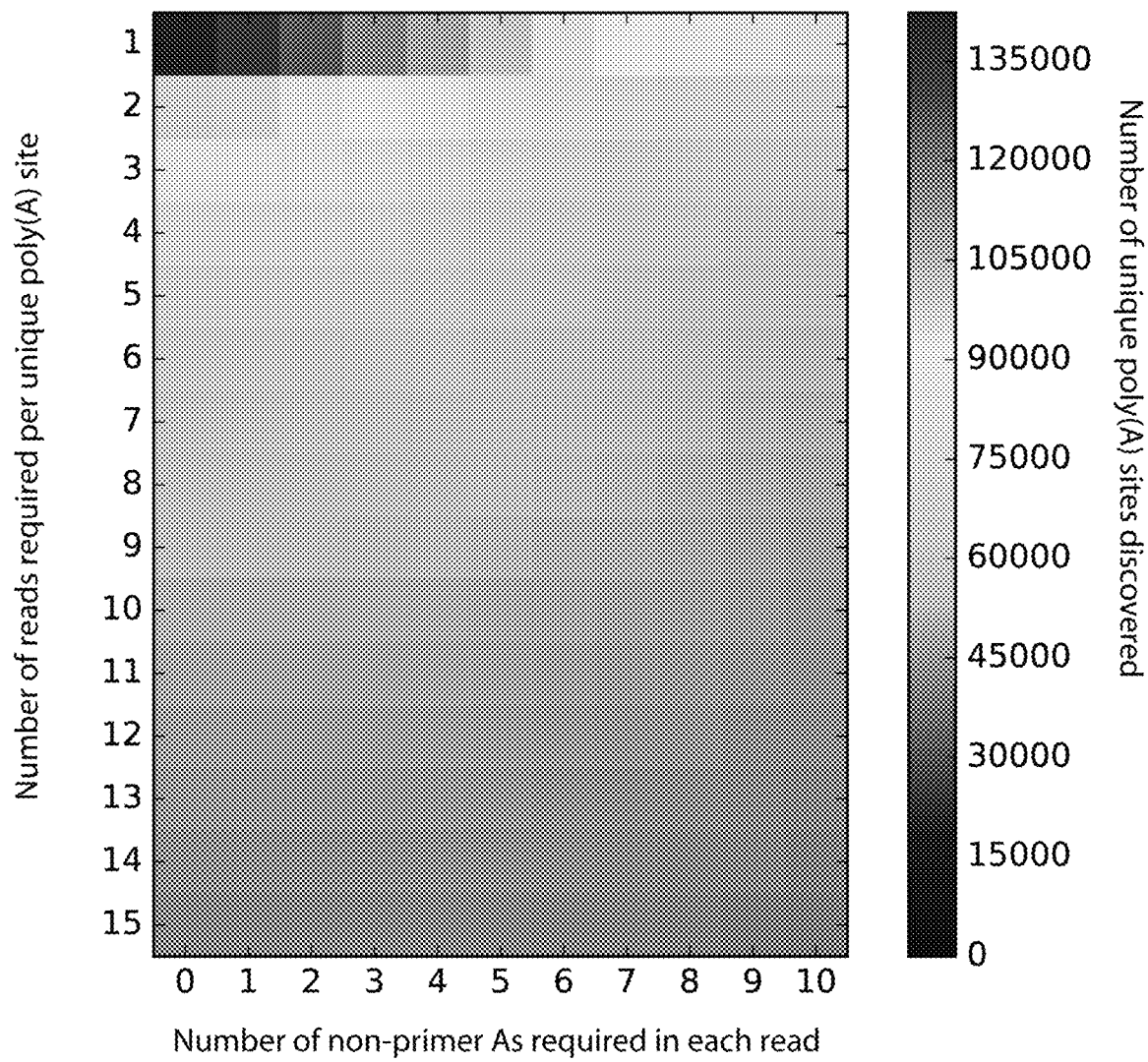
Figure 1F:
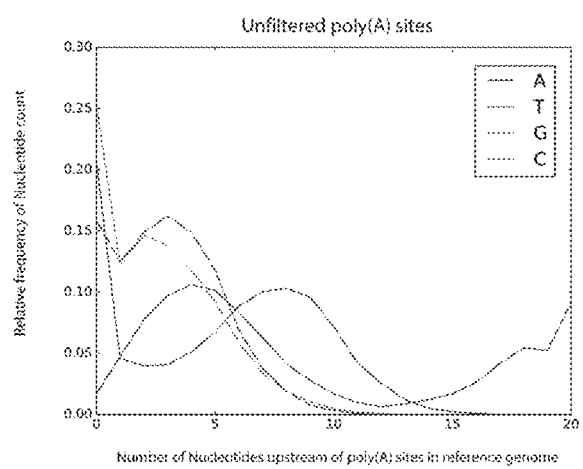
Figure 1G:
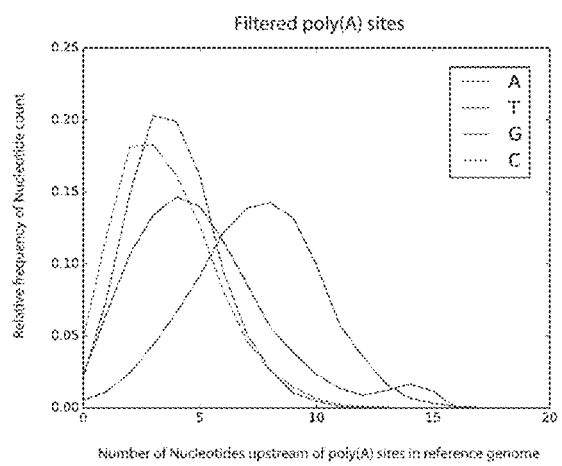
Figure 1H:
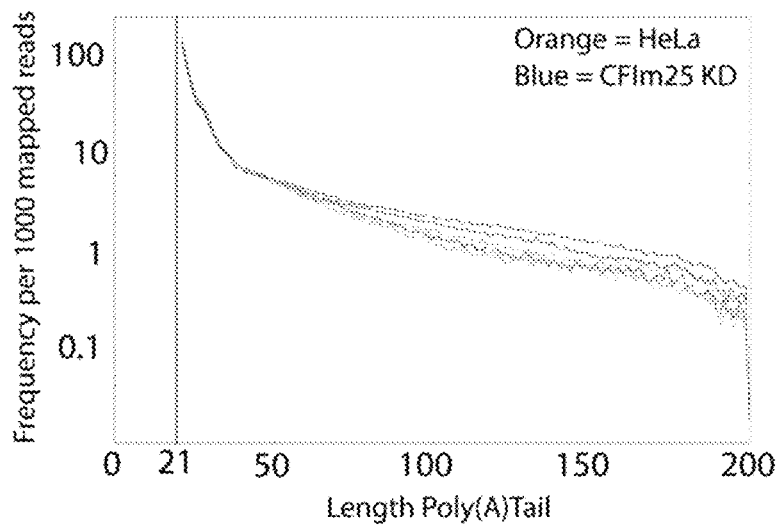
FIG. 1H shows poly(A) tail lengths inferred from the read data. The number of 'A's remaining at the end of each read after adaptor trimming is determined and appended onto the read name. After mapping, the distribution of poly(A) tail length at each mapped loci can be determined. The distribution of tail lengths over all the mapped reads for each of the HiSeq Poly(A)-ClickSeq datasets of HeLa total cellular RNA (orange) and CFIm25 KD total cellular RNA (blue) is shown. A range of poly(A) tail lengths from 21 up to 200 nts is found.

From the mapped data, the inventors can definitively determine the exact location of poly(A) tail addition. Moreover, as non-primer derived 'A's are found in the read data, the inventors can also determine the distribution of poly(A) tails lengths found among the reads mapping at each specific location. With this information, the inventors can filter the mapped reads requiring them to contain a user-defined number of 'A's as described in the Methods sections of Routh et al. 2017 NAR. The inventors found that by requiring five or more reads each with five or more non-primer derived 'A's removed a large number of poorly-populated and likely non-specific RT-PCR products (FIG. 1E). The broad distribution of poly(A) tail lengths found throughout all the mapped reads matches trends previously reported (41) (FIG. 1H).

Application of Poly(A)-ClickSeq to analyze Alternative Polyadenylation. The inventors sought to further validate the utility of PAC-seq by testing its ability to detect alternative polyadenylated sites. The inventors and others have previously demonstrated that CFIm25 is a critical factor in the regulation poly(A) selection in mRNAs (23,28,43). Knock-down of CFIm25 results in the broad shortening of multiple mRNAs targets genome-wide. Therefore, the inventors performed replicate CFIm25 siRNA knock-downs in HeLa cells (FIG. 2G, 2H), extracted total cellular RNA and prepared PAC-Seq libraries.

In total, the analysis yielded 56,937 putative poly(A) sites in the wild-type HeLa cells, and 76,176 sites in the CFIm25 KD cells (Table 1). By requiring sites to be found in at least two out of three replicates, the inventors found 24,937 and 33,008 sites respectively (Table 1). So while specificity is greatly increased by leveraging the replicate data, the sensitivity is also decreased—resulting in the loss of over 75,000 putative poly(A) sites. Therefore the choice, implementation and interpretation of the number of replicates required in such transcriptomic analyses must be carefully considered and balanced (53). As one of the possible applications of PAC-seq is to characterize and discover any putative or novel poly(A) sites, the inventors proceeded to analyze poly(A) sites found in two or more replicates in order to maximally utilize the data, while retaining a reasonable degree of confidence.

Figures 2B, 2C:
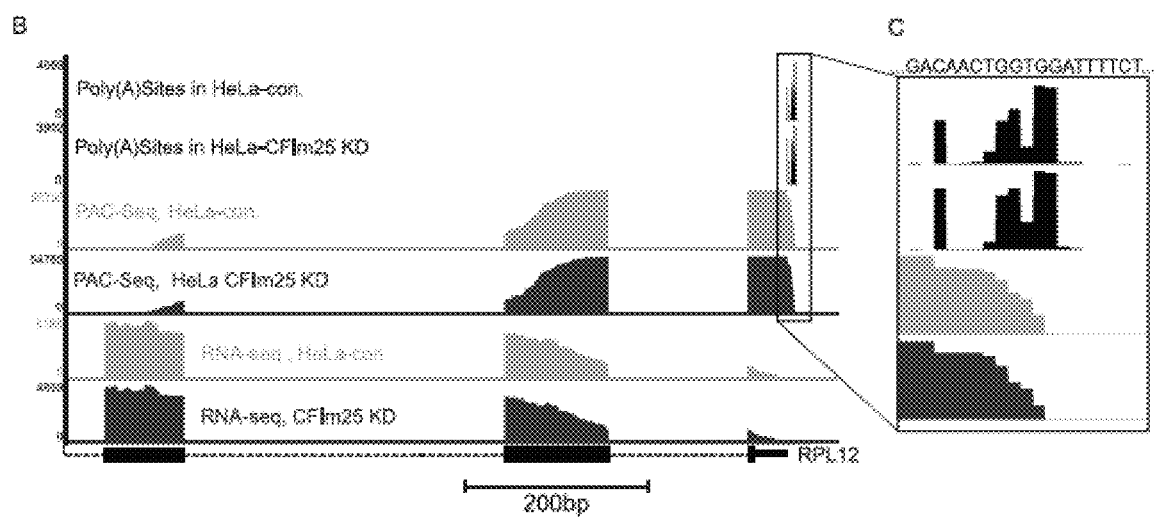
Figures 2D, 2E:
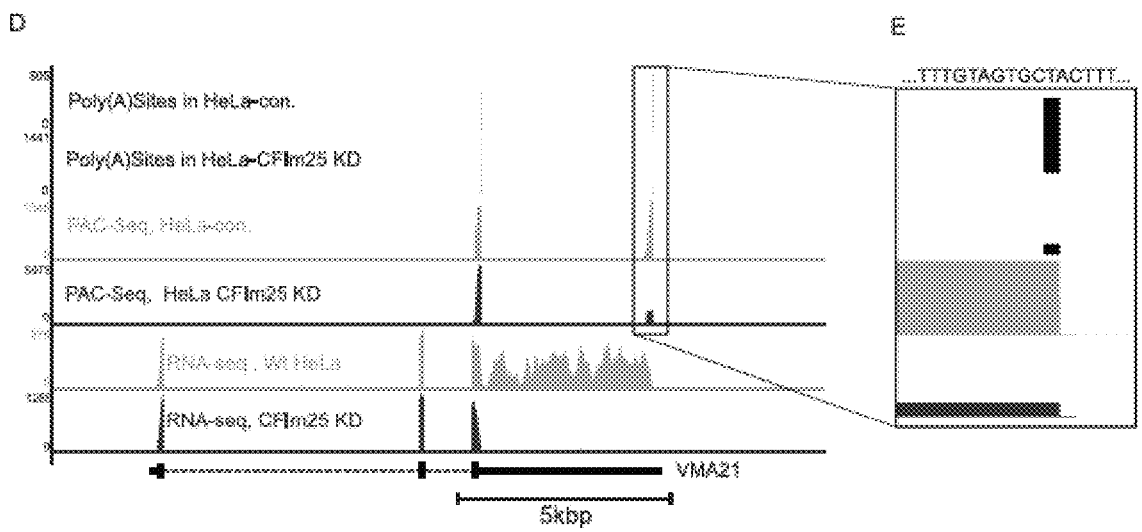
Figure 2F:
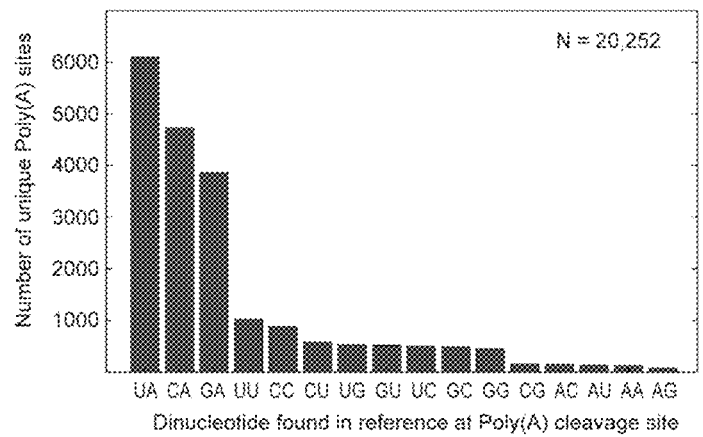
Figure 2G:
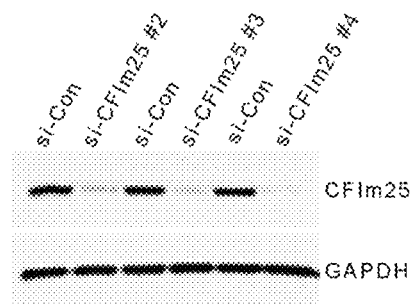

In the case of the highly expressed RPL12 gene that has not been found to undergo APA, the inventors can see that the exact identity of the 3'UTR/poly(A) tail junction can vary by approximately 10 nts in either dataset (FIGS. 2B and 2C). This may reflect a lack of specificity or degeneracy in the selection of the 3' cleavage site by the CPA. Nonetheless, the location of the poly(A) site found here agrees with the annotations from the UCSC database (54) as well as the anticipated poly(A) site determined from the mapping coverage in the RNA-seq data (33). Across all detected poly(A) sites, the inventors find that the dinucleotide cleavage site in the reference genome is highly enriched for CA, UA and GA (FIG. 2F), as has previously been observed (52). VMA21 has previously been identified as subject to CFIm25 regulation and that usage of the proximal poly(A) site (pPAS) is enriched in the CFIm25 KD cells (31). Indeed, the inventors observed similar results of reduced read density within the VMA 3'UTR upon CFIm25 KD and a clear switch from distal poly(A) site (dPAS) to pPAS usage when analyzed using PAC-seq (FIGS. 2D and 2E).

Figure 3A:
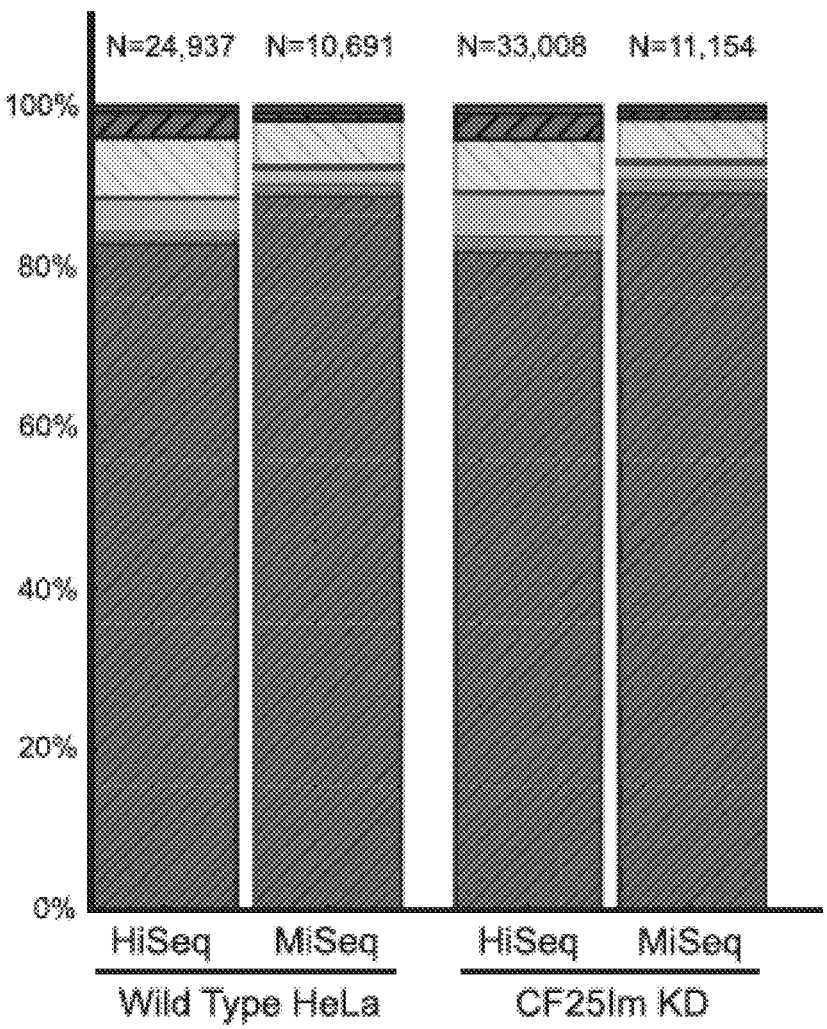
FIG. 3A to 3C show the characterization of poly(A) sites discovered by PAC-seq. A) Bar charts show the overlap of detected poly(A) sites with UCSC known gene annotations. Poly(A) sites were either found in known exons (Green), less than 500 nts upstream of known 3'UTR termini (Yellow), or in unannotated regions (Red). Comparisons between wild-type and CF25Im KD HeLa cell-lines are shown when analyzed either using a HiSeq or MiSeq. Scatter-plots comparing the poly(A) site frequencies found by HiSeq and MiSeq analysis for B) wild-type and C) CF25Im KD HeLa cell-lines. The number of sites in each category are indicated.

The majority of the detected polyadenylation events mapped to known genes in the UCSC database (~88.5%) and indeed the majority of these to annotated terminal exons as would be expected (Table 2 and FIG. 3A). A further 7.53% of the detected poly(A) sites mapped within 500 nts downstream of genes in UCSC database, indicating that a substantial number of poly(A) sites in fact can be found slightly downstream of the annotated mRNA termination sites. From the remaining 992 events (3.98%) not mapping over any known annotation, 791 of these were found to have the AWUAAA motif within 100 nts upstream of the detected poly(A) sites indicating that the PAC-seq dataset is locating novel and likely bona fide poly(A) sites bearing canonical regulatory elements. These trends are also quite similar in the CFIm25 KD dataset (Table 2 and FIG. 3A).

When compared to the poly(A) database (55), a total of 20,856 (83.6%) and 26,172 (79.3%) of the detected poly(A) sites for the wild-type and CFIm25 KD datasets respectively mapped over or within 10 nucleotides of the previously annotated sites (Table 2). Many of the unannotated poly(A) sites were found to map to mitochondrial genes, highly duplicated loci (e.g. GAGA antigen family) and transposons including LINEs (e.g. Tigger) and SINEs such as Alu elements, a large number of which were found within intronic sequences. A large number were also found to be likely uncharacterized pPASs or alternative terminal exons, not currently annotated in the poly(A) database.

TABLE 2

Locations of detected poly(A) site and comparison to Poly(A)DB in HiSeq dataset. Reads count are shown and poly(A) sites are shown in italics.

| Present in two+ replicates | 31752990 | | 30993891 | |
|---|---|---|---|---|
| | *24937* | | *33008* | |
| UCSC Genes | 29534658 | 93.01% | 28804998 | 92.94% |
| | *22066* | *88.49%* | *29434* | *89.17%* |

TABLE 2-continued

Locations of detected poly(A) site and comparison to Poly(A)DB in HiSeq dataset. Reads count are shown and poly(A) sites are shown in italics.

Of which:

| Exons | 28470681 | 89.66% | 27600003 | 89.05% |
|---|---|---|---|---|
| | *21002* | *84.22%* | *27605* | *83.63%* |
| 3' prime exon | 28182639 | 88.76% | 27314472 | 88.13% |
| | *20660* | *82.85%* | *26964* | *81.69%* |
| Within 500 nts down-stream of UCSC annotation | 1733592 | 5.46% | 1655001 | 5.34% |
| | *1879* | *7.53%* | *2188* | *6.63%* |
| Remaining | 484740 | 1.53% | 533892 | 1.72% |
| | *992* | *3.98%* | *1386* | *4.20%* |
| Poly(A)DB | 23207205 | 73.09% | 22466619 | 72.49% |
| | *14457* | *57.97%* | *26359* | *79.86%* |
| Poly(A)DB +/− 10 nts | 27658533 | 87.11% | 26305071 | 84.87% |
| | *20856* | *83.63%* | *26172* | *79.29%* |

Replicate sequencing using a MiSeq recapitulates the HiSeq results. PAC-Seq provides an efficient and inexpensive methodology for generating NGS libraries to be sequenced using HiSeq platforms. However, the cost of NGS still remains relatively high and is potentially prohibitive in the analysis of a large number of samples. To determine whether the inventors could obtain the same quality data, but by using a MiSeq platform, the inventors re-sequenced the HeLa cell libraries obtaining 1×250 bp reads. The inventors obtained 880K to 1.51M reads per dataset (Table 3), corresponding to 3.5% of the data obtained using the HiSeq. The inventors performed an identical analysis of poly(A) sites (requiring 5 reads to be mapped per poly(A) site, with 5 non-primer-derived A's, and in at least two replicates) and found a total of 10,691 poly(A) sites in the control-siRNA treated HeLa cells and 11,154 in the CFIm25 KD cells. The distribution of these sites were very similar to that found for the HiSeq data (FIG. 3A), with only a small increase in the proportion of poly(A) sites found in terminal exons being observed. This indicates that the less abundant poly(A) sites found only in the high-coverage HiSeq data are enriched for non-canonical poly(A) sites occurring at sites other that the terminal exon.

TABLE 3

Locations of detected poly(A) site and comparison to Poly(A)DB in MiSeq dataset. Reads shown and poly(A) sites shown in italics.

| Present in three replicates | 1279116 | 63.47% | 1361517 | 60.52% |
|---|---|---|---|---|
| | *10691* | | *11154* | |
| UCSC Genes | 1200186 | 93.83% | 1279629 | 93.99% |
| | *9877* | *92.39%* | *10370* | *92.97%* |

Of which:

| Exons | 1154973 | 90.29% | 1233759 | 90.62% |
|---|---|---|---|---|
| | *9637* | *90.14%* | *10110* | *90.64%* |
| 3' prime exon | 1146066 | 89.60% | 1223145 | 89.84% |
| | *9491* | *88.78%* | *9939* | *89.11%* |
| Within 500 nts down-stream of UCSC annotation | 64806 | 5.07% | 68211 | 5.01% |
| | *619* | *5.79%* | *601* | *5.39%* |
| Remaining | 14124 | 1.10% | 13677 | 1.00% |
| | *195* | *1.82%* | *183* | *1.64%* |
| Poly(A)DB | 960018 | 75.05% | 1015152 | 74.56% |
| | *7047* | *65.92%* | *7209* | *64.63%* |
| Poly(A)DB +/− 10 nts | 1119714 | 87.54% | 1188249 | 87.27% |
| | *9660* | *90.36%* | *9997* | *89.63%* |

Figure 3B:
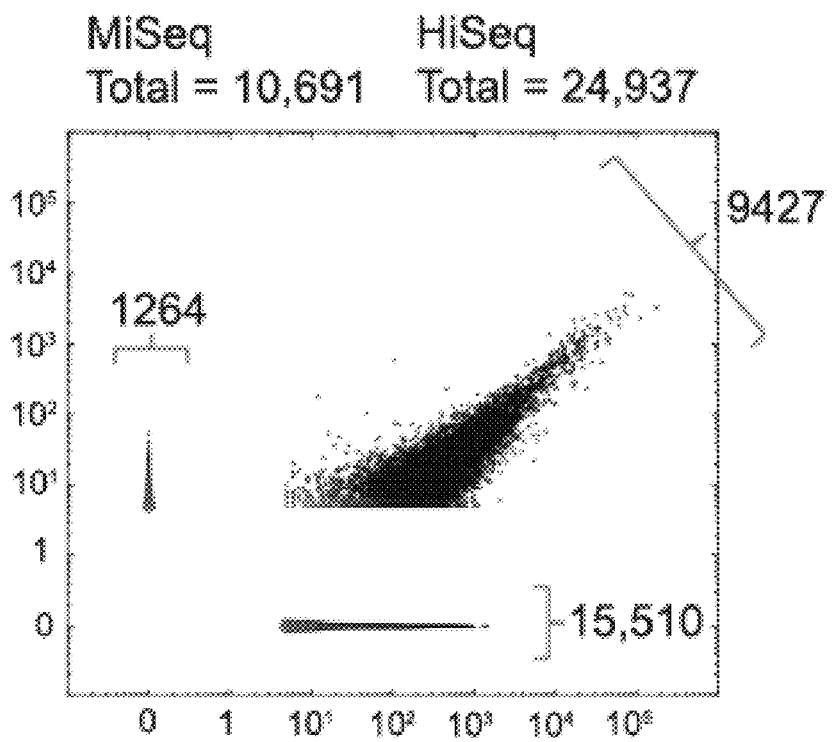
Figure 3C:
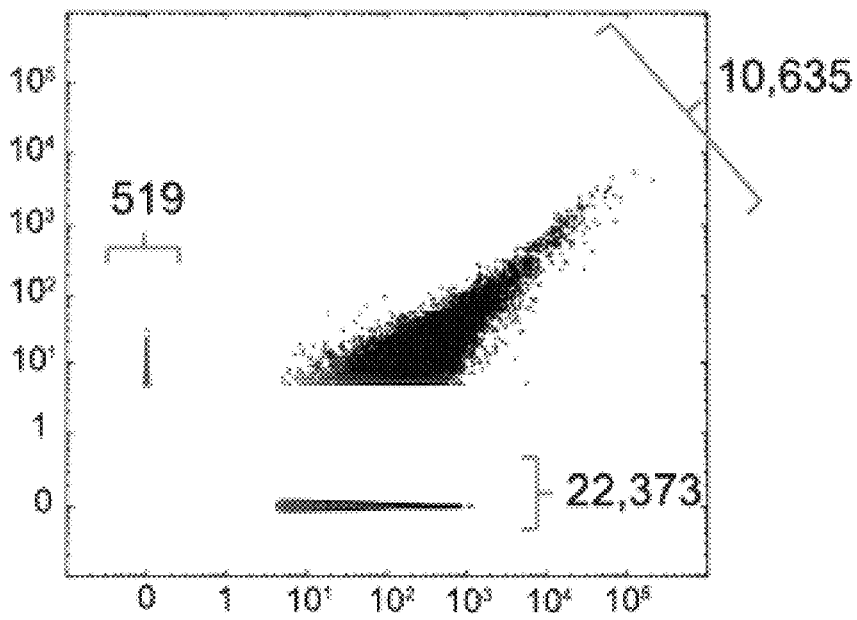

Calculating the Pearson Correlation coefficient between the HiSeq and MiSeq datasets for the frequencies of mapped reads at each unique poly(A) site returns R values of 0.89 for wild-type HeLa cell and 0.89 for the CFIm25 KD cells. Moreover, as can be seen in the scatter plots in FIG. 3B and FIG. 3C, the events that were either discovered in the MiSeq but not the HiSeq dataset (and vice versa) were the least abundant reads. This demonstrates that the inventors are retaining a large portion of the high-confidence, high-abundance poly(A) sites, despite only mapping 5% the number of processed reads. Therefore, the MiSeq is still sufficient to reproducibly capture the majority of poly(A) events and will therefore be suitable in a broad range of applications, despite the compromise in high-throughput, in a much more cost-effective manner.

Figure 4A:
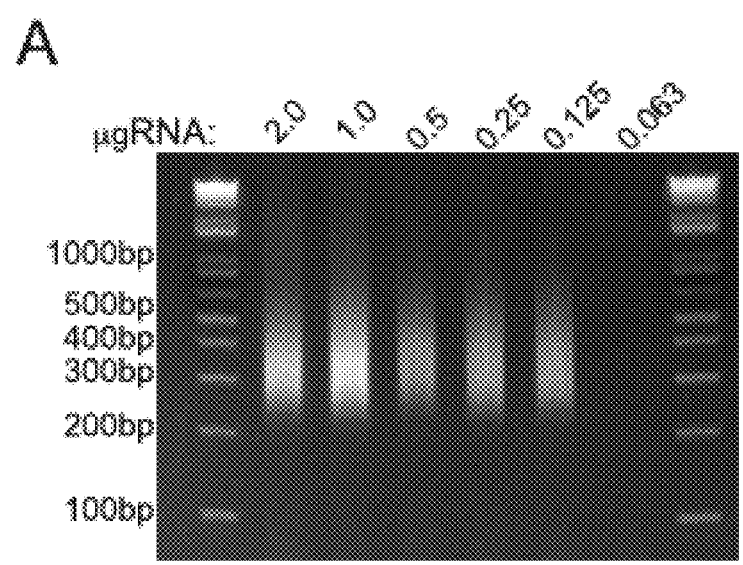
FIGS. 4A-C: Determination of PAC-seq sensitivity. A) Agarose gel image of PAC-seq libraries following PCR amplification. The amount of input total RNA for cDNA generation is labeled. B) Scatterplot analysis of the frequency of PASs identified by PAC-seq from the five libraries shown in panel A. In all cases, an individual library is compared to a "standard" library created from 2 ug of total RNA. The Pearson correlation coefficient is indicated for all blots. C) Representative genome browser screenshot of the 3' region of the TIMP2 gene. The five tracks in yellow are from PAC-seq while the lower track in red was generated using the previously published polyA_DB database (55).

Determination of PAC-seq sensitivity. In many cases, the amount of total RNA extracted from a sample can be limiting. For example, in the case of patient isolates or through the dissection of specific tissue types from animal models the amount of RNA can be well below 1ug making it essential that sequencing technology possess a high degree of sensitivity. To determine the minimal amount of RNA required for a successful PAC-seq analysis and to assess the impact of reduced input RNA on the number of PASs identified, the inventors utilized decreasing amounts of total RNA isolated from HeLa cells to generate PAC-seq libraries. The inventors chose the high end the dilution series to be 2 μg given that this is a typical amount retrieved from cell line-based experimentation and then proceeded to dilute this amount using 2-fold increments down to ~60 ng. All cDNA samples generated were amplified using the same cycle of PCR in order to minimize PCR duplication events and provide an even comparison. The inventors observed that PAC-seq libraries could be easily visualized at all levels of input RNA with the exception of the 60 ng sample (FIG. 4A). Interestingly, the inventors did not observe a completely linear relationship with respect to the intensity of the library produced versus the amount of total RNA used. Rather, the inventors found that both the 2 μg and 1 μg input generated relatively equal amounts of libraries while the 500 ng, 250 ng, and 125 ng were less robust but still relatively similar.

Figure 4B:
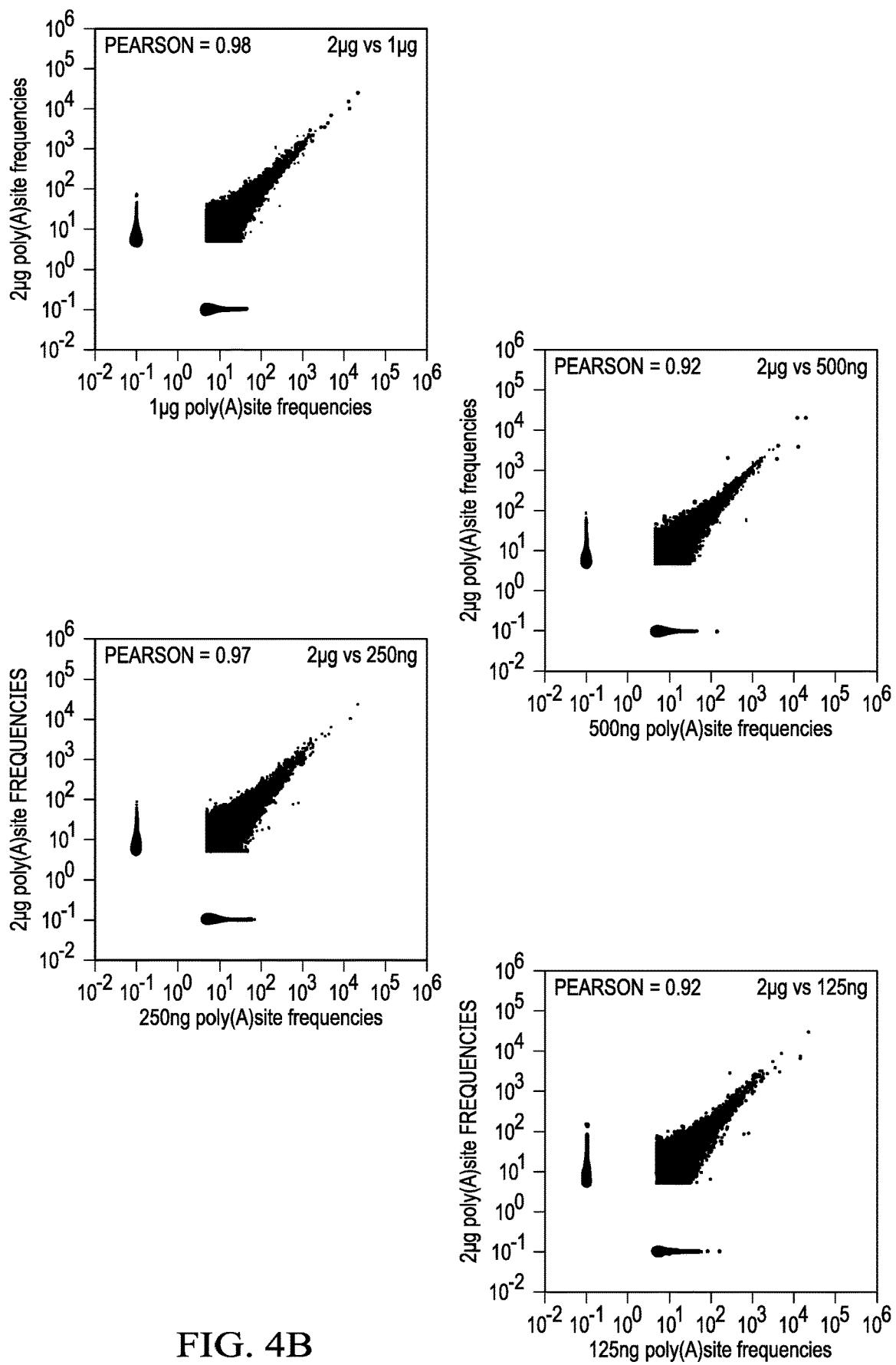
Figure 4C:
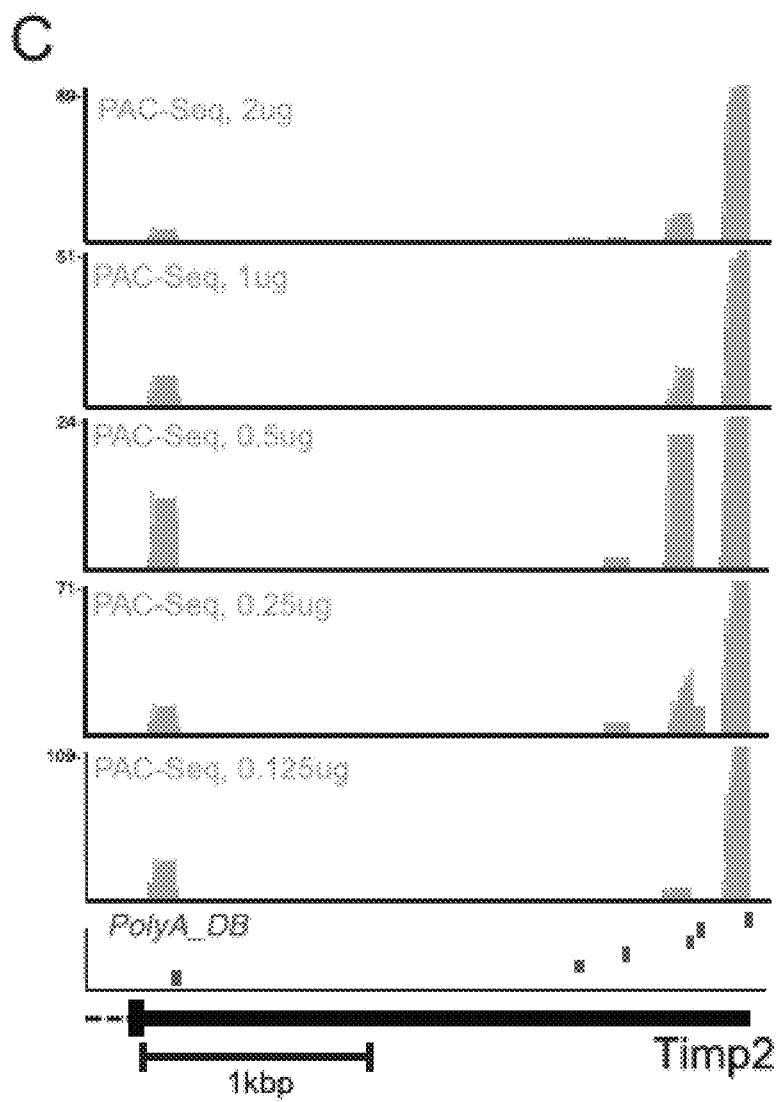

The inventors subjected the five libraries to sequencing using the MiSeq platform. Raw read files were trimmed to the same depth (2.9M reads) to allow cross-comparison, and then processed and mapped according to same protocols as used above (Table 4). To assess overall concordance, the inventors conducted four pairwise comparisons of each library with respect to the number of identified PASs (PAS frequencies) and in each case, the inventors chose the 2 μg library to be the "standard". Overall, the inventors observed strong concordance of each library compared to the standard with Pearson correlation coefficients ranging from 0.92-0.98 (FIG. 4B). As a representative example of the similarity between libraries, the inventors generated a genome-browser track for the PAC-seq reads at the 3' end of the TIMP2 gene (FIG. 4C), which has been shown by the inventors and others to have multiple PASs and to utilize predominantly the distal PAS in HeLa cells (23,43). All five libraries generated a highly similar profile of PAC-seq reads that not only confirm the preferred use of the distal PAS but are also in complete agreement with the polyA-database (PolyA_DB) as to the number and position of the six annotated PASs for TIMP2 (55). As a final point, the inventors determined that the reduction in the input RNA actually resulted in a slightly higher number of total (and novel) PASs identified (Table 4). This trend, which was apparent at each dilution tested, was not expected and the inventors speculate that reduced input RNA dilutes out competitor RNA molecules (e.g. rRNA) that could have a tendency to titrate RT reagents from bona fide mRNA 3' ends. Regardless, these results clearly demonstrate the level of sensitivity of PAC-seq and that reducing the level of input RNA does not appear to significantly alter the quality of the data nor its overall coverage of PASs.

TABLE 4

Number of poly (A) sites found in HeLa total cellular RNA when using different amounts of starting RNA for PAC-Seq. Each dataset was trimmed to 2.9M raw reads and processed to reveal unique poly (A) sites.

|  | 2 ug | 1 ug | 500 ng | 250 ng | 125 ng |
|---|---|---|---|---|---|
| Total Raw Reads | 3390216 | 4242083 | 2922931 | 3756427 | 4992222 |
| Filtered Raw reads to 2.9M | 2900000 | 2900000 | 2900000 | 2900000 | 2900000 |
| Processed Reads | 812697 | 901284 | 839255 | 949871 | 1027260 |
| Mapped to hg19 | 784504 | 868724 | 810782 | 913978 | 990302 |
| Unique poly (A) Sites >5 counts | *13058* | *14926* | *13682* | *15403* | *16470* |
| Unmapped | 28193 | 32560 | 28473 | 35893 | 36958 |
| Pearson to 2 ug | — | 0.98 | 0.92 | 0.97 | 0.92 |
| Pearson to 125 ng | 0.92 | 0.95 | 0.87 | 0.97 | — |

Poly(A) site choice is promoted by CFIm25 in a UGUA-dependent manner. CFIm25 has previously been implicated in the regulation of the poly(A) cleavage site selection but the mechanism is poorly understood. CFIm25 has been shown to have a preference for UGUA motifs (56) and proximal poly(A) sites have been found to contain elements that do not adhere to consensus as closely as distal poly(A) site motifs do (57). Given that PAC-seq provides an exact polyadenylation site, the inventors decided to explore the relationship of these sequence elements in the datasets. By comparing the control-siRNA treated and CFIm25 knock-down cell-lines, the inventors find a greater number of total poly(A) sites upon CFIm25 KD, despite the fact that the inventors obtained fractionally fewer reads in these datasets (Table 2). Moreover, while a slightly higher percentage of poly(A) sites are found in annotated genes (88.5% vs. 89.2%), a slightly smaller percentage of these are found in the terminal exon (82.9% vs. 81.7%). Similarly, a smaller proportion of the poly(A) sites in the CFIm25 KD cells overlap with previously annotated sites in the poly(A) database. Together, these trends may reflect a general role for CFIm25 in specifying the correct PAS (e.g. most consensus) and that a broader range of non-canonical sites become permissive upon CFIm25 knockdown. This hypothesis was explored further.

Figure 5A:
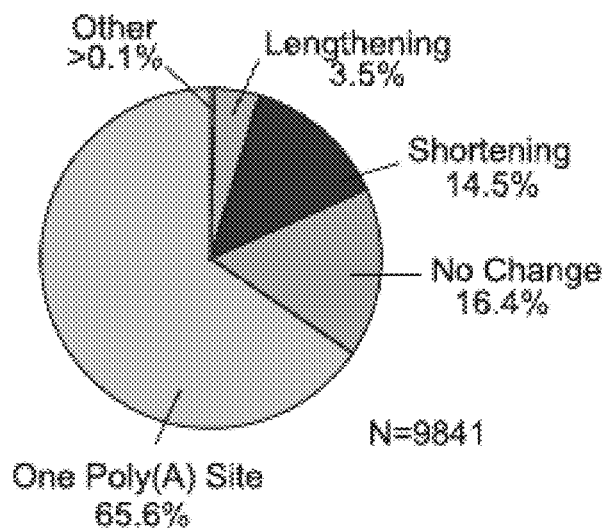
FIGS. 5A-J: Alternative poly-adenylation upon CF25Im knock-down. The poly(A) sites found in wild-type and CF25Im KD HeLa cells lines were compared and revealed whether mRNAs had one or multiple poly(A) sites within annotated terminal exons, and whether CF25Im knock-down resulted in the lengthening of shortening mRNA transcripts. Frequency of poly(A) sites in these categories are shown in A). B) Motif enrichment analysis using the MEME suite revealed that AWUAAA and UGUA motifs were enriched upstream of both proximal (pPAS) and distal (dPAS) poly (A) sites. Centrimo analysis showed that AWUAAA was found 20-40 nucleotides upstream of PASs while UGUA was dispersed. C) Poly(A) site and coverage tracks are shown for an example of a gene (ELAVL1, Human Antigen R) exhibiting 3'UTR shortening upon CF25Im KD. D) The frequency of AWUAAA and UGUA motifs found within 100 nt upstream of both proximal (pPAS) and distal (dPAS) poly(A) sites only for shortened mRNAs are shown. E) Poly(A) site and coverage tracks are shown for an example of a gene (ZNF467, Zinc Finger Protein 467) exhibiting 3'UTR lengthening upon CF25Im KD. F) The frequency of AWUAAA and UGUA motifs found within 100 nt upstream of either proximal (pPAS) and distal (dPAS) poly(A) sites only for lengthened mRNAs are shown.
Figure 5B:
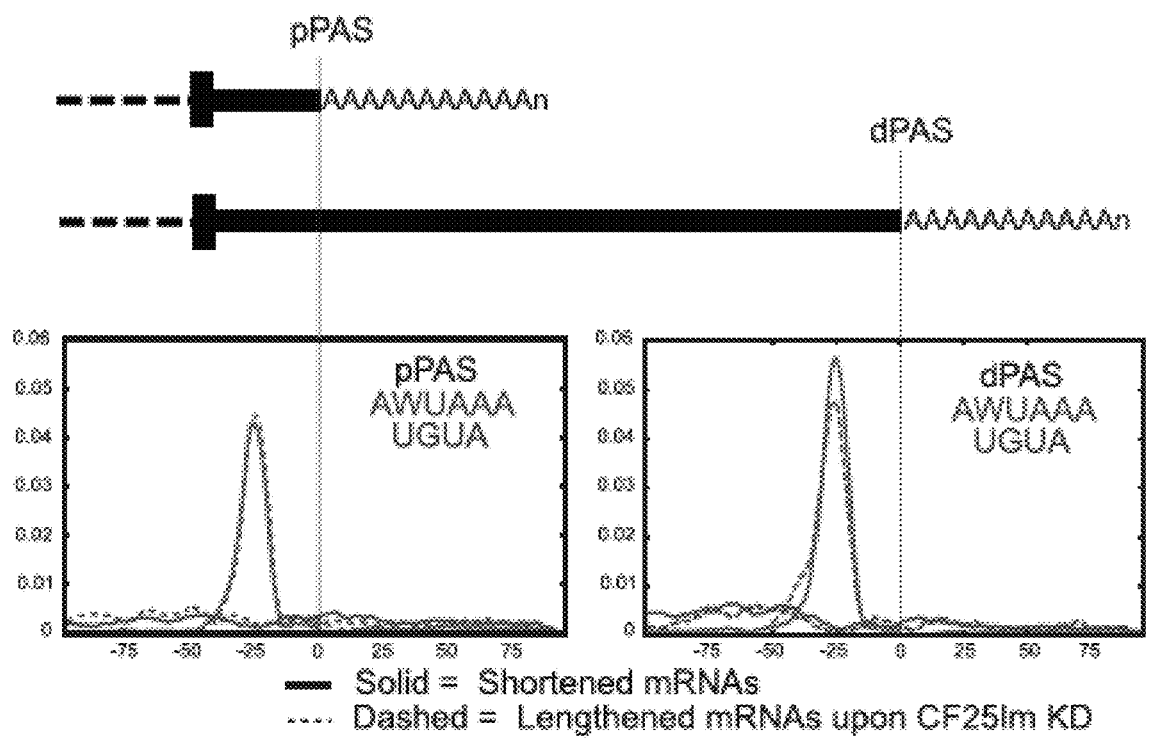
Figure 5C:
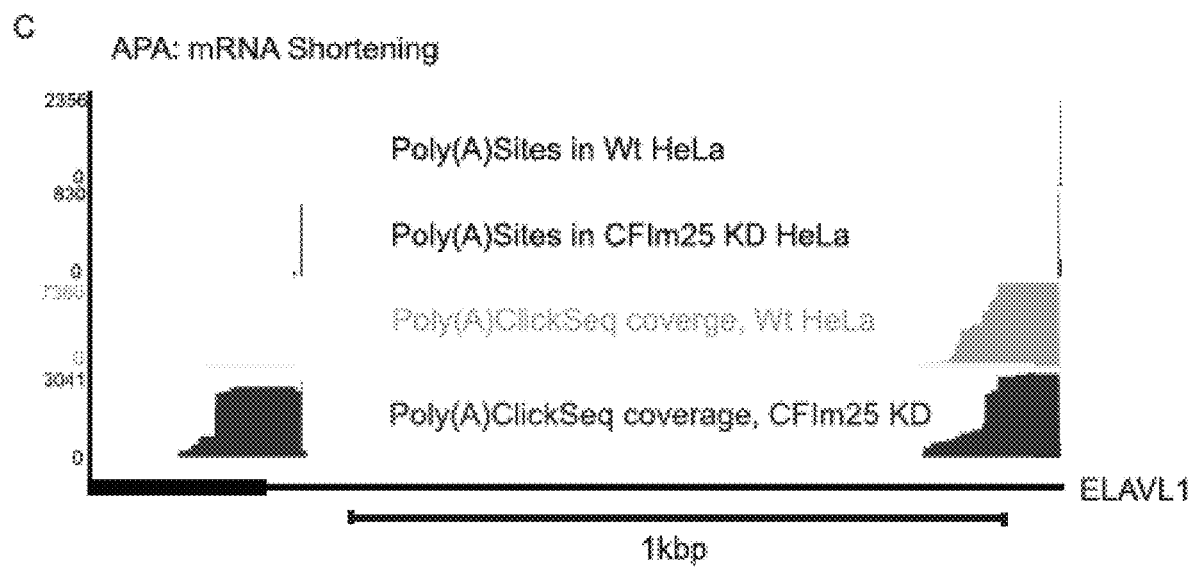
Figure 5D:
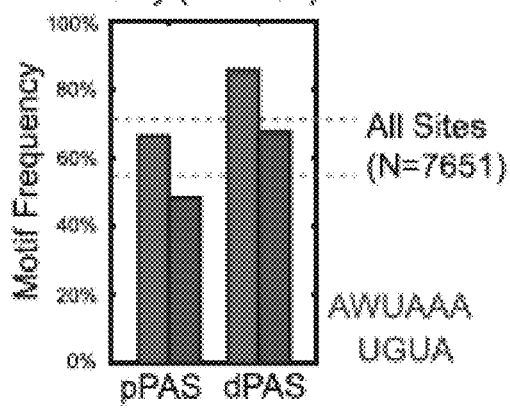
Figure 5E:
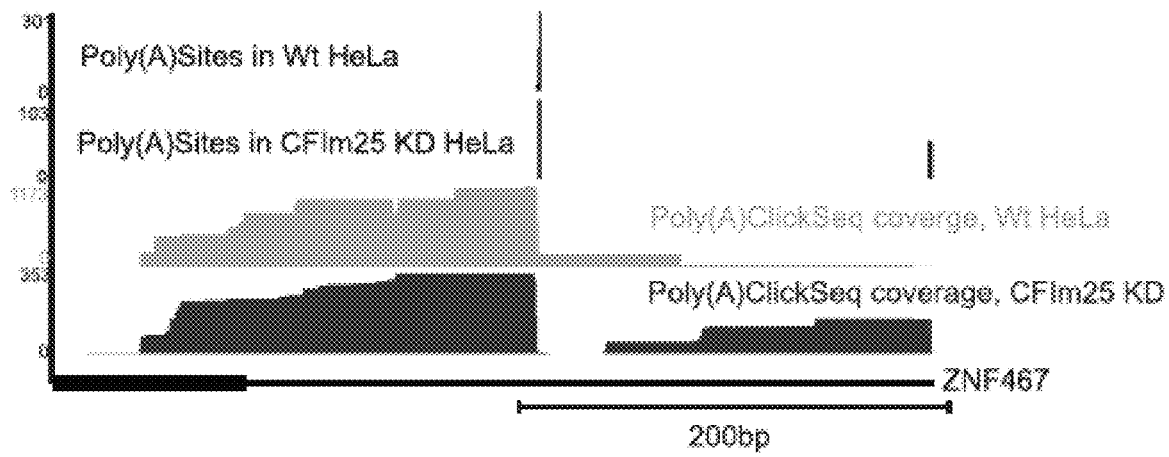

The inventors first clustered detected poly(A) site in the datasets so that two or more sites found within 10 nts of one another were considered to be same poly(A) site. Next, using the UCSC knowngene annotations (54), the inventors considered only poly(A) sites that were found in the terminal exons. For the HeLa cells, from a total of 9841 individual mRNAs, the inventors found 3388 mRNAs with two or more poly(A) sites containing a total of 7651 unique poly(A) sites (FIG. 5A). 1776 mRNAs were determined to exhibit significant (greater than 20% change) APA upon CFIm25 KD. Of these mRNAs, 1430 exhibited 3' UTR shortening (FIG. 5C) and 346 exhibited 3' UTR lengthening (FIG. 5E). The large number of shortened genes is highly consistent with previous studies by us and others.

The differential usage of 3' poly(A) cleavage sites is poly-factorial, but has been demonstrated to be promoted by the presence of at least two PAS motifs: AWUAAA and UGUA (4). DREW analysis (47) of these sites confirmed that these motifs were significantly enriched in the regions upstream of the detected poly(A) sites. To determine whether the choice of poly(A) cleavage site was altered by CFIm25 in a manner dependent upon these motifs, the inventors quantified the number of poly(A) sites containing AWUAAA and UGUA motifs <100 nts upstream. For all 7651 sites, the inventors found that 71.9% and 56.0% contained AWUAAA and motif UGUA motifs respectively. Using CentriMo (48), the inventors found that the AWUAAA motifs are strongly enriched between 20 and 40 nts preceding the PAS, but that UGUA motifs show little positional preference (FIG. 5B). This was true for both proximal and distal sites, regardless of whether CFIm25 KD induced lengthening or shortening of 3'UTRs.

Figure 5F:
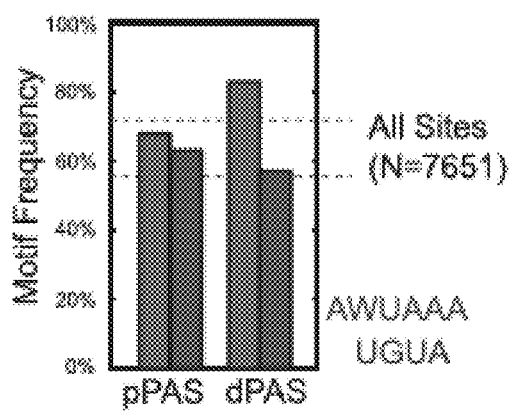
Figure 5G:
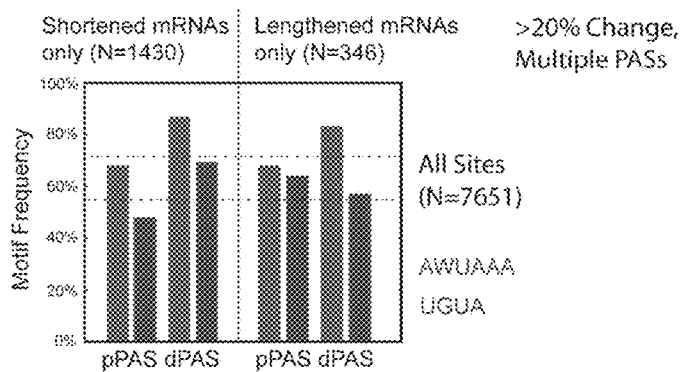
Figure 5H:
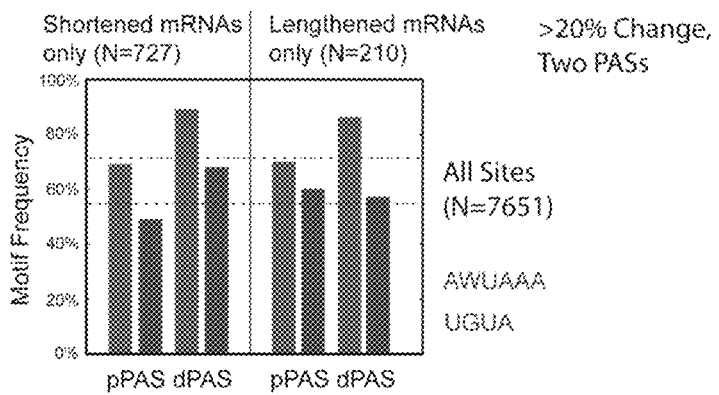
Figure 5I:
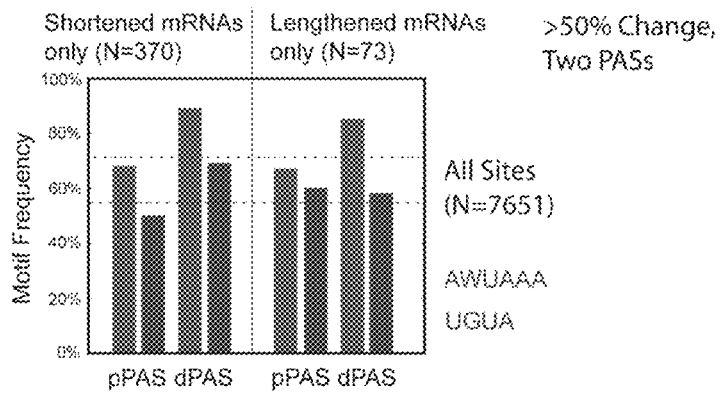
Figure 5J:
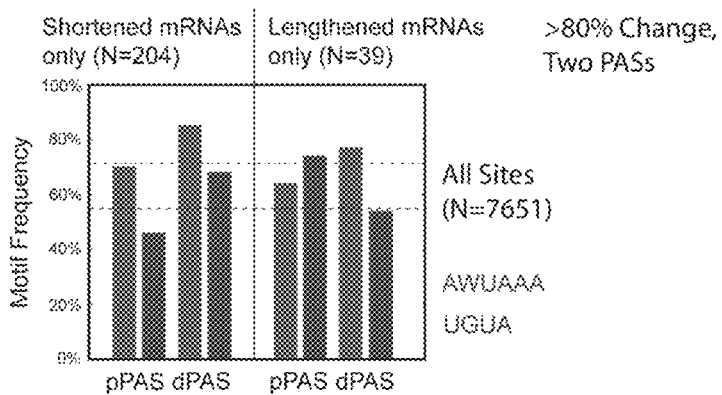

To investigate why most mRNAs exhibited 3'UTR shortening while a small group of others presented lengthening in response to CFIm25 knock down, the inventors analyzed the frequency of the AWUAAA and UGUA motifs found upstream of both the proximal (pPAS) and distal (dPAS) poly(A) sites for both lengthened and shortened mRNAs. The inventors find that distal sites are relatively enriched for AWUAAA motifs (>80%) regardless of whether CFIm25 KD induced lengthened or shortened 3'UTRs (FIGS. 5B, 5D and 5F). Interestingly however, the inventors observe a different trend for UGUA whereby UGUA motifs are enriched in the distal sites of mRNAs that are shortened after CFIm25 KD, but enriched in the proximal sites of mRNAs are lengthened after CFIm25 KD. This implies that selection of these poly(A) sites are promoted by CFIm25 in a UGUA-dependent manner and that this enhancement was lost upon CFIm25 KD resulting in an increase in the expression of less optimal alternative poly(A) sites. If the UGUA site is more prevalent in the distal position, then knockdown of CFIm25 reduces the utilization of this site and so the mRNAs are shortened. Conversely, if the UGUA site was found in the proximal position then that mRNA is lengthened. These trends were conserved when only considering mRNAs with only 2 PASs and at >20%, >50% and >80% APA strength (FIGS. 6A to 6D). Collectively, these results exemplify how PAC-seq datasets can be leveraged using motif analysis tools and provide additional insight into how CFIm25 is regulating poly(A) site choice.

Figure 2H:
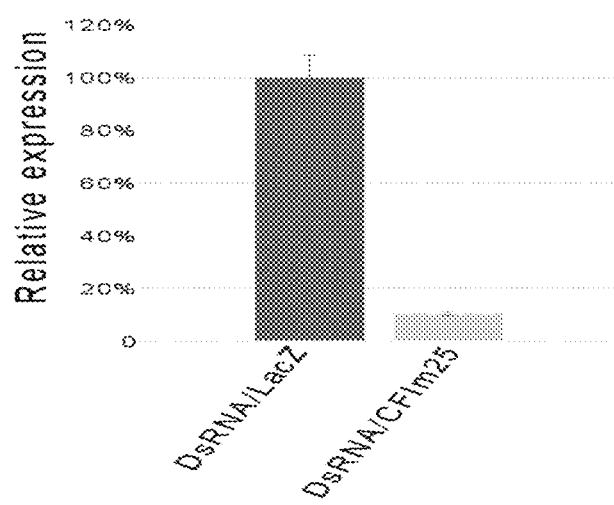

Poly(A)-ClickSeq analysis of Drosophila S2 cells. The inventors sought to further determine to what extent CFIm25 regulation of alternative polyadenylation is conserved in invertebrate species and how effective PAC-seq is in the analysis of a novel RNA dataset. Using dsRNA targeting the Drosophila orthologue of CFIm25 (CG3689), the inventors knocked down CFIm25 in S2 cells to a degree exceeding 90% (FIG. 2H). This level of knockdown in mammalian cells is sufficient to trigger genome-wide 3'UTR shortening in human cells and, in the inventors' experience, is sufficient to mediate a spectrum of loss of function phenotypes in S2 cells (58-62). Total cellular RNA from both mock-treated cells and CFIm25 KD cells was harvested in triplicate and used to generate PAC-Seq libraries using the same procedures as those described above. Libraries were sequenced on a MiSeq obtaining a total of 2.39M and 3.09M total processed reads, on average, for mock and CFIm25 KD S2 cells. Using the same mapping parameters as above (requiring 5 reads with poly(A) tails 25 nts of longer to be found in at least two of the three replicates) the inventors found 6910 poly(A) sites in the mock cells and 7473 in CFIm25 KD cells (Table 5). Similar to HeLa cells, these poly(A) sites are primarily found at the terminal exons of annotated genes (79.1% and 79.2%) (Table 5 and FIG. 6A). The inventors compared the dataset with the poly(A) sites reported in a previous analysis (63) and determined that 62.0% and 53.8% of the poly(A) sites were found within 10 nts of the previous data. This overlap is modest, however, in each dataset a proportionally larger amount (16.2% and 15.7% in Wt and CFIm25 KD) were found to map within 500 nts downstream of the annotated genes in the UCSC database suggesting the S2 cells express a significant amount of mRNA that are longer than annotated or that the annotations of the 3' ends of genes are imprecise. A small proportion of the poly(A) sites were found in unannotated regions, 146 (1.9%) and 174 (2.2%). Again, 54 and 67 of these contain AWUAAA motifs within 100 nts upstream of the poly(A) sites reported here, indicating that a significant proportion of these corresponded to likely bona fide poly(A) sites.

TABLE 5

Locations of detected poly(A) site and comparison to Poly(A)DB in MiSeq dataset in Drosophila. Reads shown and poly(A) sites shown in italics.

| | | | | |
|---|---|---|---|---|
| Present in three replicates | 1349733 | 63.33% | 1476633 | 60.91% |
| | *6910* | | *7473* | |
| UCSC Genes | 1107774 | 82.07% | 1220520 | 82.66% |
| | *5467* | *79.12%* | *5919* | *79.21%* |
| Of which: | | | | |
| Exons | 1060974 | 77.73% | 1162635 | 78.29% |
| | *5250* | *68.16%* | *5646* | *71.34%* |
| 3' prime exon | 1043196 | 76.43% | 1142496 | 76.93% |
| | *5005* | *64.97%* | *5362* | *67.75%* |
| Within 500 nts down-stream of UCSC annotation | 221052 | 16.19% | 232782 | 15.67% |
| | *1297* | *16.84%* | *1380* | *17.44%* |
| Remaining | 20907 | 1.53% | 23331 | 1.57% |
| | *146* | *1.90%* | *174* | *2.20%* |
| Poly(A)DB | 1163220 | 85.22% | 1273905 | 85.78% |
| | *4681* | *60.77%* | *4927* | *62.26%* |
| Poly(A)DB +/− 10 nts | 1250631 | 91.62% | 1363980 | 91.85% |
| | *5538* | *71.89%* | *5850* | *73.92%* |

Figure 6A:
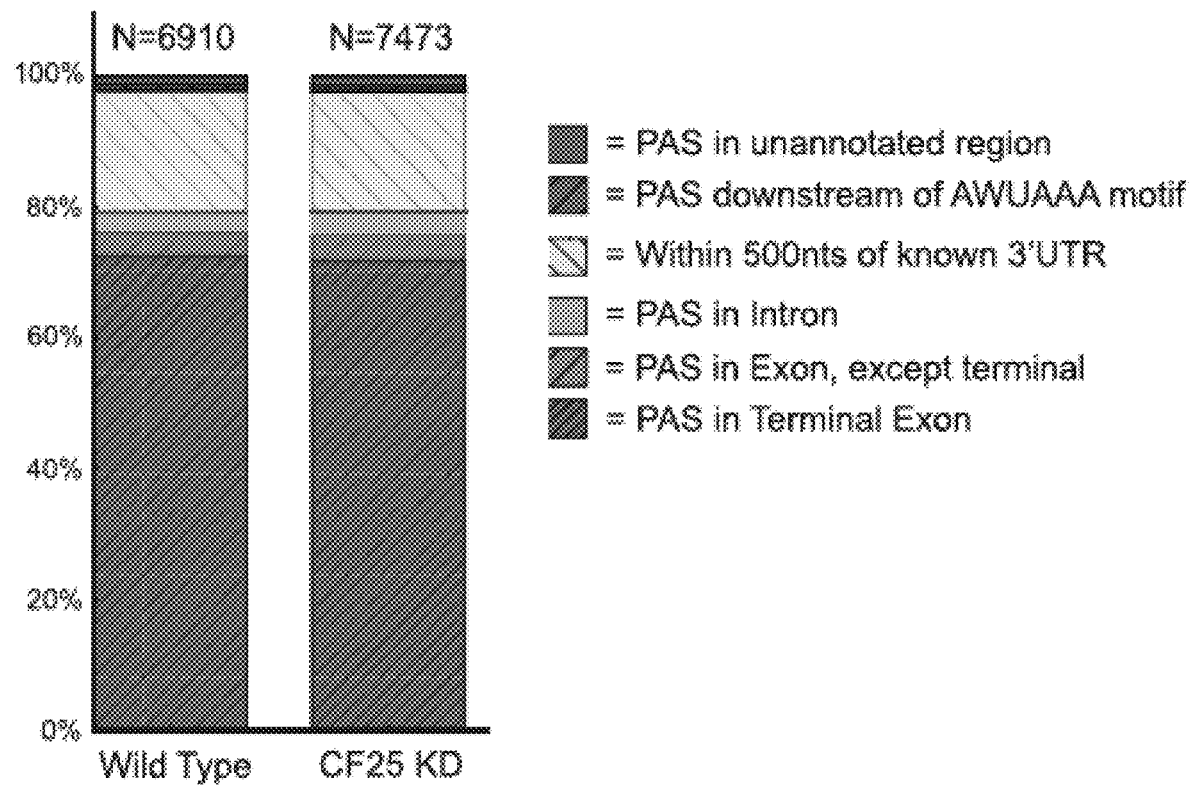
FIGS. 6A to 6D show PAC-seq analysis of *Drosophila melanogaster* cells in culture reveal little effect of CF25d known-down upon poly(A) site selection.
Figure 6B:
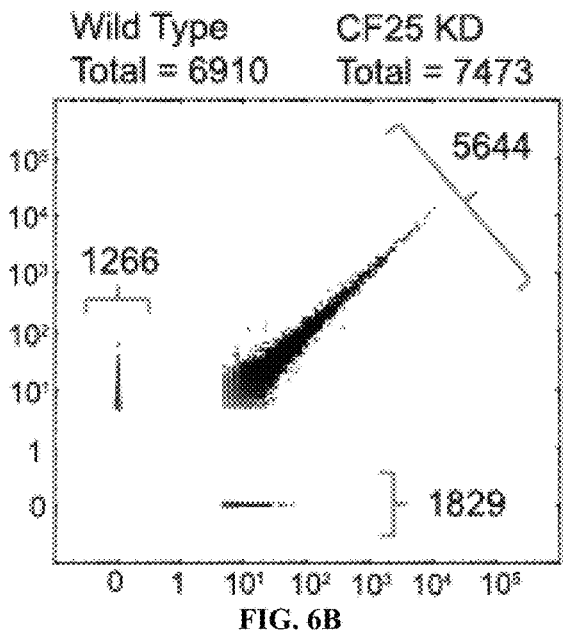
Figure 6C:
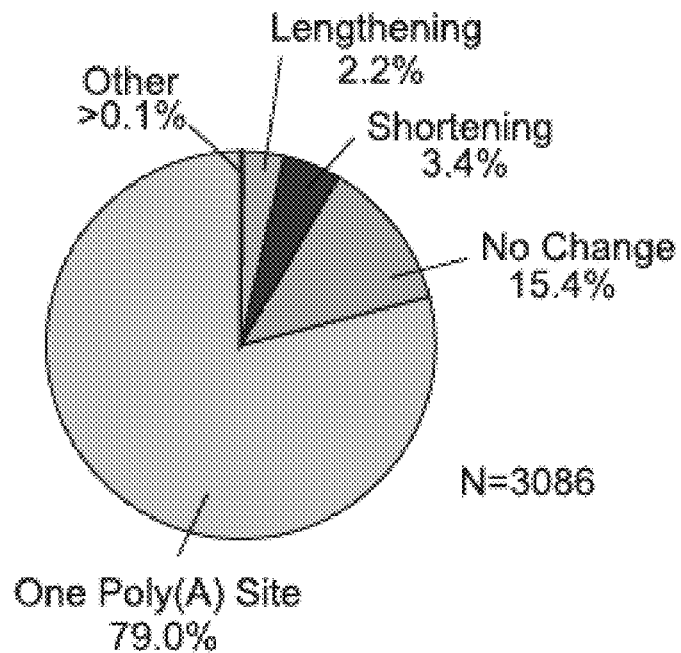

Next, the inventors characterized any changes in poly(A) site selection upon CFIm25 KD. Unlike the observation of broad APA in human cells in response to CFIm25 knockdown, the inventors observed fewer changes in poly(A) site position and frequency when the fly orthologue is knocked down (FIG. 6B, Pearson coefficient=0.99). Moreover, a much smaller proportion of genes contained multiple poly (A) sites (648 out 3086 genes) than was found for the HeLa cells (FIG. 6C). From these, a small percentage of these exhibited significant APA upon CFIm25 KD (greater than 20% change in PAS abundance—107 shorted, 67 longer, 5 both).

Figure 6D:
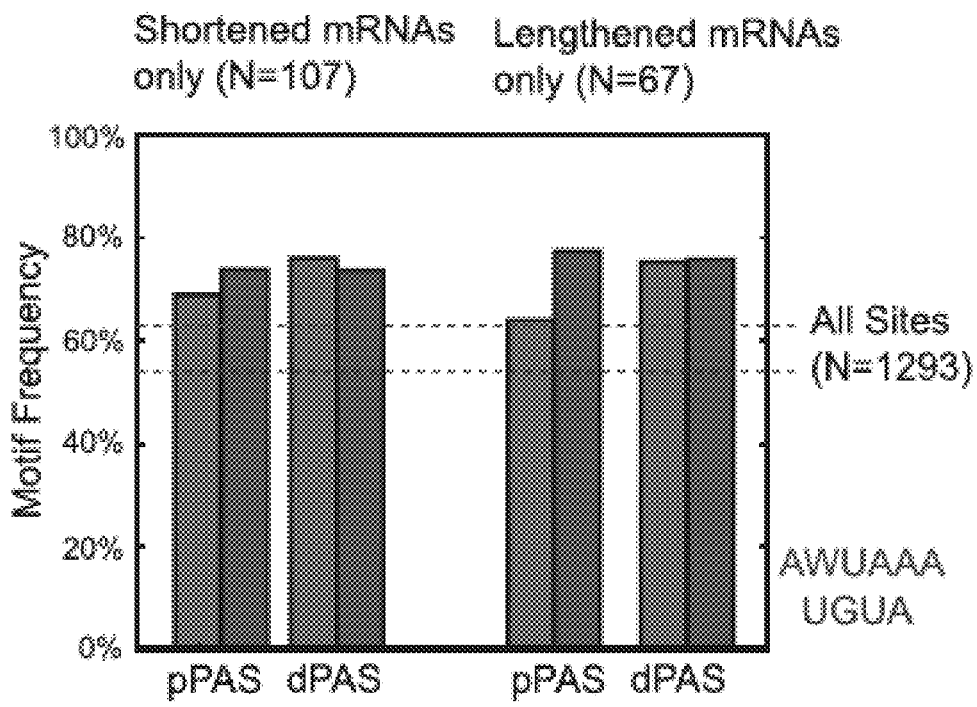
Figure 7A:
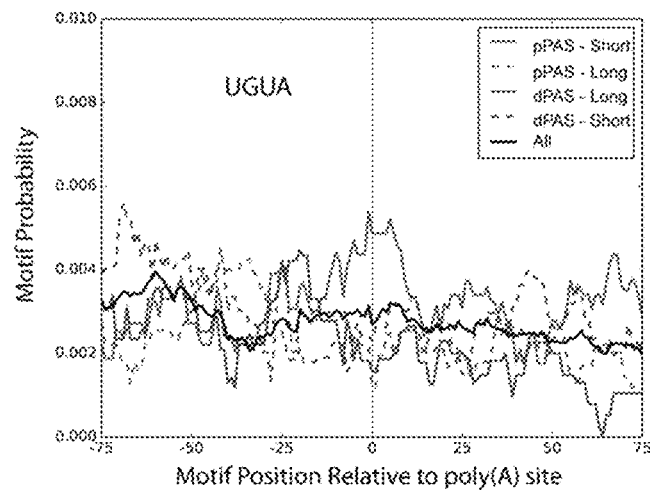
FIGS. 7A and 7B shows motif enrichment analysis using MEME suite illustrates the position of enriched motif relative to detected poly(A) sites. This reveals AWUAAA sites ~20-40 nts upstream of detected poly(A) sites found in *Drosophila melanogaster* S2 cells either with or without CF25d knockdown. Although UGUA are significantly enriched, there is no positional preference. Traces are shown for all found poly(A) sites (All), and for proximal (pPAS) and distal (dPAS) sites found in mRNAs that were either lengthened (Long) or shortened (Short) upon CF25d knockdown.
Figure 7B:
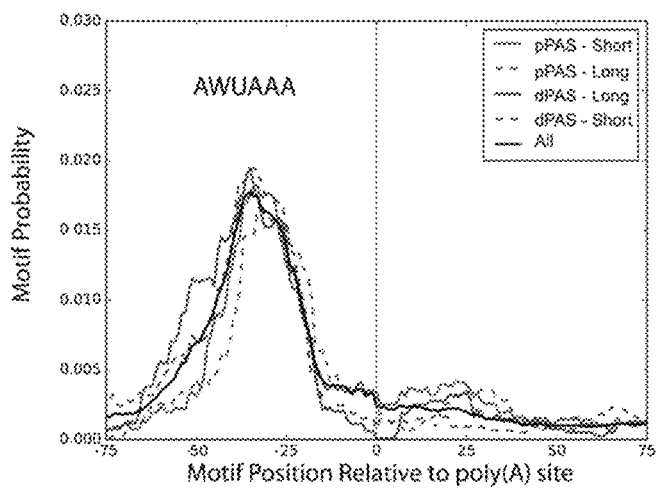

Nonetheless, for the few genes that did exhibit APA, the inventors analyzed enrichment of the AWUAAA and UGUA motifs. Both these motifs were found to be significantly enriched upstream of the poly(A) sites (72.0% and 76.5%) and their positional distribution was found to be similar to that observed for HeLa cells (FIGS. 7A and 7B). However, while the inventors observe a similar enrichment for AWUAAA motifs in the distal sites, the inventors now also observe an enrichment for UGUA (FIG. 6D). Importantly however, this enrichment is the same regardless of whether mRNAs are lengthened or shortened upon CFIm25 KD (in contrast to the HeLa cell data, compare to FIGS. 5D and 5F). This implies that APA in S2 cells is less dependent upon CFIm25 for poly(A) site choice.

As the applications of next-generation sequencing grow and diversify, a key challenge will be developing cost-effective, robust, and sensitive methods for the generation of targeted cDNA libraries. Here the inventors presented a simple, quick and cost-effective method for the generation of next-generation sequencing libraries called Poly(A)-Click-Seq (or PAC-seq) that specifically enriches for the junction of the 3' UTR and poly(A) tail junction. The inventors demonstrated that the inventors could recapitulate the findings of previous analyses of the poly(A) landscape in both human and *Drosophila* cell-lines. As well as confirming the presence of previously annotated transcripts termination sites, PAC-seq was also able to identify novel poly(A) sites that are likely bona fide given their proximity to AWUAAA.

Using the approach of the present invention, the inventors also demonstrate that poly(A) sites that are down-regulated upon CFIm25 knock-down are relatively enriched for the UGUA motif. While the majority of these downregulated sites are at the distal poly(A) site resulting in 3'UTR shortening, there was a small group of transcripts that underwent 3'UTR lengthening, which correlated with the enriched UGUA motif is located at the proximal poly(A) site. These two observations generate a simplified model where reduced expression of CFIm25 will result in loss of enhancement of poly(A) sites that are rich in UGUA causing the usage of other poly(A) sites within a given transcript. This model is simpler in that it does not require that CFIm25 functions as a repressor of poly(A) site selection but rather is always an enhancer of cleavage and polyadenylation, which is consistent with its originally postulated function as an essential CPA member.

The method provides a number of advantages over other popular approaches. The first is that no sample preparation or purification is required. The inventors demonstrated here that poly(A) sites can be sequenced directly from total cellular RNA extracts without enrichment for polyadenylated RNAs or removal of ribosomal RNAs (for example). This has three important consequences: (i) these enrichment/depletion steps are time-consuming and their cost can be significant; (ii) enrichment/depletion steps can potentially impart significant bias leading to uneven sequence coverage, and can inadvertently obscure potentially interesting species (such as rRNA degradation products); and (iii) library generation is markedly simplified, reducing manipulation and loss of precious samples. To extend on this point, the inventors show that as little as 125 ng of total cellular RNA can be used to create a robust PAC-seq library that is nearly identical in quality and coverage to a library generated from 2 µg. This may be further improved with developments in the efficiency of the click-ligation reaction and subsequent PCR amplification conditions. Overall, this demonstrates a compelling degree of sensitivity of this approach, which may allow for the use of PAC-seq in highly challenging biological contexts such as the poly(A) profiling directly from tumor biopsies.

A second key advantage is that, similar to ClickSeq, PAC-seq does not require RNA sample fragmentation. There are few available methodologies that remove the fragmentation steps of NGS library synthesis. Removing this step again simplifies sample preparation, and also avoids the biases that can arise due to RNA fragmentation protocols and subsequent adaptor ligation. This advantage also removes any need for specialized equipment beyond standard laboratory items. Another advantage is that the inventors use non-anchored poly(T) primers, allowing non-primer-derived As to be found in the final RNAseq reads. As described in the methods section, this allows for an additional quality filtering protocol that substantially improves confidence in reported poly(A) tails. Moreover, the distributions of poly(A) lengths can be inferred for each detected poly(A) sites. Poly(A) tail length is an important variable affecting RNA stability and half-life. Therefore, PAC-seq may also be used to assess site-specific changes in poly(A) tail lengths.

Although the inventors did not explore this possibility in their manuscript, the click-ligated adaptors can also be designed to contain single-molecule indexes, (a.k.a. unique-molecular identifiers) similar to the PrimerID strategies used to sequence HIV protease (64). This can allow for sequence error correction and perhaps more importantly, for assessment of PCR mediated duplication bias. For some samples, it may be necessary to perform many rounds of PCR amplification in order to generate enough substrate to load onto an Illumina flowcell. By including single-molecule indexes in the click-adaptor, over-sampling errors can be corrected.

Overall, PAC-seq is a simple, quick and cheap method for NGS library generation that captures the 3'UTR/poly(A) tail junction with high efficiency resulting in a reduced need for sequence depth. From the initial HiSeq dataset, approximately 50% of the total raw sequences reads were utilized to the final analysis. While saving on cost, this also allows for a single experiment with multiple replicates to be performed on a single MiSeq flowcell. The current v3 MiSeq kit can yield ~25 million read under optimal conditions. This would allow over ten replicates of a single experiment at a coverage of 2 million reads per dataset. This coverage depth is sufficient for analyzing even highly complex genomes such as in human cells.

Test Kit and Individual Reactions.

2.1 Reverse Transcription Components:
- Deoxyribonucleotide set (dNTPs) (10 mM in water)
- 3'-Azido-2',3'-dideoxynucleotides (AzNTPs) (10 mM each in water) (Trilink Biotechnologies, N-4007, N-4008, N-4009, N-4014). Reagents are stored frozen and mixed thoroughly prior to use.
- During reverse transcription, the ratio of AzNTPs to dNTPs determines the distribution of cDNA fragment lengths generated. AzVTP:dNTP mixtures are made by making appropriate dilutions of each 10 mM AzNTPs in 10 mM dNTPs.
- Reverse transcriptase: one choice is Superscript II or III (Life Technologies) which is provided with standard reaction buffers.
- RNaseOUT Recombinant Ribonuclease Inhibitor (Life Technologies)
- RNaseH (NEB)
- The skilled artisan will recognize that a ratio of the three 2'- or 3'-azido-nucleotides (AzGTP, AzCTP and AzATP) to dNTPs can be, e.g., 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM:1 mM 2.2 Click-Chemistry Components:
- Click-adapter stock is resuspended in 10 mM Tris pH 8.0 and 0.5 mM EDTA at 100 µM; working solutions of Click-adapter at 5 µM in water
- Copper(II)-Tris(benzyltriazolylmethyl)amine complex (Cu-TBTA) 10 mM in 55% aq. DMSO (Lumiprobe) or home-made.

50 mM L-Ascorbic Acid is prepared by dissolving 0.44 grams powdered L-Ascorbic Acid in 50 ml water. Aliquots are dispensed into 200 µl micro-Eppendorf tubes and stored at −20° C. One aliquot is used fresh per experiment and discarded after use.
100% DMSO (e.g. sigma)
50 mM HEPES pH 7.2

2.3 PCR Reaction
OneTaq DNA Polymerase 2× Master Mix with standard buffer (NEB, M0482)

2.4 Other reagents and equipment
E-Gel Precast Agarose electrophoresis system with 2% Agarose gels (Life Tech).
Blue light Transilluminator (e.g. Safe Imager 2.0 Blue-Light Transilluminator, Life Tech)
100 bp DNA ladder
Zymo DNA Clean and Concentrator-5 (Zymo Research, D4013)
Zymo Gel DNA Recovery Kit (Zymo Research, D4007). (This kit is the same as the 'Clean & Concentrator' with the addition of the agarose dissolving buffer)
Qubit fluorimeter (Life Tech).
Standard Thermocyclers
Standard Tabletop centrifuges 2.5 Primers and Oligos:

| Primer Name | Sequence | Stock Solution | Working Solution |
|---|---|---|---|
| "3' Illumina_4N_21T" (partial p7 Adaptor)[4] (see Note 4.1) | *Biotin*-GTGACTGGAGTTCAGACGTGTGCTCTTCCGA TCTNNNN$_{0-12}$ T$_{9-30}$ (SEQ ID NO: 6) | 100 µM in Water | Same as Stock |
| Click-Adapter (p5 Adaptor)[2,4] | 5'Hexynyl-NNNN$_{0-12}$ AGATCGGAAGAGCGTCGTGTAGGGAAAGA GTGTAGATCTCGGTGGTCGCCGTATCATT - *Biotin* (SEQ ID NO: 7) | 100 µM in TE1 | 5 µM in water |
| Indexing Click-Adapter (p5 Adapter)[2,3,4] | 5'Hexynyl-NNNN$_{0-12}$ AGATCGGAAGAGCGTCGTGTAGGGAAAGA GTGT[index-seq]GTGTAGATCTCGGTGGTCGCCGTATCATT - *Biotin* (SEQ ID NO: 7) | 100 µM in TE1 | 5 µM in water |
| Universal Primer Short [UP_S] (p5 Adaptor) | AATGATACGGCGACCACCGAG (SEQ ID NO: 9) | 100 µM in TE | 5 µM in water |
| 3' Indexing Primer #1 (remaining p7 Adaptor)[3] | CAAGCAGAAGACGGCATACGAGAT[index-seq]GTGACTGGAGTTCAGACGTGT (SEQ ID NO: 8) | 100 µM in TE | 5 µM in water |

[1]TE = 10 mM Tris pH 8.0, 1 mM EDTA
[2]The Click-adapter can be purchased from IDT Integrated DNA Technologies. HPLC purification is required by the vendor and recommended by us.
[3]Underlined portion of the primers corresponds to the sequence that can be used for indexing/barcoding.
[4]Optional biotin tag on primer 3.1 Reverse Transcription 1. Input RNA: in principle, any input RNA can be used to generate RNAseq libraries. We have successfully sequenced viral genomic RNA, total cellular RNA, poly(A)-selected RNA and ribo-depleted RNA. RNA should be provided in pure water, following standard precautions to avoid RNase activity. For poly(A)seq, we usually aim to provide 4 ug of RNA (see note 4.2). No sample fragmentation is required. No sample purification/rRNA depletion/selection is required.
    a. Total crude extract can also be used to generate RNAseq libraries. No extraction methods are required as little as $10^4$ cells can be used
2. For a 1:5 5 mM AzVTP:dNTP solution: Mix the following
    a. 10 µl 10 mM dNTPs
    b. 2 µl 10 mM AzATP
    c. 2 µl 10 mM AzCTP
    d. 2 µl 10 mM AzGTP
    e. 4 µl H$_2$O (NOTE: do not add AzTTP!!!)
3. The reverse transcription is performed using standard protocols, with the exception that the reaction is supplemented with small amounts of azido-nucleotides (AzVTPs). Set up RT-PCR reaction as follows for a 13 µl reaction:
    a. 2 µl 5 mM AzVTP:dNTP mixture at 5 mM (see notes 4.3 and 4.4). Use 1:5 Ratio for PAC-Seq
    b. 1 µl 3' Illumina_4N_21T primer at 100 µM
    c. x µl RNA to a total mass of ≤4 µg (Adjust volumes as necessary)
    d. H$_2$O to a final volume of 13 µl 4. Incubate mixture at 65° C. for 5 mins to melt RNA and immediately cool on ice for >1 min to anneal semi-random primer. This high melting temperature is tolerated as small amounts of RNA fragmentation does not diminish efficiency of library generation.
5. Add the following on ice for a final reaction volume of 20 μl (see note 4.5): (Keep cool to prevent non-specific amplification).
   a. 4 μl 5X Superscript First Strand Buffer
   b. 1 μl 0.1M DTT
   c. 1 μl RNase OUT
   d. 1 μl Superscript III Reverse Transcriptase
6. Incubate with the following steps:
   a. 50° C. for 10 mins,
   b. 75° C. for 15 mins, and
   c. Hold at 4° C.
7. To remove template RNA, add 0.5 μl RNase H (NEB) and incubate at 37° C. for 20 mins, 80° C. for 10 mins, and then hold at 4° C.

3.2 Azido-Terminated cDNA Purification (3 Different Methods can be Used)

After cDNA synthesis and RNA digestion, the azido-terminated cDNA must be purified away from the AzNTPs present in the RT-PCR reaction mix. These small molecules will be in molar excess of azido-terminated cDNA by many orders of magnitude and will compete for ligation to the alkyne-modified 'click-adaptor' if not completely removed. This can be achieved in a number of ways. *note: see note 11, we can also do something that we call 'click on column/bead' where we don't elute the cDNA [3.2.1.4 or 3.2.2.8] and do the click reaction on the column or beads.

3.2.1 Column Clean

1. Take 20.5 μl RT-PCR reaction, and add 140 μl Zymo DNA binding buffer (7:1 binding buffer:DNA).
2. Apply to silica column, and centrifuge for 30-60 s at 14'000 RPM, as per the manufacturer's protocol.
3. Wash with 200 μl ethanol-containing wash buffer and centrifuge for 30-60 s at 14'000 RPM as per the manufacturer's protocol. Repeat for two washes.
4. Elute by centrifugation for 60 s at 14'000 RPM into fresh non-stick Eppendorf tubes using 10 μl 50 mM HEPES pH 7.2 or water (see note 4.6).

3.2.2 SPRI Bead Clean

1. Take 20.5 μl RT-PCR reaction, and add 1.8X (36 uL) SPRI magnetic beads [AMPure XP], pipette mix
2. Incubate 5 min at RT
3. Pellet beads on magnetic rack
4. Remove and discard supernatant
5. Wash beads with 200 uL 70% EtOH, do not disturb pellet (repeat wash for 2 total times)
6. Remove beads off magnetic rack
7. Resuspend beads in 10 uL 50 mM HEPES pH 7.2
8. Transfer supernatant to a new tube

3.2.3 Streptavidin Magnetic Bead Wash

This method can only be used if a biotinylated primer was used (step: 3.1.3.b)
1. Take 20.5 μl RT-PCR reaction, and add 3 uL of clean streptavidin beads
2. Incubate 30 min at RT
3. Pellet beads on magnet and discard supernatant
4. Resuspend beads in 200 uL TBST (150 mM NaCl, 50 mM Tris pH 7.5, 0.5% Tween)
5. Pellet beads on magnet and discard supernatant
6. Resuspend beads in 200 uL TBS (150 mM NaCl, 50 mM Tris pH 7.5)
7. Pellet beads on magnet and discard supernatant
8. Resuspend beads in 200 uL 50 mM HEPES pH 7.2
9. Pellet beads on magnet and discard supernatant
10. Resuspend in 10 uL HEPES 50 mM pH 7.2

Click-ligation. Following purification of the single-stranded azido-terminated cDNA, the click-ligation reaction is performed to join the 5' alkyne-modified click-adapter on to the 3' end of the azido terminated cDNA. This generates a longer single stranded cDNA with a triazole-ring and a long hexynyl linker in place of a phosphate backbone (see FIG. 2F).

1. First, dilute the azido-terminated cDNA in DMSO and add a large molar excess of the click-adapter using the following volumes:
   a. 10 μl azido-terminated cDNA (in HEPES)
   b. 20 μl 100% DMSO (see note 4.7) [solvent] (See Table 6 below)
   c. 3 μl Click-Adapter at 5 μM in water (note: EDTA will chelate copper required in click-reaction and so must be minimized)
2. Next, generate the catalyst and accelerant mixture (for multiple samples, prepare a stock mixture):
   a. 0.4 μl Vitamin C at 50 mM [accelerant] (See Table 6 below)
   b. 2 μl Cu-TBTA in 55% DMSO. [ligand] (See Table 6 below)
3. Upon addition of Vitamin C, the Cu-TBTA reagent will turn from a light blue to colorless liquid, indicating the reduction of the Cu(II) ions to Cu(I). Wait 30-60 s to ensure full reduction of the copper ions (see note 4.8).
4. Add 2.4 μl of the Vitamin C and Cu-TBTA mixture to the each cDNA sample to initiate the click-ligation.
5. Allow reaction to proceed at room-temperature for at least 30 mins (see notes 4.9, 4.10, and 4.11). (See Table 6 below)

3.4 Click-Ligated cDNA Purification:

To remove the components of the click-ligation we use any of the following methods:

3.2.1 Column Clean—

1. The click-ligation reaction is first diluted with 60 μl water to a total volume of 100 μl prior to addition of the DNA binding buffer in order to dilute the DMSO.
2. Take 100 μl click-ligation reaction, and add 700 μl Zymo DNA binding buffer (7:1 binding buffer:DNA).
3. Apply to silica column, and centrifuge for 30-60 s at 14'000 RPM, as per the manufacturer's protocol.
4. Wash with 200 μl ethanol-containing wash buffer and centrifuge for 30-60 s at 14'000 RPM as per the manufacturer's protocol. Repeat for two washes.
5. Elute by centrifugation for 60s at 14'000 RPM into fresh non-stick Eppendorf tubes using 10 μl 10 mM Tris pH 7.4 or water.

3.4.2 SPRI Bead Clean

1. Take 37.8 μl of cDNA, and add 1.8X (68 uL) SPRI magnetic beads [AMPure XP], pipette mix
2. Incubate 5 min at RT
3. Pellet beads on magnetic rack
4. Remove and discard supernatant
5. Wash beads with 200 uL 70% EtOH, do not disturb pellet (repeat wash for 2 total times)
6. Remove beads off magnetic rack
7. Resuspend beads in 10 uL 10mM Tris pH 7.4
8. Transfer supernatant to a new tube

3.4.3 Streptavidin Magnetic Bead Wash

This method can only be used if a biotinylated primer was used (step: 3.1.3.b or 3.3.1.c)
*If streptavidin beads were used at step 3.2 then skip to step 3.4.3.2 below*

1. Take 37.8 μl of cDNA, and add 3 uL of clean streptavidin beads
2. Incubate 30 min at RT
3. Pellet beads on magnet and discard supernatant
4. Resuspend beads in 200 uL TBST (150 mM NaCl, 50 mM Tris pH 7.5, 0.5% Tween)
5. Pellet beads on magnet and discard supernatant
6. Resuspend beads in 200 uL TBS (150 mM NaCl, 50 mM Tris pH 7.5)
7. Pellet beads on magnet and discard supernatant
8. Resuspend beads in 200 uL 50 mM HEPES pH 7.0
9. Pellet beads on magnet and discard supernatant
10. Resuspend in 10 uL Tris 10 mM pH 7.4

3.5 Final PCR Amplification:

The inventors have screened a number of cycling conditions and have found the following to give the best results, but the skilled artisan will know how to vary the conditions based on the ATCG ratios, temperatures, salt conditions, etc.:

1. Mix at room temperature for a 50 μl reaction:
   1. 5 μl Clean Click-ligated DNA (in 10 mM Tris pH 7.4) (see note 4.13).
   2. 2.5 μl 3' Indexing Primer (1 barcode/sample) at 5 μM
   3. 2.5 μl Universal Primer Short [UP-S] at 5 μM
   4. 15 μl H$_2$O
   5. 25 μl 2X One Taq Standard Buffer Master Mix
2. Cycle on a standard thermocycler using the following steps (see note 4.14):
   1. 94° 1 min;
   2. 53° 30 sec,
   3. 68° 10 min
   4. 94° 30 sec,
   5. 53° 30 sec,
   6. 68° 2 min] × 10-25 cycles (May require more cycles if less than 4 μg in original sample).
   7. 68° 5 min;
   8. 4° ∞, Standard PCR reaction, any PCR enzyme should work and the conditions that correlate with that pcr enzyme should be used with it
3. Purify the PCR product with either 2 methods:
   1. Zymo DNA clean protocol (see note 4.15):
      i. Take the 50 μl PCR reaction and add 250 μl Zymo DNA binding buffer (5:1 binding buffer:DNA).
      ii. Apply to silica column, and centrifuge for 30-60 s at 14'000 RPM, as per the manufacturer's protocol.
      iii. Wash with 200 μl ethanol-containing wash buffer and centrifuge for 30-60 s at 14'000 RPM as per the manufacturer's protocol. Repeat for two washes.
      iv. Elute by centrifugation for 60 s at 14'000 RPM into fresh non-stick Eppendorf tubes using 20 μl 10 mM Tris pH 7.4 or water.
   2. SPRI beads:
      i. Take 50 μl of cDNA, and add 1X (50 uL) SPRI magnetic beads [AMPure XP], pipette mix
      ii. Incubate 5 min at RT
      iii. Pellet beads on magnetic rack
      iv. Remove and discard supernatant
      v. Wash beads with 200 uL 70% EtOH, do not disturb pellet (repeat wash for 2 total times)
      vi. Remove beads off magnetic rack
      vii. Resuspend beads in 10 uL 10 mM Tris pH 7.4
      viii. Transfer supernatant to a new tube

3.6 Gel Extraction and Size Selection [Size Selection can Also be Done Using SPRI Beads].

1. Add 20 μl eluted cDNA library onto a 2% agarose precast pre-stained e-gel. For multiple samples, run empty wells in between each sample to prevent cross-contamination of final libraries. Also run a 100 bp MW ladder (e.g. NEB).
2. Run using 1-2% agarose protocol for 10 mins (E-Gel iBASE Version 1.4.0; #7)
3. After run has completed, image gel on blue transilluminator and keep image for records (e.g. FIG. 4A).

4. Crack open precast gel cassette, and with a fresh/clean scalpel or razor blade, excise the desired cDNA library sizes. In ClickSeq, the total length of adapters are 126 bp. Therefore, minimum cDNA library size should be 176 bp for 1 × 50 bp SE Illumina. Example in FIG. 4B shows a library excised from 200-400 bp for a 1 × 300 bp SE Illumina run on a HiSeq for PAC-Seq. Cut 200-300 (or less, data pending . . . ) for 1 × 150 PAC-Seq MiSeq run.
5. Weigh excised gel and mix 3:1 volume for weight Zymo Agarose dissolving buffer (ADB)(e.g. 180 µl ADB for 60 mg agarose)
6. Incubate at 50° C. for approximately 10 mins. Make sure that agarose has entirely dissolved before proceeding. Take care not to incubate at temperatures greater than 50° C., as thismay partially melt some dsDNA fragments and result in improper quantification.
7. Purify the PCR product with the Zymo DNA clean protocol:
    a. Apply melted agarose in ADB to silica column, and centrifuge for 30-60 s at 14'000 RPM, as per the manufacturer's protocol.
    b. Wash with 200 µl ethanol-containing wash buffer and centrifuge for 30-60 s at 14'000 RPM as per the manufacturer's protocol. Repeat for two washes.
    c. Elute by centrifugation for 60 s at 14'000 RPM into fresh non-stick Eppendorf tubes
    d. using 6-10 µl 10 mM Tris pH 7.4 or water.
8. Quantify yield of final size selected cDNA library using a QuBit fluorimeter.

3.7 Sequencing and ClickSeq-specific data preprocessing. ClickSeq Libraries can be submitted for single-end sequencing on Illumina platforms using the adaptor sequences described here. The first read is obtained from the Illumina universal primer end (p5) end of the cDNA fragment which is the location of the triazole ring in the original cDNA. The second read starts from the indexing (p7) adaptor, which contains the polyA tail.

Additional Notes. Click Chemistry is broadly defined as "biocompatible small molecule reactions commonly used in bioconjugation, allowing the joining substrates of choice with specific biomolecules". A range of different chemistries for bioconjugation are feasible, as well as the catalyst/accelerant and solvent conditions-see Presolski et al. JACS 2010: ncbi.nlm.nih.gov/pubmed/20863116). In ClickSeq, the inventors have demonstrated the feasibility of a wide range of ligand/solvent combinations, while precedent in the literature exist for many other broad conditions. These are summarized below.

TABLE 6

| Solvents: |
| --- |
| $H_2O$ |
| 10-70% DMSO |
| 70% Ethanol |
| Zymo "DNA binding buffer" |
| Metal Catalyst |
| Copper (Cu2+ ions) or elemental copper (e.g. copper wire) |
| Ruthenium |
| Chelating Ligand |
| TBTA: |
|    Tris[(1-benzyl-1H-1,2,3-triazol-4-yl)methyl]amine |
| THPTA: |
|    Tris(3-hydroxypropyltriazolylmethyl)amine |
| (BimC4A)3: |
|    Tripotassium 5,5',5"-[2,2',2"-nitrilotris(methylene)tris(1H-benzimidazole-2,1-diyl)]tripentanoate hydrate |
| Accelerant |
| Ascorbic acid (a.k.a. Vitamin C) |
| TCEP: |
|    tris(2-carboxyethyl)phosphine |

TABLE 6-continued

| Buffers |
| --- |
| HEPES |
| TRIS |
| Na/K Phosphate |
| $H_2O$ |

Example 2. Poly(A)-ClickSeq as a Tool Enabling Simultaneous Genome-Wide Poly(A)-Site Identification and Differential Expression Analysis The use of RNA-seq as a generalized tool to measure the differential expression of genes has essentially replaced the use of the microarray. Despite the acknowledged technical advantages to this approach, RNA-seq library preparation remains mostly conducted by core facilities rather than in the laboratory due to the infrastructure, expertise and time required per sample. Described hereinabove is the basic two 'click-chemistry' based library construction methods termed ClickSeq and poly(A)-click-seq (PAC-seq) as alternatives to conventional RNA-seq that are both cost effective and rely on straightforward reagents readily available to the skilled artisan. ClickSeq is random-primed and can sequence any (unfragmented) RNA template, while PAC-seq is targeted to poly(A) tails of mRNAs. This example uses the PAC-seq as a platform that allows for simultaneous mapping of poly(A) sites and the measurement of differential expression of genes. PAC-seq offers a unique advantage over other 3' end mapping protocols in that it does not require additional purification, selection, or fragmentation steps allowing sample preparation directly from crude total cellular RNA. This example shows that PAC-seq is able to accurately and sensitively count transcripts for differential gene expression analysis, as well as identify alternative poly(A) sites and determine the precise nucleotides of the poly(A) tail boundaries.

Figure 8:
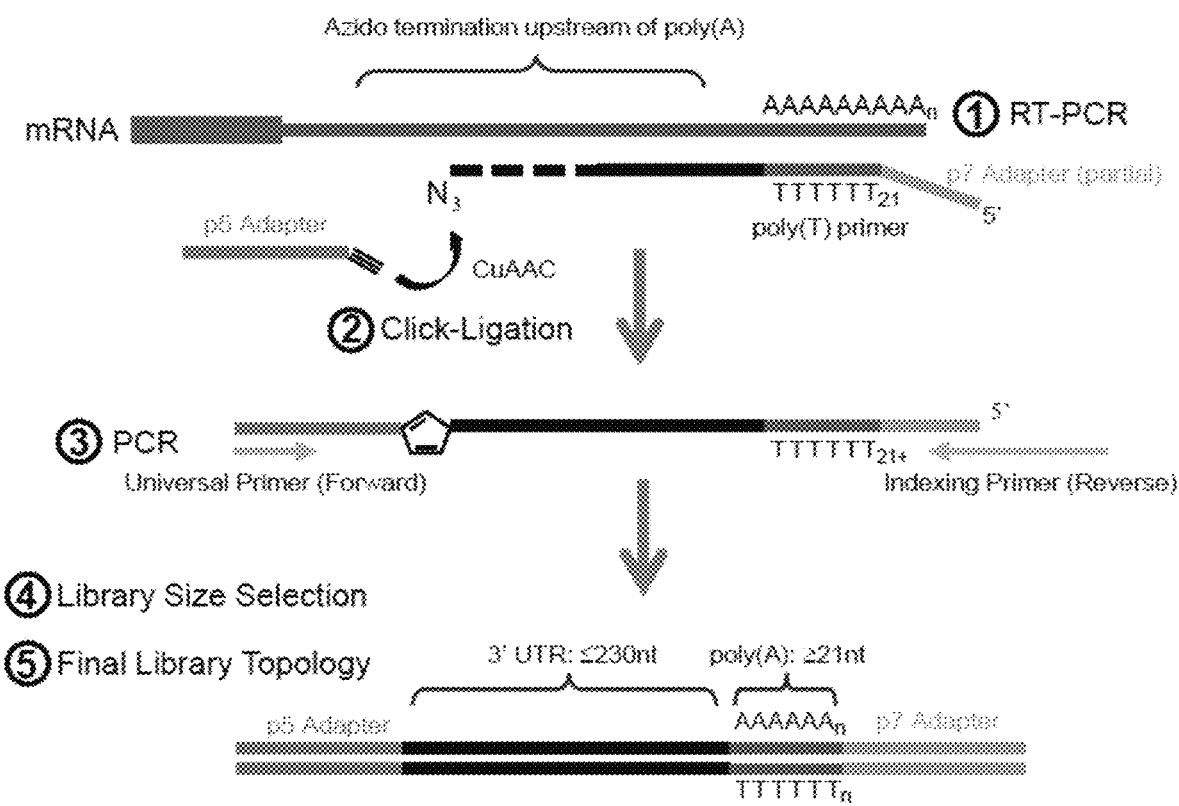
FIG. 8 is a schematic of the steps in the PAC-seq library preparation. (1) A non-anchored 21-dT primer with a partial p7 adapter sequence is used to reverse synthesize mRNA containing a poly(A) tail. 3'-azido-deoxynucleotides (AzCTP, AzATP, and AzGTPs) are added to terminate the RT-reaction randomly depending on dNTP:AzVTP ratio upon reaching the 3'UTR. (2) Click chemistry is used to attach a p5 universal adapter to the azido-terminated 3' end of the cDNA. (3) PCR is then performed using the p5 Universal primer and Indexing primers completing the p7 end. (4) The PCR product is electrophoresed on an agarose gel and the band corresponding to products with a 3'UTR segment of approximately 230 nt is selected for purification. (5) Representation of final PAC-seq preparation that is used for downstream sequencing.

Example 1 shows that Poly(A)-ClickSeq (PAC-seq) specifically targets sequences the 3' ends of poly(A)-tailed mRNAs allowing quantification of the positions and abundance of poly(A) sites (PASs) at the ends of eukaryotic mRNAs. For PAC-seq, the inventors initiate reverse transcription using poly(T) primers, without a non-T anchor. Importantly, to specifically generate sequence reads spanning the junctions of mRNA 3'UTRs and poly(A) tails, AzTTP is omitted from the RT-PCR reaction (AzVTPs). As a result, reverse-transcription must continue through to beginning of the poly(A)-tail and into the 3'UTR before chain termination can occur, thus 'homing-in' on the 3'UTR/poly(A) junction. Thereafter, the inventors can purify the azido-terminated cDNA, click-ligate the 5' Illumina adaptor and generate an NGS library enriched with 3'UTR/poly(A) junctions. A schematic is illustrated in FIG. 8. By virtue of priming from the poly(A) tails of mRNAs and terminating shortly upstream, no fragmentation, enrichment of poly(A)-tailed RNAs, nor depletion of ribosomal RNA is required. The inventors have previously demonstrated that they can robustly generate PAC-seq libraries from as little as 125 ng of crude total cellular RNA.

The primary goal of PAC-seq was to identify and characterize the frequency and positions of poly(A) sites (PASs) within the transcriptome. In this example, the inventors describe how the inventors can also use PAC-seq to perform differential gene expression (DE) analysis. To illustrate the utility of PAC-seq, the inventors depleted a component of the *Drosophila* Integrator complex in DL1 cells using RNAi and compared the gene expression changes relative to control dsRNA-treated cells. RNA isolated from these cells was then subject to standard RNA-seq or PAC-seq and DE analyses were performed using each library generation method. In addition to providing information on poly(A) tail position, the inventors demonstrate that PAC-seq also reveals global changes in the mRNA transcript abundance and that these results closely match the changes observed by canonical RNA-seq methods. PAC-seq therefore provides a robust and cost-effective method for DE analysis that can simultaneously reveal the positions and frequencies of poly (A) sites.

Cell culture and RNA samples. For the RNAi knockdown of target genes, dsRNA of 500 bp in length was prepared using the New England Biological T7 HiScribe kit (NEB) and purified using RNAzol (Sigma). Four wells in a 6-well plate were spotted with 15 µg of dsRNA for each dsRNA target and 1×10$^6$ DL1 cells [12] from *Drosophila melanogaster* were added in 1 mL of serum free media (Gibco) and incubated for 1 hour at 27° C. before the addition of 2 mL media containing 10% FBS. These cells were then incubated for 60 hours at 27° C. before harvesting. Total RNA was extracted from cells in three replicates of each series using the standard TRIzol extraction protocol (Invitrogen) and resuspended in water to a concentration of 500 µg/µL. The final well in each replicate was harvested using RIPA buffer for protein Western analysis of target protein knockdown verification.

Reverse Transcription. For PAC-seq, the inventors followed a modified version of the SuperScript-III (Invitrogen) first-strand reverse transcription protocol by supplementing 3'-Azido-2',3'-dideoxynucleotides (AzVTPs) (Trilink Biotechnologies). First, a 1:5 mix of 5 mM AzVTP:dNTPs was prepared by mixing 24, 10 mM AzATP, 2 µL 10 mM AzCTP, 2 µL 10 mM AzGTP, 104, 10 mM dNTPs each in water, and 44, H$_2$O. The reverse transcription reaction was setup by combining:

2 µL 5 mM 1:5 AzVTP:dNTPs
1 µL Illumina_4N_21T primer (100 µM in water)

(SEQ ID NO: 11)
(GTGACTGGAGTTCAGACGTGTGCTCTTCCGATCTNNNNTTTTTTTTTTT

TTTTTTTTTT), 0.5-2 µg of RNA total cell
H$_2$O to a final volume of 13 µL
Input RNA can be extracted using any standard RNA extraction procedure (e.g. TRIzol) but no further purification, rRNA depletion, poly(A) selection, or fragmentation steps are required. This mixture was incubated at 65° C. for 5 mins to melt RNA and immediately cooled on ice for >1 min to anneal the poly(T) primer. Subsequently, following the standard RT-PCR protocol, the inventors combined the following for a final reaction volume of 20 µL:
4 µL, 5× Superscript First Strand Buffer
1 µL 0.1M DTT
1 µL RNase OUT Recombinant Ribonuclease Inhibitor (40 U/µL) (Invitrogen)
1 µL Superscript III Reverse Transcriptase (200 U/µL)
The RT reaction was incubated at 50° C. for 40 mins, 75° C. for 15 mins, and then held at 4° C. To remove template RNA, 2U of RNase H (NEB) was added and incubated at 37° C. for 20 mins, 80° C. for 10 mins, and held at 4° C.

Azido-terminated cDNA purification. After single strand synthesis and RNA digestion, the azido-terminated cDNA fragments must be purified, removing any excess AzVTPs which may compete with the subsequent click reactions. This can be achieved in many ways including any silica column based extraction (i.e. Zymo Research DNA Clean and Concentrator-5, D4013), phenol/chloroform, or SPRI (Solid Phase Reversible Immobilization) Magnetic Beads such as AMPure beads (Beckman Coulter) or homemade [13]. The inventors prefer to use SPRI beads due to their simplicity of use and high throughput ability. Here, following the standard procedure, the inventors mixed 1.8× (38 µL) SPRI beads into the RT-PCR reaction and incubated for 5 min at room temperature. Beads were pelleted using a magnetic rack, discarding the supernatant. The inventors washed beads twice with 200 µL 80% ethanol taking care not to disturb the bead pellet and air-drying until no excess ethanol was visible. Bead were finally re-suspended in 10 µL 50 mM HEPES pH 7.2, re-pelleted on a magnetic rack and the supernatant containing the eluted cDNA fragments were transferred to a new tube.

Click-ligation to attach sequencing adapter. After purification, a click-ligation reaction is used to chemically attach a 5' alkyne-modified click-adapter onto the 3' end of the azido terminated cDNA fragments. To proceed with the reaction, the inventors diluted the 10 µL of cDNA (from the purification step 2.2.2) with 20 µL 100% DMSO and added 3 µL of 5 µM Click-Adapter. (5'Hexynyl-AGATCG-GAAGAGCGTCGTGTAGGGAAAGAGTGTA-GATCTCGGTGGTCGCCGTATCATT) (SEQ ID NO:12), 5 µM in water (IDT, with HPLC purification).

Next, the inventors separately prepared the catalyst/accelerant mixture by combining 0.4 µL Vitamin C (Sigma) at 50 mM with 2 µL Cu(II)-TBTA (10 mM in 55% aq. DMSO, Lumiprobe). This initiates the reduction of the Cu(II) to Cu(I). The inventors immediately added 2.4 µL of the copper mixture to the 23 µL of cDNA, initiating the click-reaction and incubated for 30 min at room temperature. The inventors repeated the addition of the copper catalyst mixture for a total of two times. This reaction yields a cDNA fragment that is linked to the p5 sequencing adapter through a triazole-ring in place of the phosphate backbone. The cDNA fragments were purified away from the excess components of the click-ligation reaction following the SPRI magnetic bead protocol: 1.8× (68 µL) SPRI beads were added to 37.8 µL of the click-reaction as washed as in step 2.2.2, eluting in 20 µL 10 mM Tris pH 7.4 or water.

Final PCR Amplification. The cDNA fragments were then PCR amplified to add on the remainder of the p7 Illumina sequencing adapter and to generate sufficient enough material for sequencing. The PCR reaction was set up by combining the following reagents for a 50 µL reaction:
 10 µL Clean Click-ligated DNA
 2 µL 5 µM Universal Primer: (AATGATACGGCGAC-CACCGAG) (SEQ ID NO:13),
 2 µL 5 µM Indexing Primer (1 barcode/sample):

(SEQ ID NO: 14)
(CAAGCAGAAGACGGCATACGAGATXXXXXXGTGACTGGAGTTCAGACGT
GT)

underlined
 portion corresponds to the index sequence, any index sequence may be used here
 25 µL 2× One Taq Standard Buffer Master Mix (NEB)
 11 µL $H_2O$
PCR cycling was as follows:
 1 m at 94° C.; 30 s at 54° C.; 10 m at 68° C.;
 [30 s at 94° C.; 30s at 54° C.; 2 m at 68° C.]×15-20 cycles;
 5 m at 68° C.; hold at 4° C.

Finally, the PCR products were cleaned and isolated, again following the SPRI magnetic bead protocol: 1× (50 µL) SPRI beads were added to 50 µL of the PCR reaction, following the same washing procedure as in step 2.2.2, eluting in 20 µL 10 mM Tris pH 7.4 or water.

Gel extraction and size selection. The final sequencing library needs to be size selected. The inventors have found that the most accurate way is by running the amplified cDNA library on an electrophoresis gel and cutting the appropriate band size based off a molecular weight ladder. Size selection is critical for PAC-seq since fragments that are too short will not yield map-able cDNA fragments and long fragments will not cluster properly on the sequencing platform or produce sequence reads that are distal from the poly(A) tail. Therefore, gel size excision should be 200-300 bp for a 1×150 bp Illumina run or 200-400 for a 1×300 bp Illumina run. Libraries can be extracted from the agarose following any standard protocol (i.e. Zymoclean Gel DNA Recovery Kit, D4001). Final sequencing libraries are quantified and pooled accordingly.

Data processing. RNA-seq. The first step in the ClickSeq processing pipeline is canonical, with an Illumina adaptor trimming step and quality filtering. In ClickSeq, the first four nucleotides read by the Illumina platform are the four random nucleotides included in the click-adaptor, which are designed to aid cluster generation and ensure diversity in these first nucleotides. The inventors have noticed that the fifth and sixth nucleotides tend to be read as either an "A" or "G". The inventors believe that this may be due to the Taq polymerase inserting a thymine opposite the triazole linkage that is present at this site in the click-linked cDNA as it may resemble an a basic site. Therefore, the inventors additionally trim the first 6 nucleotides from the beginning of each read. The inventors perform all of these raw-read processing steps with fastp [14] that can perform all these required actions and trim oligo-G tracts, as are commonly seen when using two-color sequencing systems such as the Illumina NextSeq using the following command-line entry:

(SEQ ID NO: 15)
fastp -i <input fastq> -a AGATCGGAAGAGC -f 6 -g
-l 40 -Q -o <output fastq>

PAC-seq. PAC-seq reads require careful preprocessing due to the frequent presence of long homo-A tracts derived from the poly(A) tails of the targeted mRNAs. In the example above, the pipeline for preprocessing was similar to that for randomly-primed ClickSeq reads, except in addition to Illumina adaptor trimming the inventors performed an additional adaptor trimming step to remove the poly-A tracts. In that pipeline, the inventors used a custom script (available at sourceforge.net/projects/dPAC-seq/) that compared the final trimmed reads to the raw data in order to measure how many 'A's had been removed from the read and added this information into the read name. In effect, this measures the length of the poly(A) tail that was successfully sequenced by the Illumina platform so that this information can later be used as a quality filtering metric when assigning the position of poly(A) sites. This step is important as the reverse-transcription oligo-dT primer may often mis-prime from non-cognate templates which would generate artifactual poly(A) sites. To control for this, PASs are filtered by only accepting those with reads mapping that contain a greater number of 'A's than the number of 'T's in the oligo-dT primer (>21) as these must be derived from the native and authentic poly(A) tail, rather than the RT-primer.

These filtering steps, while providing an accurate report of the position and frequency of PASs in mRNAs, results in the removal of a large number of mapped reads. In the example above, the inventors reported that approximately half of the raw reads were finally used to assign PASs after all filtering steps. For differential gene expression analysis, the goal is simply to determine how many reads map to mRNAs rather than find PASs. Therefore, these stringent filtering steps may remove a swath of data, and may also bias the output data to templates with longer poly(A) tails or to templates with a low 'A' content in the 3'UTR, as these would be more likely to terminate adjacent to the poly(A) tail. This has the further advantage in that shorter read lengths are suitable when selecting sequencing reagent kits. For PASs characterization, the inventors recommend at least 150 nt reads to obtain reads that are of sufficient length to capture a the 3'UTR as well as a sufficiently long portion of the poly(A) tail to allow quality filtering as described above. However, for DE-Seq, only short reads are required for an unambiguous mapping and so it is suitable to perform only 1×75 or shorter single-end sequencing. This therefore saves considerably on sequencing cost and time.

Therefore, the inventors developed a much simpler read preprocessing steps for DE analysis. First, the inventors perform the same processing steps as before (fastp filtering followed by poly(A) tail trimming using the FASTX toolkit) and then trim all the reads to a fixed length of 50-60 nucleotides without requiring reads to contain a poly(A) tail using the following command-line entries:
 1) fastp-i<input fastq> -a AGATCGGAAGAGC-f 6 -g -l 40 -Q -o <output fastq>
 2) fastp-i<input fastq> --disable_quality_filtering --trim_poly_x -a AAAAAAAAAAAAAAA—150 (SEQ ID NO:16)
 3) fastx_trimmer -Q33 -l 60 -i<input fastq> -o<output fastq>

Read alignment. For both random-primed ClickSeq and PAC-seq, short reads can be mapped to reference genomes using a number of available alignment software packages. When targeting eukaryotic mRNAs, the inventors recommend using splice-aware short-reads aligners such as STAR [15] or HiSat2[16]. The STAR aligner will account for annotated splice-sites that may be present in terminal exons and may be preferred when mapping very short reads (<75 nts in length). Similarly, HiSat2 will find de novo splice sites and so may be preferred when mapping longer reads (>75 nts) that can reliably map over splice events. Furthermore, these aligners will tolerate short soft-pads in the 3' ends of the mapped reads in case they over-run the end of reference transcript sequence and contain non-reference fragments of the poly(A) tail or the Illumina sequencing adaptors.

Transcript count assignment. Random-primed ClickSeq generates even coverage over entire mRNA transcripts. Therefore, to extract transcript abundance, read distribution must be normalized over the length of transcript, including factors such as GC content and bias in order to obtain a final count-per-transcript. For PAC-seq, transcript Annotated transcripts are obtained from the UCSC refseq [17] databases and output as BED files for the full-length transcript. The inventors next use the featureCounts command from the Subread suite [18] to return the number of reads mapping over individual transcripts. This returns a matrix of reads counts per annotated transcript for each RNA sample (example in Table 7), which can be used as an input for downstream DE-Seq pipelines.

Figure 9:
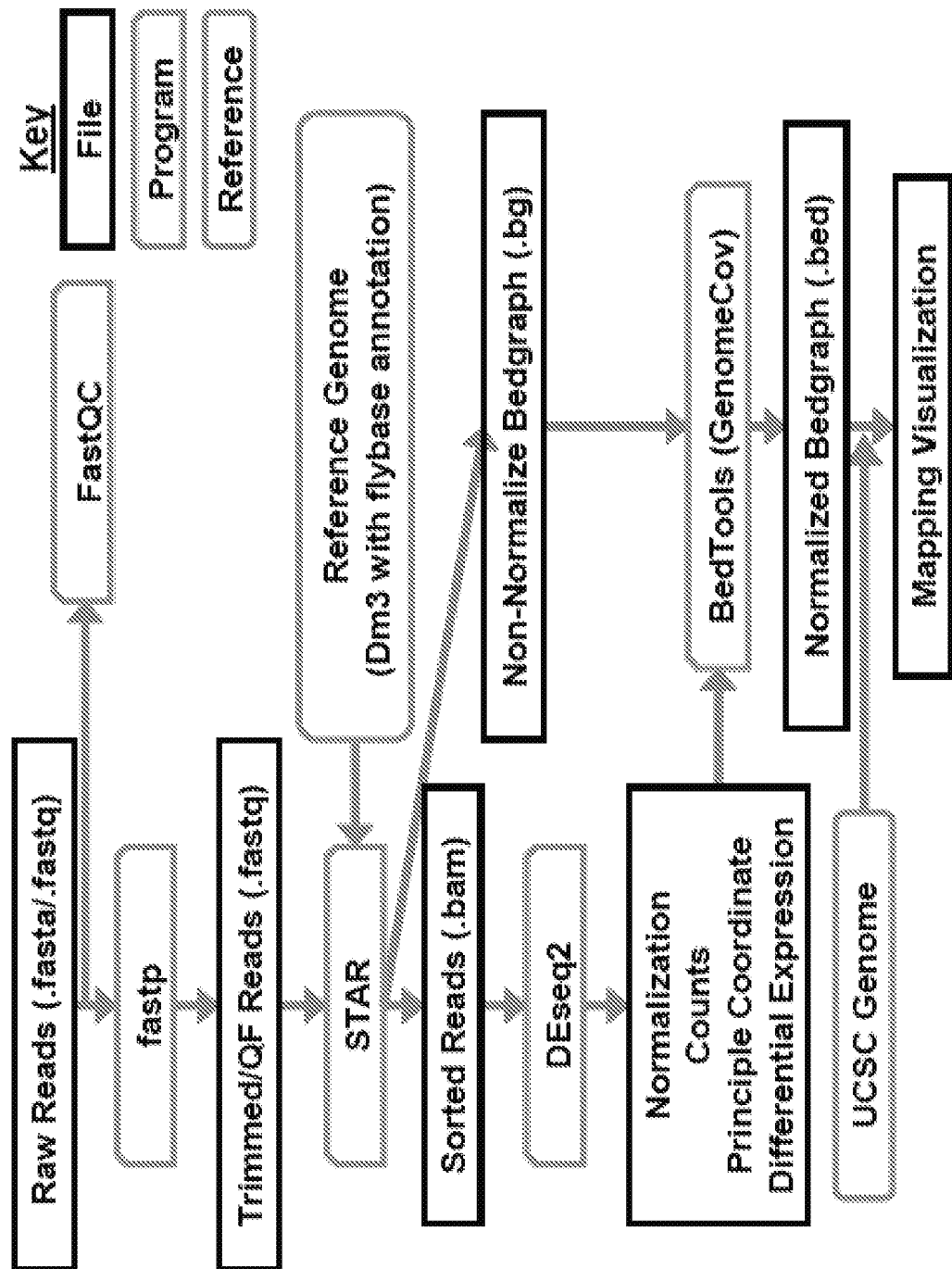
FIG. 9 is a flowchart of data analysis. Raw reads in fastq format are filtered and trimmed before alignment to the reference genome using STAR aligner. Sorted reads are then input to the DESeq2 pipeline following a matrix input format. This allows comparison of DE and normalized counts both through visualization by creating bedgraphs and fold change analysis.

PAC-seq directly from crude cellular RNA extracted from the cultured DL1 cells [2]. In parallel using the same samples, the inventors performed a poly(A) enrichment (NEBNext) to remove non-poly(A) tailed RNAs such as ribosomal RNAs and generated randomly-primed RNA ClickSeq libraries. This is a well-establish method of generating RNA-seq libraries that provides coverage across the length of the mRNA transcripts [20, 21] and allows to directly compare 3' end poly(A)-tail targeted methods for making NGS libraries versus random untargeted methods. Twelve libraries (2 methods×3 replicates×2 conditions) were submitted for sequencing on a NextSeq 550 for SE reads (1×75 for ClickSeq, 1×150 for PAC-Seq). The inventors obtained in the range of 10-30 million raw reads per library. Each of these libraries were trimmed and quality filtered as described in the methods (schematic illustrated in FIG. 9) to remove adaptor sequences, poly(A) tails, fragments of the click-adaptor, and any poor-quality base called reads.

Figure 10A:
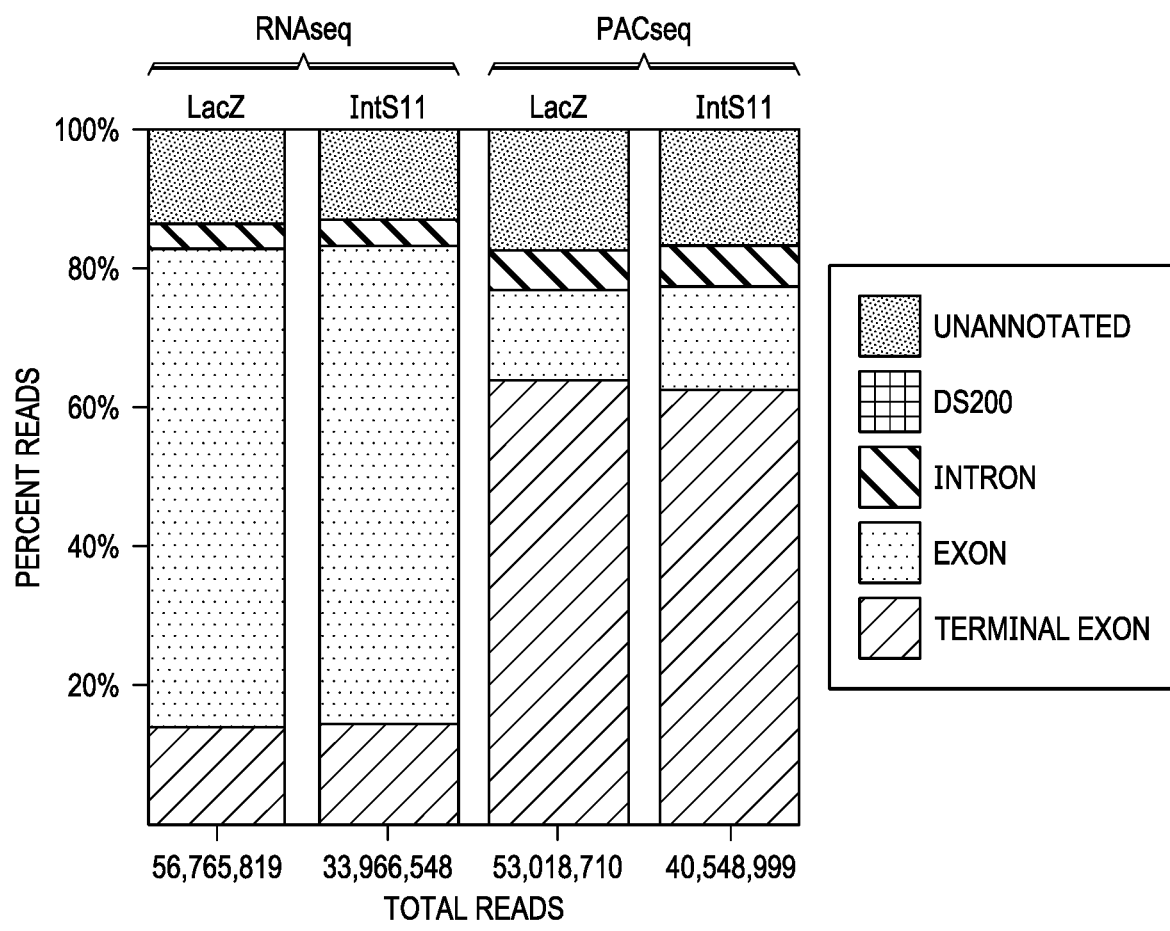
FIGS. 10A to 10D show examples of bedgraphs of outputs from data analysis.
Figure 10B:
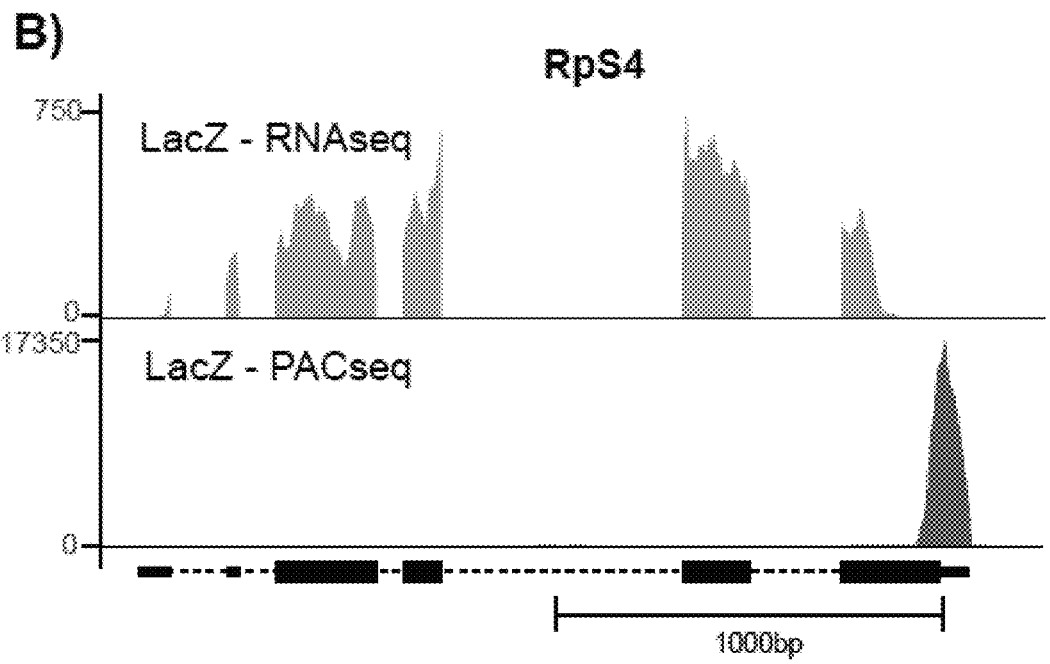

Alignment of NGS data and extraction of gene counts. Reads for each replicate (~10-22 million reads each) were mapped to the *Drosophila* reference genome (Dm3) using the STAR aligner[15], as described in materials and methods. The breakdown of the locations of read mapping is shown in FIG. 10A for each condition (SFig 1 for each replicate individually). In the random-primed ClickSeq (CS) libraries for both LacZ control and INTS11 knockdown samples, over 80% of all the mapped reads were located within or 200 nts downstream of annotated mRNAs. As illustrated in FIG. 10B with an example mRNA, RpS4,

TABLE 7

Read Counts in each RNA-seq and PACseq replicate associated with selected mRNAs (bold names shown in FIG. 10) in gene expression for each sample preparation method.

| Gene Name | RNA-seq Libraries | | | | | | PAC-seq Libraries | | | | | |
|---|---|---|---|---|---|---|---|---|---|---|---|---|
| | CS Z-1 | CS Z-2 | CS Z-3 | CS 11-1 | CS 11-2 | CS 11-3 | PAC Z-1 | PAC Z-2 | PAC Z-3 | PAC 11-1 | PAC 11-2 | PAC 11-3 |
| regucalcin | 66 | 174 | 58 | 1019 | 2163 | 1177 | 76 | 162 | 89 | 1743 | 2137 | 2761 |
| mgl | 114 | 158 | 134 | 2455 | 2503 | 1975 | 107 | 196 | 196 | 2756 | 2288 | 3858 |
| Col4a1 | 207 | 305 | 321 | 1112 | 1527 | 1172 | 127 | 137 | 199 | 704 | 1000 | 1261 |
| Arc1 | 7110 | 8664 | 8027 | 16028 | 23132 | 14556 | 15670 | 20101 | 24821 | 58040 | 71451 | 80399 |
| CG33926 | 513 | 665 | 590 | 865 | 1840 | 869 | 2944 | 4347 | 5395 | 8583 | 10598 | 13487 |
| Adgf-A | 1503 | 1946 | 1417 | 3237 | 4246 | 3022 | 493 | 603 | 700 | 1472 | 1087 | 2109 |
| Cys | 76 | 54 | 94 | 148 | 219 | 170 | 1907 | 2377 | 2862 | 4898 | 5252 | 7897 |
| spir | 3799 | 3896 | 3512 | 7323 | 6881 | 5053 | 1778 | 2015 | 2237 | 4822 | 3793 | 5074 |
| Su(Tpl) | 17119 | 17954 | 17963 | 10355 | 11170 | 8605 | 9901 | 10225 | 14267 | 9139 | 7060 | 11429 |
| CtBP | 12593 | 16444 | 14870 | 7198 | 9241 | 7114 | 16885 | 20821 | 25103 | 15024 | 14442 | 20559 |
| Ncoa6 | 12071 | 10237 | 9735 | 7376 | 6315 | 4814 | 4360 | 3797 | 4400 | 3875 | 2410 | 3979 |
| RpS4 | 8893 | 10246 | 10045 | 4250 | 5175 | 4228 | 20592 | 23793 | 29169 | 16447 | 13365 | 21986 |
| HmgZ | 6815 | 9213 | 9714 | 1816 | 2812 | 2207 | 14205 | 20442 | 24310 | 5954 | 6337 | 9735 |
| Tctp | 10700 | 15929 | 12795 | 1601 | 2967 | 1628 | 19428 | 31234 | 32365 | 4564 | 6905 | 8026 |
| IntS11 | 652 | 981 | 648 | 34 | 95 | 62 | 690 | 865 | 1172 | 15 | 30 | 47 |

Data availability. All batch scripts and associated scripts have been uploaded to sourceforge and are freely available and regularly maintained at: sourceforge.net/projects/DPAC-seq/). Raw data associated PRJNA498335.

Samples and NGS libraries. To compare the effect of knockdown of Integrator subunit 11 upon global transcript abundance, the inventors extracted total cellular RNA from DL1 cells that had Integrator 11 (INTS11) knocked-down using dsRNA and compared these to a control DL1 cells with a control knock-down to LacZ. This control was chosen to avoid observing changes in expression profiles that may be due to the delivery of dsRNA (e.g. innate immunity induction). To establish whether PAC-seq produces accurate and reproducible results in a differential gene expression analysis, the inventors prepared sequencing libraries using RNA-seq reads are distributed along the length of the mRNA transcripts, revealing exon splicing junctions, and occasionally mapping over known introns.

In Poly(A)-ClickSeq (PAC-seq), over 80% of all the mapped reads were similarly found within or 200 nts downstream of annotated mRNA FIG. 10A for each condition. However, the majority of these reads were found in the terminal exon, as would be expected when priming from the poly(A) tail of mRNAs. This is illustrated in FIG. 10B showing a large peak of read coverage extended from the annotated PAS into the 3'UTR, but not further in the gene body. This illustrates how PAC-seq can effectively and specifically sequence the 3' ends of mRNAs from crude cellular RNA extracts.

Figure 10C:
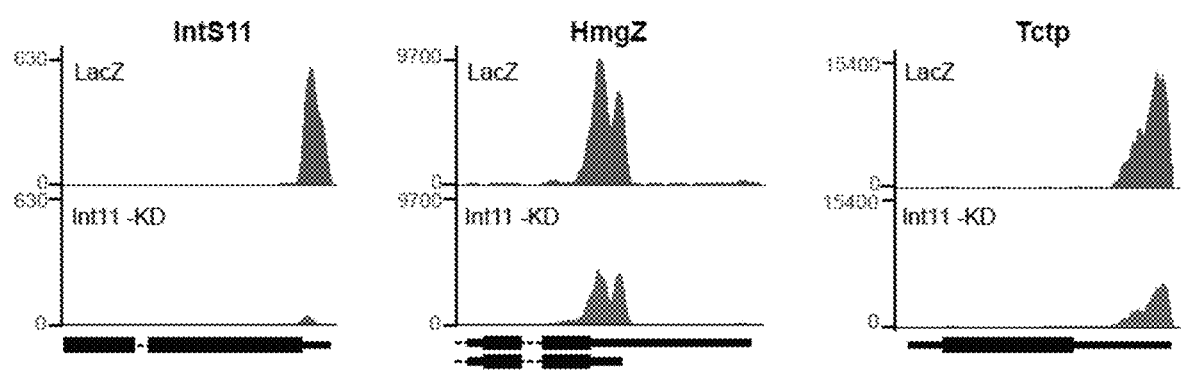
Figure 10D:
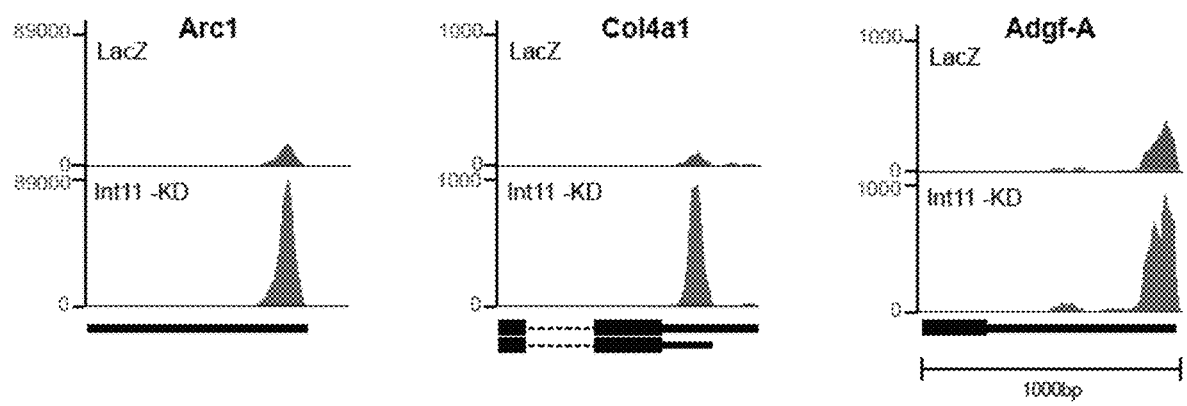

Differential gene expression pipeline and results. To determine whether PAC-seq can reliably reveal changes in gene expression, the inventors compared PAC-seq libraries coverage profiles between the control LacZ dsRNA treated cell and the INTS11 dsRNA cells. As expected, coverage of reads over the 3' UTR of INTS11 was substantially reduced (FIG. 10B and Table 7). Inspection of other genes also revealed numerous instances of gene down regulation upon INTS11 KD (FIG. 10B) as well as up regulation (FIG. 10C and Table 7).

To systematically measure changes in gene expression and perform DE, the inventors employed the DESeq2 pipeline for both the RNA-seq and PAC-seq data. For the RNA-seq data, replicates from each condition were normalized by calling the estimateSizeFactors command in the DESeq2 pipeline which uses a negative binomial distribution, linking variance and mean by local regression [22]. This resulted in normalization values that were in line with the differences in total number of read counts sequenced for each sample.

Figure 11A:
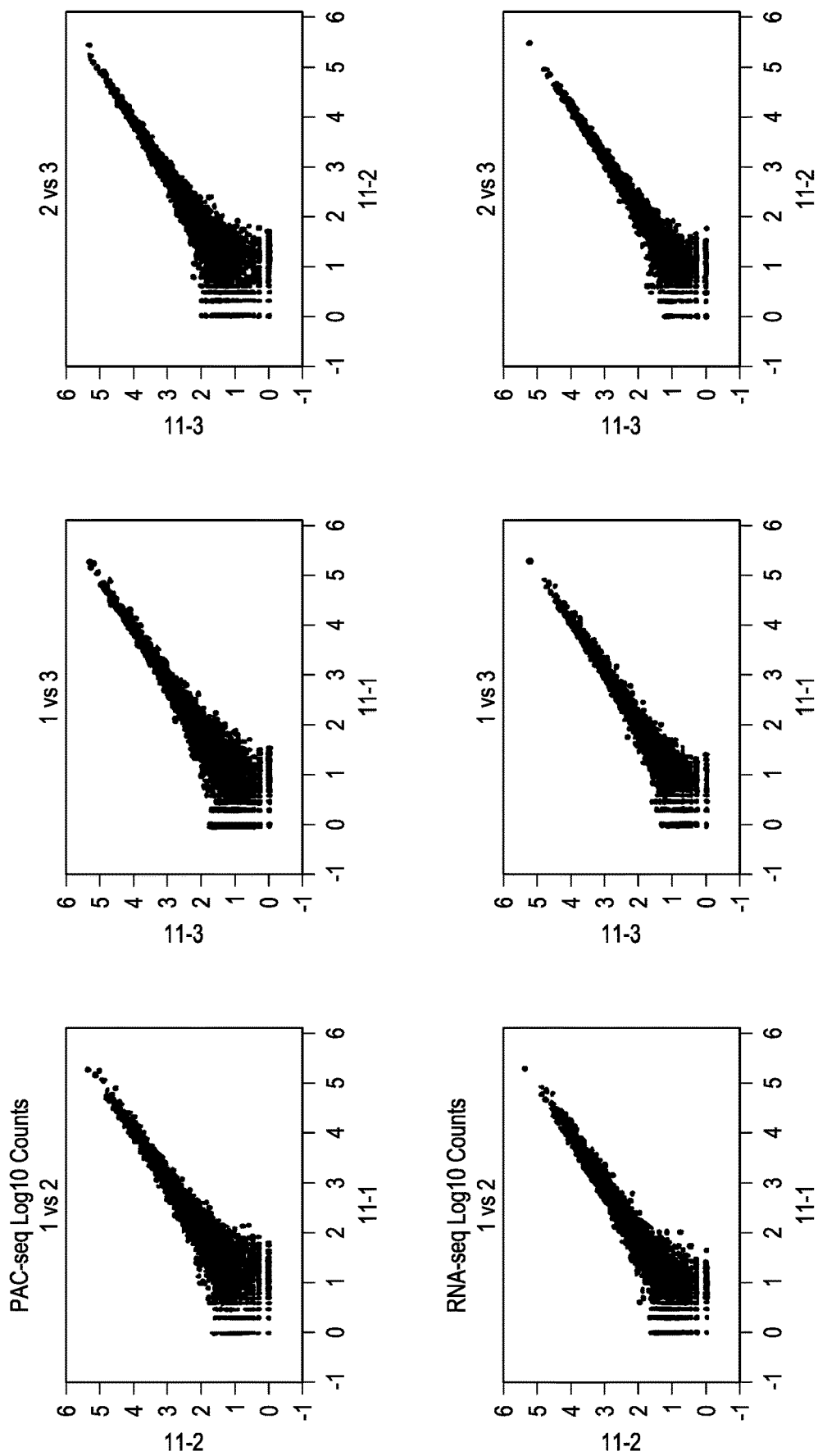
FIGS. 11A and 11B show a comparison of read counts between samples and preparation methods.
Figure 11B:
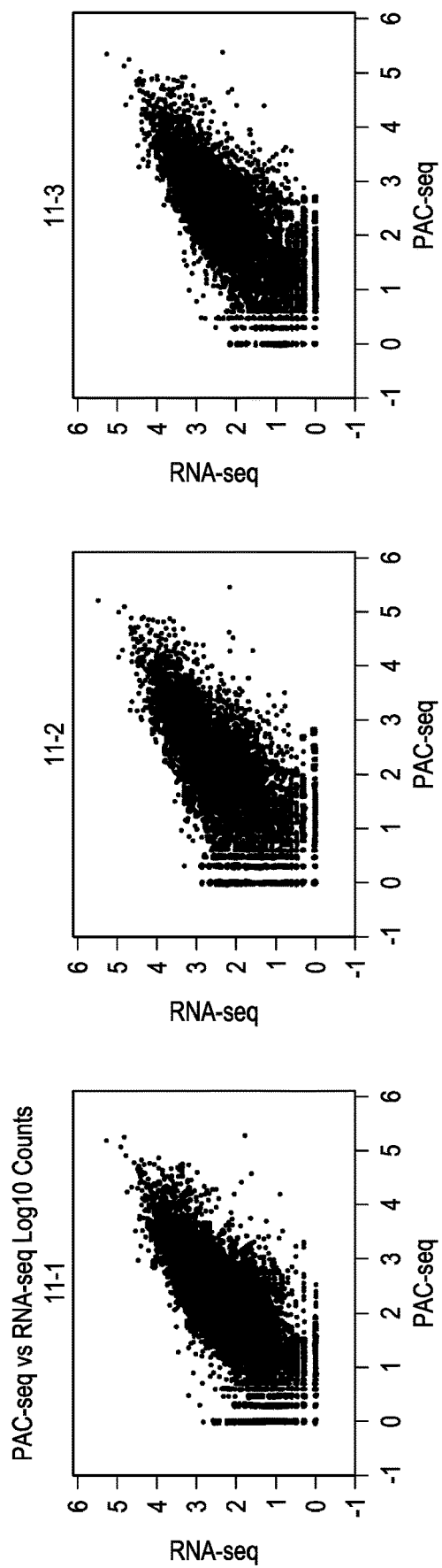

For RNA-seq, assignment of transcript abundance/count was performed using the featureCounts command. For PAC-seq, transcript abundance/count was equivalent to read coverage. Next, read counts were compared between samples within each preparation to ensure reproducibility of the techniques. Both PAC-seq and RNA-seq exhibited a high level of correlation between raw read counts within each preparation method with a Pearson's correlation coefficient of R2 greater than 0.9 for all comparisons of samples within methods (FIG. 11A). However, although there is good overall concordance, when examining the read counts between preparation methods there is some variance (FIG. 11B). This is likely due to the differences in preparation techniques. While PAC-seq specifically produces only one read per mRNA, traditional RNA-seq produces multiple fragments for each transcript that can be biased due to a number of factors including transcript length, GC content, and primer annealing conditions. Nonetheless, the high concordance between the individual replicates of each method indicates that these variances are reproducible and systematic.

Figure 12A:
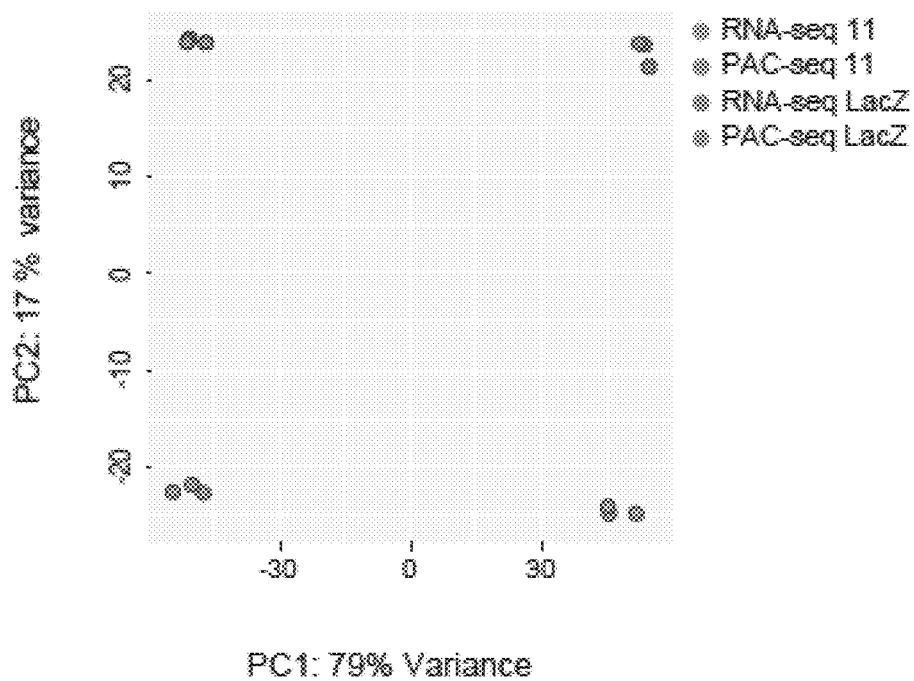
FIGS. 12A to 12D show output visualization of DESeq2 results.
Figure 12B:
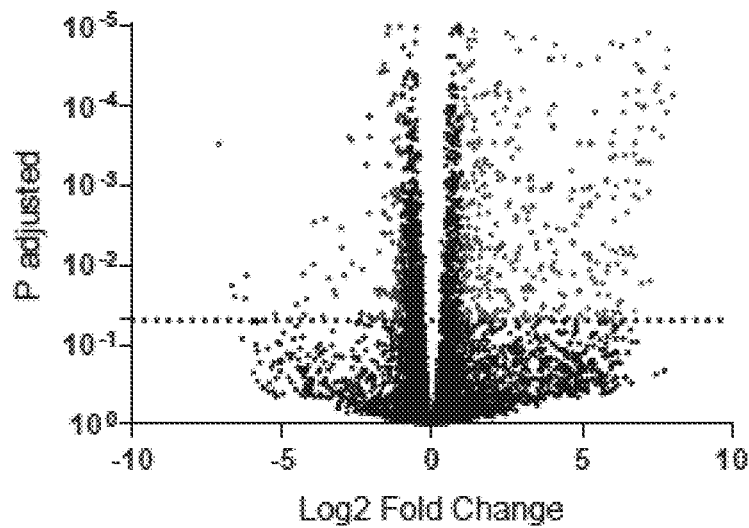
Figure 12C:
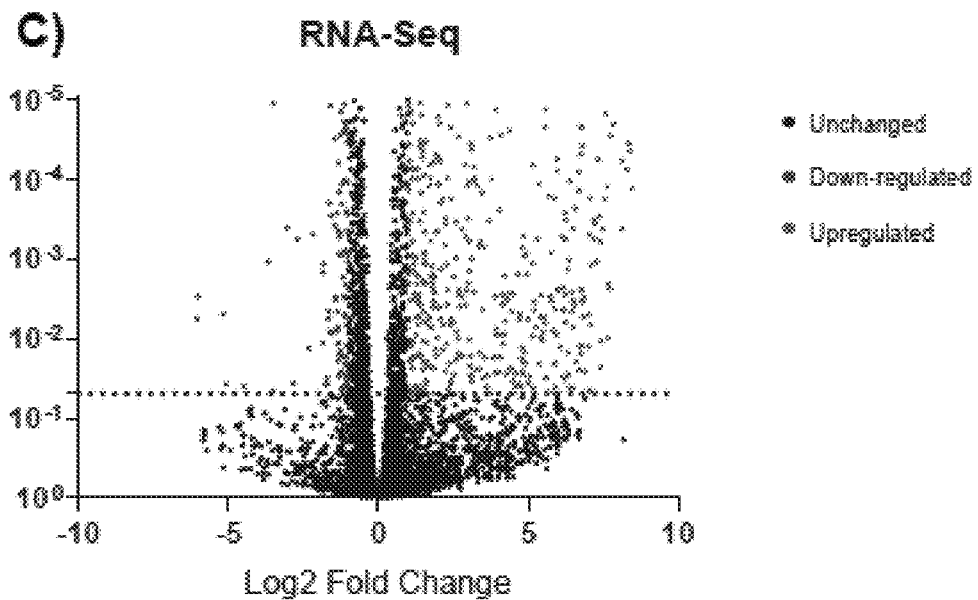

Transcript counts were used as input for the DESeq2 pipeline to measure differential expression. Principle Component Analysis of the four datasets (PAC vs Click and LacZ vs INT11) (FIG. 12A) show clear clustering of replicate experiments. As was expected, the CS libraries are strongly separated relative to the PAC-seq libraries along the first component (79% of variance), while the KD libraries are both separated along the second component (17% of variance). The tight clustering of sample types indicates a high level of confidence in reproducibility by both methods and the similar distance of knockdown effect gives high confidence in the changes detected. DE analysis revealed a global upregulation of mRNAs upon INTS11 KD with both techniques (FIGS. 12B and 12C). When requiring Bonferroni-adjusted p-values >0.05 and fold change in read count >2, 510 and 540 genes were upregulated and 110 and 141 were down-regulated for CS and PAC-seq respectively. At these statistic thresholds, it therefore appears that PAC-seq is capable of detecting a greater number of DE events, suggesting a greater sensitivity.

Figure 12D:
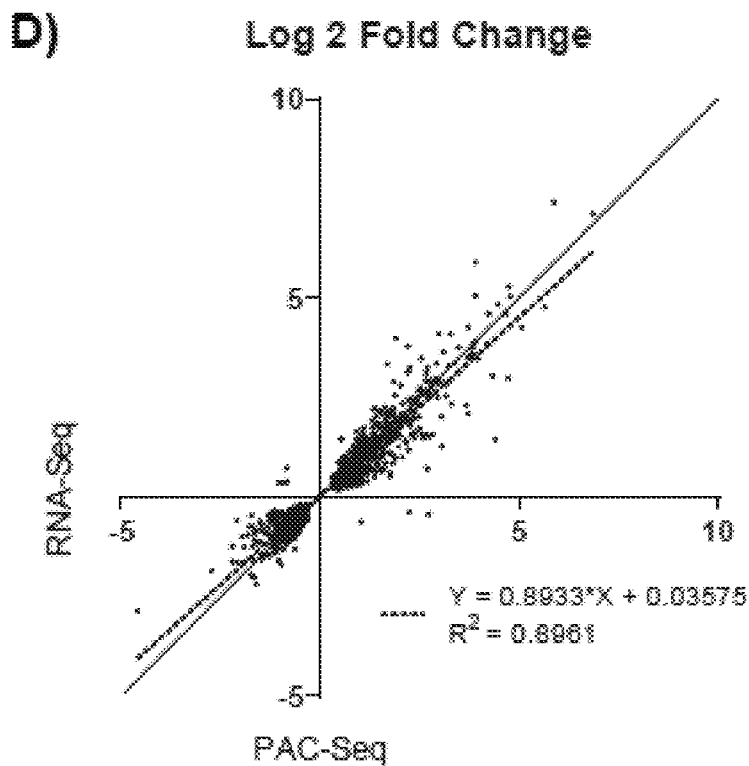

An example of the output data is shown in Table 8 for genes that were upregulated, unchanged, and down-regulated upon INTS11 knockdown. This table demonstrates the high level of correlation between PAC-seq and RNA-seq with respect to the fold changes in each gene. The fold change for mRNAs with adjusted p-values <0.05 are shown in the scatter plot in FIG. 12D. The Fold Change trends along the x=y axis with a Pearson correlation co-efficient of R2=0.8961 (p<0.0001) indicating that PAC-seq and RNA-seq perform similarly in estimation of overall changes in gene expression between two conditions and there is general agreement between the two sequencing techniques. Interestingly, these fold changes correspond well irrespective of variance in the number of read counts detected by each method. There was a minor difference in the fold change of INTS11 expression due to a number of reads detected in RNA-seq data for the region targeted by the INTS11 dsRNA for knockdown even though the total RNA was purified using Oligo(dT) beads. This indicated contaminating presence of these RNA molecules that were able to carry over with the beads and a possible shortcoming of the RNA-seq method.

TABLE 8

DESeq2 output for RNA-seq and PAC-seq replicates (bold names shown in FIG. 10)

| Gene | RNA-seq Z mean | RNA-seq INT11 | RNA-seq log2 Fold Change | RNA-seq p-adjusted | PAC-seq Z mean | PAC-seq INT11 mean | PAC-seq log2 Fold Change | PAC-seq p-adjusted |
|---|---|---|---|---|---|---|---|---|
| regucalcin | 55.68 | 1354.87 | 4.60 | 1.08E−41 | 124.67 | 3143.08 | 4.66 | 3.51E−43 |
| mgl | 78.04 | 2233.50 | 4.84 | 3.28E−170 | 185.38 | 4140.88 | 4.48 | 2.10E−150 |
| Col4a1 | 160.37 | 1216.72 | 2.92 | 3.98E−40 | 172.92 | 1402.62 | 3.02 | 1.05E−40 |
| Arc1 | 4593.57 | 16986.00 | 1.89 | 1.90E−35 | 22642.76 | 100741.45 | 2.15 | 2.40E−46 |
| CG33926 | 340.56 | 1103.87 | 1.70 | 2.21E−16 | 4701.16 | 15483.25 | 1.72 | 1.50E−17 |
| Adgf-A | 935.20 | 3347.50 | 1.84 | 6.14E−48 | 675.81 | 2148.53 | 1.67 | 4.54E−37 |
| Cys | 44.00 | 171.21 | 1.97 | 9.13E−21 | 2679.45 | 8433.48 | 1.65 | 1.45E−21 |
| spir | 2171.39 | 6202.61 | 1.51 | 2.41E−18 | 2286.26 | 6525.54 | 1.51 | 3.27E−18 |
| Su(Tpl) | 10280.56 | 9682.88 | −0.09 | 7.42E−01 | 12916.78 | 12933.92 | 0.00 | 9.95E−01 |
| CtBP | 8458.02 | 7533.67 | −0.17 | 2.77E−01 | 23563.77 | 23577.10 | 0.00 | 9.97E−01 |
| Ncoa6 | 6241.29 | 5984.12 | −0.06 | 9.14E−01 | 4829.10 | 4829.54 | 0.00 | 1.00E+00 |
| RpS4 | 5643.40 | 4383.64 | −0.36 | 1.46E−03 | 27673.26 | 24171.62 | −0.20 | 1.46E−01 |
| HmgZ | 4964.61 | 2177.84 | −1.19 | 1.62E−13 | 21941.21 | 10271.61 | −1.10 | 1.29E−11 |
| Tctp | 7560.20 | 1933.95 | −1.97 | 8.22E−21 | 30985.18 | 9291.25 | −1.74 | 1.79E−16 |
| IntS11 | 436.22 | 59.52 | −2.87 | 3.76E−20 | 1014.07 | 42.20 | −4.58 | 3.50E−45 |

Differential gene expression analysis is routine and widespread in the biomedical sphere. In typical RNA-seq approaches for DE analyses, to achieve sufficient depth and sensitivity while obtaining a sufficient number of biological and technical replicates, a large volume of next-generation sequencing data must be acquired often at a considerable cost. Therefore, 3'end targeted methods of estimating gene abundance are becoming viewed as cost-effective alternatives to standard RNA-seq. These approaches generate a simplified snapshot of the transcriptome and so miss many important factors in understanding transcriptome diversity, such as the presence of transcript isoforms and splice variants.

Nonetheless, there have recently been a number of approaches developed for the identification of 3'ends of poly-adenylated transcripts (reviewed in [23]). However, among the simplest strategies employing the fewest manipulations are the QuantSeq[5] and the Poly(A)-ClickSeq (PAC-seq) pipeline. The inventors have previously demonstrated how PAC-seq can be used to locate and quantify the poly(A) sites of mRNAs and measure changes in poly(A) tail positions upon manipulation of the cleavage and polyadenylation machinery and described how this reveals the regulation of poly(A) site selection by CFI25 m [2]. Alternative poly-adenylation (APA) is emerging as a critical factor in the regulation of mRNA translation efficiency and transcript stability[24]. Furthermore, 3'UTR shortening has been clearly associated with a number of disease states such as glioblastoma [25].

In this example, the inventors have demonstrated that PAC-seq simultaneously provides a simple and cost-effective strategy for measuring absolute levels and relative changes in gene expression, thus providing a dual-use tool. When compared side-by-side to random-primed RNA-seq of poly(A)-enriched mRNA, the inventors demonstrated that PAC-seq can capture changes in gene expression in good agreement with the RNA-seq data, despite only sequencing a fraction of the mRNA terminal exon. Additionally, PAC-seq detects a greater number of genes that display significant (adjusted $p<0.05$) changes in expression level. This is achieved without the need for any sample preparation or target enrichment. Rather, crude cellular RNA is used as an input for the library preparation. This simplifies the process, and also removes the biases and cost that may be imparted by these sample treatments.

In general, there are numerous advantages to employing a 3'end targeted sequencing methods such as PAC-seq for characterizing quantitative changes in the transcriptome by NGS: (1) By only sequencing the 3'end of an mRNA transcript, sequencing depth is limited to one read per transcript. This saves on the amount of sequencing that must be performed when compared to standard RNA-seq where reads may be found across the length of the RNA transcript. It is possible, but not a limitation of the present invention, that with this method that a poly(A) tail is in fact primed twice, and that a lagging reverse transcriptase strand-displaces the upstream cDNA [26]. This would generate two cDNAs (or more) from a single mRNA. However, this would only be likely for very long poly(A) tails, which are scarce. (2) As all transcripts only have one poly(A) tail, this negates the need for computational normalization of read counts assigned to a mRNA as a function of their length. This process is normally complicated by the presence of alternative splice variants as well as incomplete annotation in some reference genomes. (3) Very small transcripts that would otherwise receive very low sequence coverage in standard RNA-seq approaches and may be missed can be accurately quantified in an equivalent manner to longer transcripts when using PAC-seq. (4) Long poly(A) tails are generally found only on mature mRNA transcripts rather than transcripts undergoing nascent transcription, which may contain introns or arise as a result of abortive transcription, which would not represent translating mRNAs. (5) If ribo-depletion were employed rather than poly(A) tail selection, RNA-seq would sequence a large amount of non-mRNA material including transposable elements and ncRNAs. Unless these transcripts were poly-adenylated, they would not be detected by PAC-seq.

PAC-seq strength lies in its property of focusing solely on the 3' end of mRNA transcripts in order to estimate RNA abundance. However, for some transcripts, this may expose a vulnerability in scenarios where the 3' UTR of a specific mRNA is highly structured, has unusual nucleotide composition, or contains some other intrinsic property that reduces or inhibits reverse transcription. In these cases, the abundance of these transcripts may be under-estimated relative to other transcripts. However, this limitation can be overcome by varying RT conditions and/or using highly processive RT enzymes such as Superscript IV or TGIRT. However, for the purposes of DE analysis, small biases in 3' end sequencing would likely be similar between multiple replicates of the same terminal exon and therefore would be accounted for when measuring DE.

By sequencing only the 3'ends of transcripts, computational pipelines for estimating gene abundance and determining changes in gene expression are greatly simplified and streamlined, as demonstrated in this manuscript. However, there remain two key disadvantages. Firstly; there is a small probability that the 3'end of some transcripts are identical to one another (e.g. between paralogs, duplicated genes and pseudo-genes). This would result in ambiguous mapping of the PAC-seq reads where standard RNA-seq would take advantage of SNPs found throughout the transcript in order to assign isoform/paralog abundance [28]. Secondly, due to the PCR cycles required for RNA-seq library construction, PCR duplication is a common artifact in RNA-seq libraries that may return erroneous and aberrant estimates of gene abundance. This artifact can be overcome computationally by using de-duplication methods that collapse multiple reads into a single read if they share the same start and stop sites in the reference genome. This may lose some reads that coincidently had the same mapping positions, but these cases are infrequent when read coverage is not excessive. However, in PAC-seq, all reads are enriched in a small portion of the mRNA transcript (usually the terminal exon) and so the probability of two reads having the same mapping coordinates becomes very high. Therefore, standard computational de-duplication cannot be employed. However, unique molecular identifiers [29] can easily be appended to the beginning of the click-adaptor providing a more robust method for collapsing identical reads.

In addition to priming from the poly(A) tail during RT-PCR, priming from A-rich sequences within mRNAs is also possible when using an oligo-dT primer. This may result in absolute read counts being elevated for particular transcripts. However, the inventors would expect the frequency of internal priming from A-rich tracts to correlate with gene abundance and be conserved among multiple replicates. Therefore, this factor would not perturb differential gene expression analysis. In PAC-Seq, as priming is not anchored to the 3'UTR/poly(A) tail junction, small portions of the poly(A)-tail are copied yielding non-primer derived A's in the final read data. These extra A's allow us to control for internal and/or mis-priming by requiring a greater number of A's in a mapped read than were T's used in the oligo-dT primer thus allowing confident annotation of poly(A)-sites. Moreover, in the absence of this control (e.g. when using short reads), internal priming can also be ameliorated by only counting reads that map to the expected 3' terminal exons of mRNA transcripts when determining transcript abundance.

The inventors demonstrate the unique features of techniques such as PAC-seq that lend themselves to be critical tools in high-volume investigations (large sample numbers with multiple repeats) requiring analysis of gene abundance or changes in expression. Additionally, PAC-seq may be broadly applicable for the detection and titering of other poly(A) tailed species such as positive sense RNA viruses. PAC-seq provides a robust and highly scalable method for both PAS annotation and gene expression analysis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES—EXAMPLE 1

1. Proudfoot, N. J. (2011) Ending the message: poly(A) signals then and now. Genes Dev, 25, 1770-1782.
2. Kempf, B. J. and Barton, D. J. (2015) Picornavirus RNA polyadenylation by 3D(pol), the viral RNA-dependent RNA polymerase. Virus Res, 206, 3-11.

3. Wilusz, J. (2013) Putting an 'End' to HIV mRNAs: capping and polyadenylation as potential therapeutic targets. AIDS Res Ther, 10, 31.
4. Sheets, M. D., Ogg, S. C. and Wickens, M. P. (1990) Point mutations in AAUAAA and the poly (A) addition site: effects on the accuracy and efficiency of cleavage and polyadenylation in vitro. Nucleic Acids Res., 18, 5799-5805.
5. Hu, J., Lutz, C. S., Wilusz, J. and Tian, B. (2005) Bioinformatic identification of candidate cis-regulatory elements involved in human mRNA polyadenylation. RNA, 11, 1485-1493.
6. Xiang, K., Tong, L. and Manley, J. L. (2014) Delineating the structural blueprint of the pre-mRNA 3'-end processing machinery. Mol Cell Biol, 34, 1894-1910.
7. Tian, B. and Manley, J. L. (2016) Alternative polyadenylation of mRNA precursors. Nat Rev Mol Cell Biol.
8. Zhang, H., Lee, J. Y. and Tian, B. (2005) Biased alternative polyadenylation in human tissues. Genome Biol, 6, R100.
9. Di Giammartino, D. C., Nishida, K. and Manley, J. L. (2011) Mechanisms and consequences of alternative polyadenylation. Mol Cell, 43, 853-866.
10. Shi, Y. (2012) Alternative polyadenylation: new insights from global analyses. RNA, 18, 2105-2117.
11. Jan, C. H., Friedman, R. C., Ruby, J. G. and Bartel, D. P. (2011) Formation, regulation and evolution of *Caenorhabditis elegans* 3'UTRs. Nature, 469, 97-101.
12. Ji, Z., Lee, J. Y., Pan, Z., Jiang, B. and Tian, B. (2009) Progressive lengthening of 3' untranslated regions of mRNAs by alternative polyadenylation during mouse embryonic development. Proc Natl Acad Sci USA, 106, 7028-7033.
13. Lianoglou, S., Garg, V., Yang, J. L., Leslie, C. S. and Mayr, C. (2013) Ubiquitously transcribed genes use alternative polyadenylation to achieve tissue-specific expression. Genes Dev, 27, 2380-2396.
14. Miura, P., Shenker, S., Andreu-Agullo, C., Westholm, J. O. and Lai, E. C. (2013) Widespread and extensive lengthening of 3' UTRs in the mammalian brain. Genome Res, 23, 812-825.
15. Hollerer, I., Curk, T., Haase, B., Benes, V., Hauer, C., Neu-Yilik, G., Bhuvanagiri, M., Hentze, M. W. and Kulozik, A. E. (2016) The differential expression of alternatively polyadenylated transcripts is a common stress-induced response mechanism that modulates mammalian mRNA expression in a quantitative and qualitative fashion. RNA, 22, 1441-1453.
16. Mayr, C. and Bartel, D. P. (2009) Widespread shortening of 3'UTRs by alternative cleavage and polyadenylation activates oncogenes in cancer cells. Cell, 138, 673-684.
17. Sandberg, R., Neilson, J. R., Sarma, A., Sharp, P. A. and Burge, C. B. (2008) Proliferating cells express mRNAs with shortened 3' untranslated regions and fewer microRNA target sites. Science, 320, 1643-1647.
18. Elkon, R., Drost, J., van Haaften, G., Jenal, M., Schrier, M., Vrielink, J. A. and Agami, R. (2012) E2F mediates enhanced alternative polyadenylation in proliferation. Genome Biol, 13, R59.
19. Wood, A. J., Schulz, R., Woodfine, K., Koltowska, K., Beechey, C. V., Peters, J., Bourc'his, D. and Oakey, R. J. (2008) Regulation of alternative polyadenylation by genomic imprinting. Genes Dev, 22, 1141-1146.
20. Blair, L. P., Liu, Z., Labitigan, L. R., Wu, L., Zheng, D., Xia, Z., Pearson, E. L., Nazeer, F. I., Cao, J., Lang, S. M. et al. (2016) KDM5 lysine demethylases are involved in maintenance of 3'UTR length. Science Advances, 2.
21. Oktaba, K., Zhang, W., Lotz, T. S., Jun, D. J., Lemke, S. B., Ng, S. P., Esposito, E., Levine, M. and Hilgers, V. (2015) ELAV links paused Pol II to alternative polyadenylation in the *Drosophila* nervous system. Mol Cell, 57, 341-348.
22. Jenal, M., Elkon, R., Loayza-Puch, F., van Haaften, G., Kuhn, U., Menzies, F. M., Oude Vrielink, J. A., Bos, A. J., Drost, J., Rooijers, K. et al. (2012) The poly(A)-binding protein nuclear 1 suppresses alternative cleavage and polyadenylation sites. Cell, 149, 538-553.
23. Kubo, T., Wada, T., Yamaguchi, Y., Shimizu, A. and Handa, H. (2006) Knock-down of 25 kDa subunit of cleavage factor Im in Hela cells alters alternative polyadenylation within 3'-UTRs. Nucleic Acids Res, 34, 6264-6271.
24. Martin, G., Gruber, A. R., Keller, W. and Zavolan, M. (2012) Genome-wide analysis of pre-mRNA 3' end processing reveals a decisive role of human cleavage factor I in the regulation of 3' UTR length. Cell reports, 1, 753-763.
25. Takagaki, Y., Seipelt, R. L., Peterson, M. L. and Manley, J. L. (1996) The polyadenylation factor CstF-64 regulates alternative processing of IgM heavy chain pre-mRNA during B cell differentiation. Cell, 87, 941-952.
26. Lackford, B., Yao, C., Charles, G. M., Weng, L., Zheng, X., Choi, E. A., Xie, X., Wan, J., Xing, Y., Freudenberg, J. M. et al. (2014) Fip1 regulates mRNA alternative polyadenylation to promote stem cell self-renewal. EMBO J, 33, 878-889.
27. Seoane, S., Lamas-Maceiras, M., Rodriguez-Torres, A. M. and Freire-Picos, M. A. (2009) Involvement of Pta1, Pcf11 and a K1CYC1 AU-rich element in alternative RNA 3'-end processing selection in yeast. FEBS Lett, 583, 2843-2848.
28. Gruber, A. R., Martin, G., Keller, W. and Zavolan, M. (2012) Cleavage factor Im is a key regulator of 3' UTR length. RNA Biol, 9, 1405-1412.
29. Thomas, P. E., Wu, X., Liu, M., Gaffney, B., Ji, G., Li, Q. Q. and Hunt, A. G. (2012) Genome-wide control of polyadenylation site choice by CPSF30 in *Arabidopsis*. Plant Cell, 24, 4376-4388.
30. Yao, C., Biesinger, J., Wan, J., Weng, L., Xing, Y., Xie, X. and Shi, Y. (2012) Transcriptome-wide analyses of CstF64-RNA interactions in global regulation of mRNA alternative polyadenylation. Proc Natl Acad Sci USA, 109, 18773-18778.
31. Masamha, C. P., Xia, Z., Yang, J., Albrecht, T. R., Li, M., Shyu, A.-B., Li, W. and Wagner, E. J. (2014) CFIm25 links alternative polyadenylation to glioblastoma tumour suppression. Nature, 510, 412-416.
32. O'Grady, T., Wang, X., Honer Zu Bentrup, K., Baddoo, M., Concha, M. and Flemington, E. K. (2016) Global transcript structure resolution of high gene density genomes through multi-platform data integration. Nucleic Acids Res, 44, e145.
33. Xia, Z., Donehower, L. A., Cooper, T. A., Neilson, J. R., Wheeler, D. A., Wagner, E. J. and Li, W. (2014) Dynamic analyses of alternative polyadenylation from RNA-seq reveal a 3'-UTR landscape across seven tumour types. Nat Commun, 5.
34. Hogue, M., Ji, Z., Zheng, D., Luo, W., Li, W., You, B., Park, J. Y., Yehia, G. and Tian, B. (2013) Analysis of alternative cleavage and polyadenylation by 3' region extraction and deep sequencing. Nature methods, 10, 133-139.

35. Ma, L., Pati, P. K., Liu, M., Li, Q. Q. and Hunt, A. G. (2014) High throughput characterizations of poly(A) site choice in plants. Methods, 67, 74-83.
36. Mangone, M., Manoharan, A. P., Thierry-Mieg, D., Thierry-Mieg, J., Han, T., Mackowiak, S. D., Mis, E., Zegar, C., Gutwein, M. R., Khivansara, V. et al. (2010) The landscape of C. elegans 3'UTRs. Science, 329, 432-435.
37. Mata, J. (2013) Genome-wide mapping of polyadenylation sites in fission yeast reveals widespread alternative polyadenylation. RNA Biol, 10, 1407-1414.
38. Ozsolak, F., Kapranov, P., Foissac, S., Kim, S. W., Fishilevich, E., Monaghan, A. P., John, B. and Milos, P. M. (2010) Comprehensive polyadenylation site maps in yeast and human reveal pervasive alternative polyadenylation. Cell, 143, 1018-1029.
39. Shepard, P. J., Choi, E.-A., Lu, J., Flanagan, L. A., Hertel, K. J. and Shi, Y. (2011) Complex and dynamic landscape of RNA polyadenylation revealed by PAS-Seq. RNA, 17, 761-772.
40. Zheng, D., Liu, X. and Tian, B. (2016) 3'READS+, a sensitive and accurate method for 3' end sequencing of polyadenylated RNA. RNA, 22, 1631-1639.
41. Chang, H., Lim, J., Ha, M. and Kim, V. N. (2014) TAIL-seq: genome-wide determination of poly(A) tail length and 3' end modifications. Mol Cell, 53, 1044-1052.
42. Routh, A., Head, S. R., Ordoukhanian, P. and Johnson, J. E. (2015) ClickSeq: Fragmentation-Free Next-Generation Sequencing via Click Ligation of Adaptors to Stochastically Terminated 3'-Azido cDNAs. J Mol Biol, 427, 2610-2616.
43. Masamha, C. P., Xia, Z., Yang, J., Albrecht, T. R., Li, M., Shyu, A. B., Li, W. and Wagner, E. J. (2014) CFIm25 links alternative polyadenylation to glioblastoma tumour suppression. Nature, 510, 412-416.
44. Martin, M. (2011) Cutadapt removes adapter sequences from high-throughput sequencing reads. EMBnet.journal, 17, 10-12.
45. Kim, D., Langmead, B. and Salzberg, S. L. (2015) HISAT: a fast spliced aligner with low memory requirements. Nature methods, 12, 357-360.
46. Li, H., Handsaker, B., Wysoker, A., Fennell, T., Ruan, J., Homer, N., Marth, G., Abecasis, G. and Durbin, R. (2009) The Sequence Alignment/Map format and SAMtools. Bioinformatics, 25, 2078-2079.
47. Bailey, T. L. (2011) DREME: motif discovery in transcription factor ChIP-seq data. Bioinformatics, 27, 1653-1659.
48. Bailey, T. L. and Machanick, P. (2012) Inferring direct DNA binding from ChIP-seq. Nucleic Acids Res, 40, e128.
49. Kolb, H. C., Finn, M. G. and Sharpless, K. B. (2001) Click Chemistry: Diverse Chemical Function from a Few Good Reactions. Angew Chem Int Ed Engl, 40, 2004-2021.
50. Isobe, H., Fujino, T., Yamazaki, N., Guillot-Nieckowski, M. and Nakamura, E. (2008) Triazole-linked analogue of deoxyribonucleic acid ((TL)DNA): design, synthesis, and double-strand formation with natural DNA. Org Lett, 10, 3729-3732.
51. Routh, A., Chang, M. W., Okulicz, J. F., Johnson, J. E. and Torbett, B. E. (2015) CoVaMa: Co-Variation Mapper for disequilibrium analysis of mutant loci in viral populations using next-generation sequence data. Methods.
52. Derti, A., Garrett-Engele, P., Macisaac, K. D., Stevens, R. C., Sriram, S., Chen, R., Rohl, C. A., Johnson, J. M. and Babak, T. (2012) A quantitative atlas of polyadenylation in five mammals. Genome Res, 22, 1173-1183.
53. Schurch, N. J., Schofield, P., Gierlinski, M., Cole, C., Sherstnev, A., Singh, V., Wrobel, N., Gharbi, K., Simpson, G. G., Owen-Hughes, T. et al. (2016) How many biological replicates are needed in an RNA-seq experiment and which differential expression tool should you use? RNA, 22, 839-851.
54. Hsu, F., Kent, W. J., Clawson, H., Kuhn, R. M., Diekhans, M. and Haussler, D. (2006) The UCSC Known Genes. Bioinformatics, 22, 1036-1046.
55. Zhang, H., Hu, J., Recce, M. and Tian, B. (2005) PolyA_DB: a database for mammalian mRNA polyadenylation. Nucleic Acids Res, 33, D116-120.
56. Yang, Q., Coseno, M., Gilmartin, G. M. and Doublié, S. (2011) Crystal Structure of a Human Cleavage Factor CFIm25/CFIm68/RNA Complex Provides an Insight into Poly(A) Site Recognition and RNA Looping. Structure (London, England: 1993), 19, 368-377.
57. Beaudoing, E., Freier, S., Wyatt, J. R., Claverie, J.-M. and Gautheret, D. (2000) Patterns of Variant Polyadenylation Signal Usage in Human Genes. Genome Res., 10, 1001-1010.
58. Chen, J., Ezzeddine, N., Waltenspiel, B., Albrecht, T. R., Warren, W. D., Marzluff, W. F. and Wagner, E. J. (2012) An RNAi screen identifies additional members of the Drosophila Integrator complex and a requirement for cyclin C/Cdk8 in snRNA 3'-end formation. RNA, 18, 2148-2156.
59. Chen, J., Waltenspiel, B., Warren, W. D. and Wagner, E. J. (2013) Functional analysis of the integrator subunit 12 identifies a microdomain that mediates activation of the Drosophila integrator complex. J Biol Chem, 288, 4867-4877.
60. Ezzeddine, N., Chen, J., Waltenspiel, B., Burch, B., Albrecht, T., Zhuo, M., Warren, W. D., Marzluff, W. F. and Wagner, E. J. (2011) A subset of Drosophila integrator proteins is essential for efficient U7 snRNA and spliceosomal snRNA 3'-end formation. Mol Cell Biol, 31, 328-341.
61. Sullivan, K. D., Mullen, T. E., Marzluff, W. F. and Wagner, E. J. (2009) Knockdown of SLBP results in nuclear retention of histone mRNA. Rna, 15, 459-472.
62. Wagner, E., Burch, B., Godfrey, A., Salzler, H., Duronio, R. and Marzluff, W. (2007) A genome-wide RNA interference screen reveals that variant histones are necessary for replication-dependent histone pre-mRNA processing. Mol Cell, 28, 692-699.
63. Smibert, P., Miura, P., Westholm, J. O., Shenker, S., May, G., Duff, M. O., Zhang, D., Eads, B. D., Carlson, J., Brown, J. B. et al. (2012) Global patterns of tissue-specific alternative polyadenylation in Drosophila. Cell reports, 1, 277-289.
64. Jabara, C. B., Jones, C. D., Roach, J., Anderson, J. A. and Swanstrom, R. (2011) Accurate sampling and deep sequencing of the HIV-1 protease gene using a Primer ID. Proc Natl Acad Sci USA, 108, 20166-20171.
65. Derti, A., Garrett-Engele, P., Macisaac, K. D., Stevens, R. C., Sriram, S., Chen, R., Rohl, C. A., Johnson, J. M. and Babak, T. (2012) A quantitative atlas of polyadenylation in five mammals. Genome Res, 22, 1173-1183.
66. Kim, D., Langmead, B. and Salzberg, S. L. (2015) HISAT: a fast spliced aligner with low memory requirements. Nature methods, 12, 357-360.
67. Li, H., Handsaker, B., Wysoker, A., Fennell, T., Ruan, J., Homer, N., Marth, G., Abecasis, G. and Durbin, R. (2009)

The Sequence Alignment/Map format and SAMtools. Bioinformatics, 25, 2078-2079.
68. Martin, M. (2011) Cutadapt removes adapter sequences from high-throughput sequencing reads. EMBnet.journal, 17, 10-12.
69. Xia, Z., Donehower, L. A., Cooper, T. A., Neilson, J. R., Wheeler, D. A., Wagner, E. J. and Li, W. (2014) Dynamic analyses of alternative polyadenylation from RNA-seq reveal a 3_-UTR landscape across seven tumour types. Nat. Commun., 5, 5274. REFERENCES—EXAMPLE 2
[70] Lin Y, Golovnina K, Chen Z X, Lee H N, Negron Y L, Sultana H, et al. Comparison of normalization and differential expression analyses using RNA-Seq data from 726 individual *Drosophila melanogaster*. BMC Genomics. 2016; 17:28.
[71] Routh A, Ji P, Jaworski E, Xia Z, Li W, Wagner E J. Poly(A)-ClickSeq: click-chemistry for next-generation 3-end sequencing without RNA enrichment or fragmentation. Nucleic Acids Res. 2017.
[72] Xiong Y, Soumillon M, Wu J, Hansen J, Hu B, van Hasselt J G C, et al. A Comparison of mRNA Sequencing with Random Primed and 3'-Directed Libraries. Scientific reports. 2017; 7: 14626.
[73] Routh A, Ji P, Jaworski E, Xia Z, Li W, Wagner E J. Poly(A)-ClickSeq: click-chemistry for next-generation 3'-end
sequencing without RNA enrichment or fragmentation. bioRxiv. 2017.
[74] Moll P, Ante M, Seitz A, Reda T. QuantSeq 3' mRNA sequencing for RNA quantification. Nature methods. 2014; 11:i-iii.
[75] Galatro T F, Holtman I R, Lerario A M, Vainchtein I D, Brouwer N, Sola P R, et al. Transcriptomic analysis of purified human cortical microglia reveals age-associated changes. Nat Neurosci. 2017; 20:1162-71.
[76] Proudfoot N J. Ending the message: poly(A) signals then and now. Genes Dev. 2011; 25:1770-82.
[77] Szkop K J, Nobeli I. Untranslated Parts of Genes Interpreted: Making Heads or Tails of High-Throughput Transcriptomic Data via Computational Methods: Computational methods to discover and quantify isoforms with alternative untranslated regions. Bioessays. 2017; 39.
[78] Routh A, Head S R, Ordoukhanian P, Johnson J E. ClickSeq: Fragmentation-Free Next-Generation Sequencing via Click Ligation of Adaptors to Stochastically Terminated 3'-Azido cDNAs. Journal of molecular biology. 2015.
[79] El-Sagheer A H, Sanzone A P, Gao R, Tavassoli A, Brown T. Biocompatible artificial DNA linker that is read through by DNA polymerases and is functional in *Escherichia coli*. Proc Natl Acad Sci USA. 2011; 108: 11338-43.
[80] Jaworski E, Routh A. ClickSeq: Replacing Fragmentation and Enzymatic Ligation with Click-Chemistry to Prevent Sequence Chimeras. Methods Mol Biol. 2018; 1712:71-85.
[81] Schneider I. Cell lines derived from late embryonic stages of *Drosophila melanogaster*. Journal of embryology and experimental morphology. 1972; 27:353-65.
[82] Rohland N, Reich D. Cost-effective, high-throughput DNA sequencing libraries for multiplexed target capture. Genome Res. 2012; 22:939-46.
[83] Chen S, Zhou Y, Chen Y, Gu J. fastp: an ultra-fast all-in-one FASTQ preprocessor. Bioinformatics. 2018; 34:i884-i90.
[84] Dobin A, Davis C A, Schlesinger F, Drenkow J, Zaleski C, Jha S, et al. STAR: ultrafast universal RNA-seq aligner. Bioinformatics. 2013; 29:15-21.
[85] Kim D, Langmead B, Salzberg SL. HISAT: a fast spliced aligner with low memory requirements. Nature methods. 2015; 12:357-60.
[86] O'Leary N A, Wright M W, Brister J R, Ciufo S, Haddad D, McVeigh R, et al. Reference sequence (RefSeq) database at NCBI: current status, taxonomic expansion, and functional annotation. Nucleic Acids Res. 2016; 44:D733-45.
[87] Liao Y, Smyth G K, Shi W. featureCounts: an efficient general purpose program for assigning sequence reads to genomic features. Bioinformatics (Oxford, England). 2014; 30:923-30.
[88] Love M I, Huber W, Anders S. Moderated estimation of fold change and dispersion for RNA-seq data with DESeq2. Genome Biol. 2014; 15:550.
[89] Routh A, Head S R, Ordoukhanian P, Johnson J E. ClickSeq: Fragmentation-Free Next-Generation Sequencing via Click Ligation of Adaptors to Stochastically Terminated 3'-Azido cDNAs. J Mol Biol. 2015; 427: 2610-6.
[90] Jaworski E, Routh A. Parallel ClickSeq and Nanopore sequencing elucidates the rapid evolution of defective-interfering RNAs in Flock House virus. PLoS pathogens. 2017; 13:e1006365.
[91] Anders S, Huber W. Differential expression analysis for sequence count data. Genome Biology. 2010; 11:R106.
[92] Zhang Y, Carrion S A, Zhang Y, Zhang X, Zinski A L, Michal J J, et al. Alternative polyadenylation analysis in animals and plants: newly developed strategies for profiling, processing and validation. International Journal of Biological Sciences. 2018; 14:1709-14.
[93] Masamha C P, Wagner E J. The contribution of alternative polyadenylation to the cancer phenotype. Carcinogenesis. 2018; 39:2-10.
[94] Masamha C P, Xia Z, Yang J, Albrecht T R, Li M, Shyu A B, et al. CFIm25 links alternative polyadenylation to glioblastoma tumour suppression. Nature. 2014; 510:412-6.
[95] Acevedo A, Brodsky L, Andino R. Mutational and fitness landscapes of an RNA virus revealed through population sequencing. Nature. 2014; 505:686-90.
[96] Qin Y, Yao J, Wu D C, Nottingham R M, Mohr S, Hunicke-Smith S, et al. High-throughput sequencing of human plasma RNA by using thermostable group II intron reverse transcriptases. RNA. 2016; 22:111-28.
[97] Trapnell C, Roberts A, Goff L, Pertea G, Kim D, Kelley D R, et al. Differential gene and transcript expression analysis of RNA-seq experiments with TopHat and Cufflinks. Nature protocols. 2012; 7:562-78.
[98] Jabara C B, Jones C D, Roach J, Anderson J A, Swanstrom R. Accurate sampling and deep sequencing of the HIV-1 protease gene using a Primer ID. Proc Natl Acad Sci USA. 2011; 108:20166-71.
[99] Miura F, Fujino T, Kogashi K, Shibata Y, Miura M, Isobe H, et al. Triazole linking for preparation of a next-generation sequencing library from single-stranded DNA. Nucleic Acids Res. 2018; 46:e95.

What is claimed is:

1. A kit for cDNA synthesis of an RNA 3' end, a poly (A) junction, and a poly (A) tail of RNA comprising:
one or more vials comprising three terminating nucleotides of modified-deoxyGTP, modified-deoxyCTP and modified-deoxyATP, dNTPs, and an adaptor sequence-oligo-dT, wherein the terminating modified-deoxyGTP, modified-deoxyCTP and modified-deoxyATP are 2'- or 3'-azido-nucleotides: AzGTP, AzCTP and AzATP; or 3'-(O-Propargyl)-NTPs that pair with an alkyne- or azide-modified oligo during a click reaction is a hexanyl-oligo or azide-oligo;
one or more vials comprising a reverse transcriptase;
a cDNA fragment isolating kit;
one or more vials comprising components for chemically ligating a functionalized 5' adaptor to the cDNA;
a DNA amplification kit for amplifying the chemically-ligated cDNA into an amplification product; and
instructions for amplification of the RNA 3' end and poly (A) tail junction without fragmentation and enzymatic ligation.

2. The kit of claim 1, wherein a ratio of the three 2'- or 3'-azido-nucleotides (AzGTP, AzCTP and AzATP), or propargyl-GTP, propargyl-CTP, or propargyl-ATP, to dNTPs is 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM: 1 mM.

3. The kit of claim 1, wherein a ratio of AzGTP:AzCTP: AzATP is x:y:z, wherein x is 0.1-2.0, y is 0.1-2.0, and z is 0.1-2.0.

4. The kit of claim 1, further comprising wherein the RNA 3' end and poly (A) tail junction is selected from the group consisting of a viral genomic RNA, total cellular RNA, poly (A)-selected RNA, unpurified DNA and ribo-depleted RNA.

5. The kit of claim 1, wherein the cDNA fragment isolating kit is selected from the group consisting of a column separation kit, magnetic bead separation kit, and streptavidin magnetic bead kit.

6. The kit of claim 1, further comprising a clicked-cDNA-adaptor purification kit for separating the clicked-cDNA-adaptor away from unligated alkyne-functionalized 5' adaptors.

7. The kit of claim 1, wherein click-ligating components comprise: an alkyne-functionalized 5' adaptor to the azido-terminated cDNA; a buffered solution comprising: a solvent mix comprising dimethylsulfoxide, water, and ethanol; metal catalysts selected from the group consisting of copper and ruthenium; a chelating ligand; and an accelerant.

8. The kit of claim 1, wherein the reverse transcriptase (RT) is selected from the group consisting of an RT derived from Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (−) Reverse Transcriptase, SuperScript II Reverse Transcriptase, SuperScript III Reverse Transcriptase, SuperScript IV Reverse Transcriptase, thermostable group II intron reverse transcriptases (TGIRT), Therminator DNA Polymerase, and ThermoScript Reverse Transcriptase, wherein an RNase H activity of these RTs is present, reduced or not present.

9. The kit of claim 1, further comprising least one molecule selected from the group consisting of trehalose, betaine, tetramethylammonium chloride, tetramethylammonium oxalate, formamide and oligo-blockers, and dimethylsulfoxide during the polymerase chain reaction, to reduce the occurrence of mispriming.

10. The kit of claim 1, further comprising a sequencing kit for determining an identity or sequence of the amplification products by an automated process selected from the group consisting of: on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, and single molecule sequencing.

11. The kit of claim 1, wherein a DNA polymerase for amplification is selected from the group consisting of Taq DNA polymerase, Tfl DNA polymerase, a Taq DNA polymerase, a Klenow fragment, Sequenase or Klentaq; or an enzyme with proof reading activity selected from the PFU, Ultma, Vent, Deep Vent, PWO, and Tli polymerases.

12. The kit of claim 1, further comprising a kit for purifying a PCR product from the step of amplifying the clicked-cDNA step with a column or beads.

13. The kit of claim 1, wherein an alkyne-functionalized 5' adaptor comprises all nucleotides NNNNNN, No-12 as a click adapter, semi-random primers, or a specific template primer sequence, and the adapter comprises a unique sequence.

* * * * *